US009772302B2

(12) United States Patent
Zelin et al.

(10) Patent No.: US 9,772,302 B2
(45) Date of Patent: Sep. 26, 2017

(54) QUALITY ASSURANCE SYSTEM AND METHOD FOR POINT-OF-CARE TESTING

(71) Applicant: Abbott Point of Care Inc., Princeton, NJ (US)

(72) Inventors: Michael P. Zelin, Plainsboro, NJ (US); Eric Brouwer, Ottawa (CA); Steven Breeze, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 242 days.

(21) Appl. No.: 13/930,299

(22) Filed: Jun. 28, 2013

(65) Prior Publication Data
US 2013/0292246 A1 Nov. 7, 2013

Related U.S. Application Data

(62) Division of application No. 12/210,700, filed on Sep. 15, 2008, now Pat. No. 8,510,067.
(Continued)

(51) Int. Cl.
*G01N 37/00* (2006.01)
*G01N 27/416* (2006.01)
(Continued)

(52) U.S. Cl.
CPC .......... *G01N 27/4163* (2013.01); *G01K 3/04* (2013.01); *G01N 27/3274* (2013.01); *G01N 31/229* (2013.01); *G01N 2035/00089* (2013.01)

(58) Field of Classification Search
CPC ................................................. G01N 27/4163
(Continued)

(56) References Cited

U.S. PATENT DOCUMENTS 4,098,652 A   7/1978 Koenig
4,933,048 A   6/1990 Luaks
(Continued)

FOREIGN PATENT DOCUMENTS

EP   1 176 421   1/2002
EP   1 277 438   1/2003
(Continued)

OTHER PUBLICATIONS

European Communication, Result of Consultation for corresponding EP Appl. No. 04 719 716.5-1238 dated Apr. 19, 2012.
(Continued)

*Primary Examiner* — Toan Le
*Assistant Examiner* — Xiuquin Sun
(74) *Attorney, Agent, or Firm* — Kilpatrick Townsend & Stockton LLP

(57) ABSTRACT

An improved quality assurance system and method for point-of-care testing are disclosed. The present invention provides quality assurance for laboratory quality tests performed by a blood analysis system or the like at the point of patient care without the need for running liquid-based quality control materials on the analysis system. Quality assurance of a quantitative physiological sample test system is performed without using a quality control sample by monitoring the thermal and temporal stress of a component used with the test system. Alert information is generated that indicates that the component has failed quality assurance when the thermal and temporal stress exceeds a predetermined thermal-temporal stress threshold. Alternatively, the present invention provides quality assurance for laboratory quality tests performed by a blood analysis system or the like at the point of patient care by minimizing the need for running liquid-based quality control materials on the analysis system.

16 Claims, 35 Drawing Sheets

Related U.S. Application Data

(60) Provisional application No. 60/972,158, filed on Sep. 13, 2007.

(51) Int. Cl.
*G01K 3/04* (2006.01)
*G01N 27/327* (2006.01)
*G01N 31/22* (2006.01)
*G01N 35/00* (2006.01)

(58) Field of Classification Search
USPC .......................................................... 702/84
See application file for complete search history.

(56) References Cited

U.S. PATENT DOCUMENTS

| | | | |
|---|---|---|---|
| 5,096,669 A | 3/1992 | Lauks et al. | |
| 5,112,455 A | 5/1992 | Cozzette et al. | |
| 5,124,661 A | 6/1992 | Zelin et al. | |
| 5,200,051 A | 4/1993 | Cozzette et al. | |
| 5,212,050 A | 5/1993 | Mier et al. | |
| 5,447,440 A | 9/1995 | Davis et al. | |
| 6,042,264 A | 3/2000 | Prusik et al. | |
| 6,579,690 B1* | 6/2003 | Bonnecaze et al. | 435/14 |
| 6,773,563 B2 | 8/2004 | Matsumoto | |
| 2002/0029964 A1 | 3/2002 | Matsumoto | |
| 2002/0037238 A1 | 3/2002 | Haar et al. | |
| 2003/0062262 A1* | 4/2003 | Mansouri | G01N 33/492 204/400 |
| 2004/0173456 A1 | 9/2004 | Boos et al. | |
| 2004/0181528 A1* | 9/2004 | Tirinato | G06Q 10/087 |
| 2004/0212508 A1* | 10/2004 | Zweig | G01K 3/04 340/588 |
| 2006/0030049 A1 | 2/2006 | Bhimani et al. | |
| 2007/0233583 A1 | 10/2007 | Tirinato et al. | |
| 2009/0075259 A1 | 3/2009 | Carstens et al. | |

FOREIGN PATENT DOCUMENTS

| | | |
|---|---|---|
| EP | 1 624 303 | 2/2006 |
| WO | WO 02/05235 | 1/2002 |
| WO | WO 2004/081746 | 9/2004 |

OTHER PUBLICATIONS

S.B. Tiwari, "Temperature Sensitive Liposomes of Plumbagin", J. Drug Targeting 10, 2002, pp. 585-591. (Abstract Only.).

P. Chandaroy, "Temperature Controlled Content Release from Liposomes Encapsulating Pluronic F127", J. Controlled Release, 76, 2001, pp. 27-37.

H. Hayashi, "Temperature Sensitive Liposomes Using Copolymers of N-isopropylacrylamide", Bioconj. Chem. 10, 1999, pp. 412-418.

International Search Report for PCT/US2008/076409 dated Jul. 9, 2009 (7 pages).

Transmittal, International Search Report and Written Opinion of the International Searching Authority for International Application No. PC/US2008/076409.

P.J. Combleet and N. Gochman, "Incorrect Least Squares Regression Coefficients in Method-Comparison Analysis," Clinical Chemistry, 25:3, 1979, p. 432.

R. F. Martin, "General Deming Regression for Estimating Systematic Bias and Its Confidence Interval in method-Comparison Studies," Clinical Chemistry, 46:100, Jan. 2000, pp. 100-104.

Japanese Office Action for corresponding JP Appl. No. 2010-525067 mailed Dec. 20, 2013.

R. L. Magin, "Temperature-Dependent Drug Release from Large Unilamellar Liposomes," Cancer Drug Deliv., 1984; 1(2): 109-117.

\* cited by examiner

FIG. 8

| Test | Limit ± | Test | Limit ± |
|---|---|---|---|
| Sodium | 4 mmol/L | Glucose | Greater of 6mg/dL or 10% |
| Potassium | 0.5 mmol/L | BUN | Greater of 2 mg/dL or 9%, |
| Chloride | 5% | Creatinine | Greater of 0.3 mg/dL or 15% |
| $TCO_2$ | greater of 4 mmol/L or 10% | Hematocrit | 10.8% |
| Ionized calcium | Greater of 0.05 mmol/L or 5% | | |

TABLE (A) ATE Acceptance Criteria

| Test | Crit Value Ref. | Low Range | Low Critical | LER | Ref. Range | LER | High Range | High Critical | LER |
|---|---|---|---|---|---|---|---|---|---|
| Sodium mmol/L | 1,2 | 100-137 | 120 | 18 | 138-146 | 14 | 147-180 | 160 | 14 |
| Potassium mmol/L | 1 | 2-3.4 | 2.5 | 1.0 | 3.5-4.9 | 1.0 | 5-9 | 6.5 | 1.6 |
| Chloride mmol/L | 2 | 65-97 | 70 | 40% | 98-109 | 9% | 111-140 | 120 | 9.2% |
| $TCO_2$ mmol/L | 1 | 5-24 | 15 | 60% | 24-29 | 42% | 30-50 | 50 | 42% |
| Ionized Calcium mmol/L | 1,4 | 0.25-1.11 | 0.70 | 60% | 1.12-1.32 | 17.5% | 1.33-2.50 | 1.60 | 17.5% |
| Glucose mg/dL | * | | | | | | | | |
| Hct %PCV | 6 | 10-37 | 27 | 11 %PCV | 38-51 | 16.1% | 52-75 | 70 | 15 %PCV |

* Parkes error grid

TABLE (B): LER Acceptance Criteria Table: Electrolytes, Glucose and Hematocrit

| Test | Crit Value Ref. | Low Range | Low Critical | LER | Ref. Range | LER | High Range | High Critical | LER |
|---|---|---|---|---|---|---|---|---|---|
| BUN mgN/dL | 6 | <26 | 0 | +26 -NA | 26-50 | ±27 | >50 | 50 | ±54% |
| Creatinine mg/dL | 3 | <1.3 | 0 | +0.7 -NA | 1.3-2.0 | ±0.7 | >2.0 | 2 | ±35% |

Note: There are no clinical critically low values for BUN or Creatinine, so the low critical value was determined to be 0 mg/dl.

TABLE (C): LER Acceptance Criteria Table: BUN and Creatinine

FIG. 8
(cont.)

i-STAT CHEM8+ Level 1 Control
LOT B06321
Exp.: 2008-05

CLEW: A12

| CHEM8+ | | LOT | | |
|---|---|---|---|---|
| | | | x̄ (Mean) | P or S(x6xxx,x7xxx) R (Range) |
| Na | mmol/L, mEq/L | | 119 | 115-123 |
| K | mmol/L, mEq/L | | 2.8 | 2.4-3.2 |
| iCa | mmol/L | | 1.45 | 1.34-1.56 |
| | mg/dL | | 5.8 | 5.4-6.2 |
| | mEq/L | | 2.9 | 2.7-3.1 |
| TCO₂ | mmol/L, mEq/L | | 17.0 | 8.0-26.0 |
| Glucose/Glu | mg/dL | | 41 | 32-50 |
| | g/L | | 0.41 | 0.32-0.50 |
| | mmol/L | | 2.3 | 1.8-2.7 |
| Creatinine/Crea | mg/dL | | 4.6 | 3.8-5.4 |
| | umol/L | | 409 | 339-480 |
| Cl | mmol/L, mEq/L | | 76 | 71-81 |
| BUN | mg/dL | | 58 | 51-65 |
| Urea | mmol/L | | 20.6 | 18.1-23.1 |
| | mg/dL | | 124 | 109-139 |
| | g/L | | 1.24 | 1.09-1.39 |

FIG. 9(A)

i-STAT CHEM8+ Level 3 Control
LOT B06326
Exp.: 2008-05

CLEW: A12

| CHEM8+ | | LOT | | |
|---|---|---|---|---|
| | | | x̄ (Mean) | P or S(x6xxx,x7xxx) R (Range) |
| Na | mmol/L, mEq/L | | 157 | 152-162 |
| K | mmol/L, mEq/L | | 6.1 | 5.6-6.6 |
| iCa | mmol/L | | 0.69 | 0.61-0.77 |
| | mg/dL | | 2.8 | 2.4-3.1 |
| | mEq/L | | 1.4 | 1.2-1.5 |
| TCO₂ | mmol/L, mEq/L | | 31.5 | 25.4-37.6 |
| Glucose/Glu | mg/dL | | 286 | 244-328 |
| | g/L | | 2.86 | 2.44-3.28 |
| | mmol/L | | 15.9 | 13.5-18.2 |
| Creatinine/Crea | mg/dL | | 0.8 | 0.4-1.2 |
| | umol/L | | 72 | 36-107 |
| Cl | mmol/L, mEq/L | | 115 | 109-121 |
| BUN | mg/dL | | 6 | 4-8 |
| Urea | mmol/L | | 2.1 | 1.4-2.8 |
| | mg/dL | | 13 | 8-17 |
| | g/L | | 0.13 | 0.08-0.17 |

FIG. 9(B)

Hematocrit Level 1 Control
LOT B05173
Exp.: 2007-06

CLEW: A12

CHEM8+

| | | | x̄ (Mean) | P or S(x6xxx,x7xxx) R (Range) |
|---|---|---|---|---|
| HCT | K₃EDTA | % | 18.4 | 15.4-21.4 |
| | K₂EDTA | | 19.2 | 16.1-22.3 |

FIG. 10(A)

Hematocrit Level 3 Control
LOT B05180
Exp.: 2007-06

CLEW: A12

CHEM8+

| | | | x̄ (Mean) | P or S(x6xxx,x7xxx) R (Range) |
|---|---|---|---|---|
| HCT | K₃EDTA | % | 56.4 | 53.0-59.8 |
| | K₂EDTA | | 58.8 | 55.3-62.3 |

FIG. 10(B)

| Analyte | Units | Measurements with High crea/BUN/iCa control | | | Measurements with Low crea/BUN/iCa control | | | |
|---|---|---|---|---|---|---|---|
| | | cartridge from refrigerator | reading after 3wks @104 °F | ATE | Shift Under Stress (% of ATE) | cartridge from refrigerator | reading after 3wks @104 °F | ATE | Shift Under Stress (% of ATE) |
| creatinine | (mg/dl) | 4.52 | 3.72 | 15% | 118% | 0.81 | 0.92 | 0.3 | 39% |
| BUN | (mg/dl) | 58.7 | 53 | 9% | 107% | 6.1 | 5.9 | 2 | 7% |
| iCa | (mmol/l) | 1.47 | 1.54 | 0.07 | 98% | 0.75 | 0.79 | 0.05 | 78% |
| glucose | (mg/dl) | 41.0 | 42.7 | 6 | 30% | 286 | 297 | 10% | 37% |
| sodium | (mmol/l) | 119.3 | 119.2 | 4 | 1% | 157.1 | 157.2 | 4 | 25% |
| potassium | (mmol/l) | 2.84 | 2.82 | 0.5 | 2% | 6.12 | 6.07 | 0.5 | 11% |
| chloride | (mmol/l) | 77.3 | 77.2 | 5% | 4% | 114.7 | 115.2 | 5% | 10% |
| TCO$_2$ | (mmol/l) | 17.4 | 17.7 | 4 | 11% | 33.5 | 33.1 | 4 | 9% |

| Analyte | Units | Measurements with High HCT control | | | | Measurements with Low HCT control | | | |
|---|---|---|---|---|---|---|---|---|---|
| | | cartridge from refrigerator | reading after 3wks @104 °F | ATE | Shift Under Stress (% of ATE) | refrigerated control | reading after 3wks @104 °F | ATE | Shift Under Stress (% of ATE) |
| HCT | (%PCV) | 56.0 | 56.0 | 6.0 | 0% | 18.3 | 18.0 | 2.0 | 15% |

FIG. 32

CHEM8+ L1 control fluid lot number and expiry date: _____

CHEM8+ cartridge lot number and expiry date: _____

| Analyte | Units | Target | Range | Observed | Pass/Fail |
|---|---|---|---|---|---|
| iCa | mmol/L | 1.453 | 1.380 - 1.526 | | |
| BUN | mg/dL | 55.0 | 50.0 - 59.9 | | |
| Creatinine | mg/dL | 4.40 | 3.74 - 5.07 | | |
| Na | mmol/L | | | | |
| K | mmol/L | | | | |
| Cl | mmol/L | | | | |
| TCO2 | mmol/L | | | | |
| glucose | mg/dL | | | | |

Signature/Date: _____

FIG. 33

QUALITY ASSURANCE SYSTEM AND METHOD FOR POINT-OF-CARE TESTING

CROSS REFERENCE TO RELATED APPLICATIONS

This application is a divisional of U.S. application Ser. No. 12/210,700 filed Sep. 15, 2008, which issued as U.S. Pat. No. 8,510,067 on Aug. 13, 2013, which claims the benefit of priority under 35 U.S.C. §119(e) from U.S. Provisional Application Ser. No. 60/972,158, entitled "IMPROVED QUALITY ASSURANCE SYSTEM AND METHOD FOR POINT-OF-CARE-TESTING", filed on Sep. 13, 2007, the entire contents of which are incorporated herein by reference.

BACKGROUND

Field of the Invention

The present invention relates to quality assurance methodologies applied to physiological sample testing devices. More particularly, the present invention relates to an improved quality assurance system and method for point-of-care testing.

Background Information

There are several conventional quality assurance methodologies applied to physiological sample testing devices. Where these devices are used on human subjects, the quality assurance process is generally regulated by government, e.g., the Food and Drug Administration (FDA) in the United States of America. For tests and devices that are currently approved for sale over-the-counter to patients, quality assurance is provided by factory testing that provides a usable lifetime or expiration date. In the US, these are termed Clinical Laboratory Improvements Amendments (CLIA) waived tests. Such types of devices provide either qualitative results, as in the case of home pregnancy tests, or quantitative results, as in the case of home blood glucose testing devices. However, the required precision and accuracy of the latter group is not considered to be of the same level of quality as provided by a regulated clinical blood testing laboratory.

Tests and devices that are approved to be used in a clinical laboratory are generally covered by a different set of regulations. Such systems can primarily be categorized as being designed to provide good quality quantitative results, where the reported precision is usually about 10% or better. Skilled users, e.g. clinical laboratory technicians, are required to run the testing systems, and the systems are generally categorized by the regulatory agency as moderately complex. Those skilled in the art will recognize that extensive background information is available at the FDA website. Regarding these systems, there is a current requirement that liquid-based quality control materials are run at regular intervals to ensure that the system is working properly. Such liquid controls are supplied with an expected range of values for a given test. Consequently, when a system is challenged with the liquid control material, the system should report a value within that given range. Where the system reports a result that is out of range, servicing of that system is required. Such a process of quality testing and instrument maintenance is performed by a trained laboratory technician. While it is desirable that any analytical system always runs within specifications, the complexity of this equipment is often at odds with such a desire. It is noted that systems designed by manufacturers for laboratory use have conventionally anticipated that, from time to time, those systems will be out of specification, based on liquid quality control testing, and that technicians are specifically trained to service the system so that it can be brought back into specification.

Over the last several years, a new methodology for blood testing has arisen, termed point-of-care or bedside testing. Such testing is generally performed in a hospital, e.g., emergency room and operating room, but outside of the clinical laboratory. Such testing can also be performed in a physician's office or a temporary or mobile location, e.g., a MASH unit, ambulance, cruise ship, or other like location. Several technologies have been developed for point-of-care testing, and some have the capability of delivering laboratory quality test results (e.g., systems sold by i-STAT Corporation of East Windsor, N.J.). In other words, such point-of-care test systems have the same or substantially similar level of precision and accuracy as achieved in a laboratory test. Such newer systems are generally based on a reader and single-use, disposable test devices or cartridges.

One of the main values of point-of-care blood testing systems is that they have eliminated the time-consuming need to send a patient's blood sample to a central laboratory for testing. These systems are sufficiently easy to operate such that a nurse, at the bedside, can obtain a reliable quantitative analytical result, equivalent in quality to the laboratory. For example, the nurse can select a cartridge with the required panel of tests, draw a blood sample, dispense it into the cartridge, seal the cartridge, and inserts it into the reading device. The reading device then performs a test cycle, i.e., all the other analytical steps required to make the tests. Such simplicity gives the physician more speedy insight into a patient's physiological status. In addition, by reducing the time for evaluation, such point-of-care systems enable a quicker decision by the physician on the appropriate treatment, thus enhancing the likelihood of a successful patient outcome.

In the emergency room and other acute care locations within a hospital, the types of blood tests required for individual patients tends to vary. Thus, point-of-care systems generally offer a range of disposable cartridges with different menus of blood tests. In addition to tests for sodium, potassium, chloride, calcium, partial pressure of oxygen (pO2), partial pressure of carbon dioxide (pCO2), pH, glucose, hematocrit, lactate, blood urea nitrogen (BUN) and creatinine, others tests can include, but are not limited to, prothrombin time (PT), activated clotting time (ACT), activated partial thromboplastin time (APTT), troponin I, troponin T, creatine kinase MB (CKMB), brain natriuretic peptide (BNP), NTproBNP and C-reactive protein (CRP). As is well known in the art, several other parameters can be calculated from these test results, including, for example, base excess (BE) and percentage of oxygen saturation (% O2 sat). These tests can be provided in several combinations presented to the user as a single-use device, e.g., a disposable cartridge. For example, the I-STAT system offers hospitals more than ten types of cartridges with menus that range from one to eight blood tests.

In some cases, cartridges, such as those supplied by i-STAT Corporation, have a shelf-life of about six to about nine months when refrigerated, but only a limited shelf-life, e.g., about two weeks at room temperature, or, more specifically, about two weeks at up to about 30° C. As a result, a hospital will generally store cartridges at a central refrigerated location, and deliver cartridges to specific departments as demand requires. These departments may or may not have available refrigerated storage, and this will affect the inventory they will hold. In certain departments, general storage may be limited, and such a situation will also affect what level of inventory they hold. A given user, such as a hospital, may use multiple types of cartridges and need to ensure the quality of test results at each point-of-care testing location. These locations can include, for example, an emergency room (ER), critical care unit (CCU), pediatric intensive care unit (PICU), intensive care unit (ICU), renal dialysis unit (RDU), operating room (OR), cardiovascular operating room (CVOR) and general wards (GW). Alternatively, the user may be a physician's office laboratory or visiting nurse service. However, the need to ensure quality is the same.

For hospitals, the recent introduction of point-of-care blood testing capabilities has created novel requirements for quality assurance. Such requirements arise from multiple types of disposable blood testing cartridges being used at multiple locations within a given hospital. However, the objective for the hospital is to provide a high level of quality assurance for each type of cartridge at each site of use.

Conventionally, systems offering laboratory quality results were regulated such that some form of liquid quality controls were required to be run by the customer. For example, for the i-STAT system that is based on a handheld reader and single-use cartridges, a statistical sample from a shipment of cartridges is required to be tested by the customer upon receipt. If these cartridges are found to be within specifications, then the whole shipment can be used by the customer for point-of-care testing. For example, one method applied to the i-STAT system, where a particular cartridge type reported results for hematocrit and several blood chemistries, required running four cartridges—two different hematocrit control fluids and two more using two different chemistry control fluids.

More particularly, cartridges are generally supplied by the manufacture to the user in boxes with a given number of units, e.g., twenty-five cartridges of one type. The conventional quality assurance method requires that a statistical sample of these cartridges be tested with control fluids and pass, prior to the remainder being released for use with patient samples. The origins of such a method lay in the historical development of quantitative blood testing systems, where the analytical component, such as a flow cell or cuvette, was re-used many times with different samples. Such reuse could lead to drift in the analytical output, as identified when the system is challenged with control fluids. When the system is shown to be operating outside specifications, servicing is required. As these systems were generally located in a central hospital laboratory, skilled technician trained specifically for this purpose provided the servicing.

Such a general type of liquid control testing is appropriate for many laboratory-based systems where the same detector, such as an optical cuvette chamber and electrode, is re-used many times in making a measurement. For example, a traditional blood gas analyzer that has an array of electrodes (e.g., pH, pCO2, pO2, and the like) can pass though many repeated test cycles where a calibrant fluid or gas is applied, then the sample, and finally a wash fluid. Such electrodes over time can become fouled with residual sample components (e.g., protein or the like), despite performance of the automatic wash step after each sample is run. Here, the intermittent use of liquid controls helps to ensure that a system where a repeatedly used component (e.g., an electrode) that has drifted out of specification is identified and corrected within a period of several hours. By contrast, a system that is based on electrodes or other detection devices that are only used once and then discarded, such as in the i-STAT system, does not experience the kind of drift during use common to reusable detection devices.

As one skilled in the art will recognize, during the development of a testing system, performance characteristics will be determined. Precision data are generally collected at multiple test sites and a method comparison performed versus one or more commercially established systems. Typically, a Deming (or General Deming) regression analysis is used to provide estimates of imprecision between the new and old methods and to provide a standard error of estimates (Sy.x) and correlation coefficient (r), as described in, for example, P. J. Cornbleet and N. Gochman, "Incorrect Least Squares Regression Coefficients in Method-Comparison Analysis," Clinical Chemistry 25:3, 432 (1979); and R. F. Martin, "General Deming Regression for Estimating Systematic Bias and Its Confidence Interval in Method-Comparison Studies," Clinical Chemistry 46:100-104 (January 2000).

Precision data for the control fluids are also determined to provide a mean (M), standard deviation (SD), and percent coefficient of variation (% CV). By way of example, the following table summaries precision data for the aforementioned i-STAT system for various tests using control fluids at different levels. These values are illustrative of laboratory quality systems delivering quantitative results to a precision of about 10% or better.

TABLE 1

Precision Data for the i-STAT System

| Aqueous Control | Mean | SD | % CV |
|---|---|---|---|
| Level 1 potassium | 2.85 mM | 0.038 | 1.33 |
| Level 3 potassium | 6.30 mM | 0.039 | 0.62 |
| Level 1 sodium | 120.0 mM | 0.46 | 0.38 |
| Level 3 sodium | 160.0 mM | 0.53 | 0.33 |
| Level 1 glucose | 41.8 mg/dL | 0.68 | 1.63 |
| Level 3 glucose | 289 mg/dL | 2.40 | 0.83 |
| Level 1 BUN | 5.5 mg/dL | 0.45 | 8.18 |
| Level 3 BUN | 52.8 mg/dL | 0.76 | 1.44 |
| Level 1 chloride | 76.7 mM | 0.54 | 0.70 |
| Level 3 chloride | 114.0 mM | 0.56 | 0.49 |
| Level 1 hematocrit | 30% | 0.44 | 1.47 |
| Level 3 hematocrit | 49% | 0.50 | 1.02 |
| Level 1 calcium | 0.84 mM | 0.012 | 1.43 |
| Level 3 calcium | 1.6 mM | 0.017 | 1.06 |
| Level 1 creatinine | 0.76 mM | 0.05 | 6.58 |
| Level 3 creatinine | 4.7 mM | 0.08 | 1.70 |
| Level 1 TCO2 | 18.2 mmHg | 0.21 | 1.15 |
| Level 3 TCO2 | 38 mmHg | 0.41 | 1.08 |
| Level 1 lactate | 0.81 mM | 0.03 | 3.70 |
| Level 3 lactate | 6.35 mM | 0.08 | 1.26 |
| Level 1 pH | 7.165 | 0.005 | 0.07 |
| Level 3 pH | 7.656 | 0.003 | 0.04 |
| Level 1 pCO2 | 19.6 mmHg | 0.40 | 2.04 |
| Level 3 pCO2 | 63.8 mmHg | 1.57 | 2.46 |
| Level 1 pO2 | 65.1 mmHg | 3.12 | 4.79 |
| Level 3 pO2 | 146.5 mmHg | 6.00 | 4.10 |
| Level 1 ACTc | 221 seconds | 18.00 | 8.10 |
| Level 3 ACTc | 456 seconds | 22.00 | 4.80 |
| Level 1 ACTk | 169 seconds | 4.00 | 2.00 |
| Level 3 ACTk | 409 seconds | 21.00 | 5.20 |
| Level 1 PT | 1.1 seconds | 0.05 | 4.50 |
| Level 3 PT | 2.5 seconds | 0.17 | 6.90 |
| Level 1 cTnI | 0.53 ng/mL | 0.04 | 7.80 |
| Level 3 cTnI | 31.82 ng/mL | 2.42 | 7.60 |
| Level 1 CKMB | 5.90 ng/mL | 0.70 | 11.9 |
| Level 3 CKMB | 25.80 ng/mL | 2.70 | 10.4 |
| Level 1 BNP | 126 pg/mL | — | 9.0 |
| Level 2 BNP | 1551 pg/mL | — | 6.6 |
| Level 3 BNP | 3337 pg/mL | — | 8.0 |

For example, a conventional method of performing quality assurance, such as that used by the i-STAT system, for cartridges comprising tests for blood chemistries and hematocrit is as follows. Cartridges are shipped from the manufacture with an ice-pack in an insulated box to arrive at the customer within two business days. Within the box is a temperature strip containing a red wax that changes color if it has experienced a temperature elevation for a certain time. If this occurs, the user is instructed to either return the shipment or call the supplier for further instructions. Assuming the cartridges arrive safely and the temperature strip has not been triggered, then the cartridges are transferred to refrigerated storage. At this point, four cartridges are removed and checked with four different control fluids. Such checking is performed with two control fluids that represent different chemistry values and two control fluids that represent two different hematocrit levels. If all four cartridges report results consistent with the expected values for the controls, then the rest of the cartridges are available for release from storage to be sent to one or more point-of-care locations.

While such a method of operation is generally acceptable for point-of-care locations within large institutions, such as, for example, a hospital or the like, that use a substantial number of cartridges per year, it is less suitable for other point-of-care locations, such as a physician's office. In particular, a physician generally orders less cartridges and uses them at a lower rate than a hospital. As a result, the performance of running liquid controls on single-use test devices intended to give laboratory quality results at the point-of-care can be burdensome on certain customers, and can in certain circumstances reduce the desirability of using the technology. Consequently, there remains a need for a quality testing methodology for the physician's office and other low volume point-of-care users (e.g., nursing homes) that is simpler to manage. In addition, the development of newer testing systems based on single-use analytical devices, in combination with the desire to provide testing services right at the point of patient care, has generated a need for quality control methodologies that better meet the needs of point-of-care testing. As a result, there remains the need for an improved means for providing quality assurance, preferably without the need for using liquid quality controls by the customer. Furthermore, there remains a need for an improved means for providing quality assurance that significantly reduces the number of liquid quality controls used by the customer.

SUMMARY OF THE INVENTION

A system and method are disclosed for an improved quality assurance system and method for point-of-care testing. In accordance with exemplary embodiments of the present invention, according to a first aspect of the present invention, a system for performing quality assurance of a quantitative physiological sample test system without using a quality control sample includes a thermal and temporal stress monitor module. The thermal and temporal stress monitor module is configured to monitor thermal and temporal stress of a component used with the test system. The system includes a quality assurance failure alert module in communication with the thermal and temporal stress monitor module. The quality assurance failure alert module is configured to generate alert information indicating that the component has failed quality assurance when the thermal and temporal stress exceeds a predetermined thermal-temporal stress threshold.

According to the first aspect, he physiological sample can comprise one of blood, plasma, serum, saliva, urine, cerebrospinal fluid, and amended forms thereof. The quality control sample can comprise a liquid control or the like. The component can be used with the test system when the thermal and temporal stress does not exceed the predetermined thermal-temporal stress threshold. The thermal and temporal stress monitor module can be separate from the test system and in a substantially same thermal environment as the test system. Alternatively, the thermal and temporal stress monitor module can be integrated with the test system. The thermal and temporal stress monitor module can be configured to monitor a temperature-time indicator associated with the component. For example, the thermal and temporal stress monitor module can comprise at least one of an electrically conductive wax, a temperature-dependent liquid crystal, a shift in baseline calibration potential of a potentiometric sensor, a liposomal release of an enzyme inhibitor, a liposomal release of an electrically conductive liquid, a liposomal release of an elevated ion concentration, a liposomal release of a molecule or ion capable of electrochemical detection, a thermistor, a thermocouple, a thermal ink, a temperature-dependent chemical reaction, a temperature-dependent color changing patch, and a temperature-dependent phase change of a material.

According to the first aspect, the component can comprise a sample testing cartridge or the like. The test system can comprise a blood analysis system or the like. The blood analysis system can comprise a portable component reader or the like. For example, the component can comprise a blood testing cartridge or the like, such as a single-use blood testing cartridge. The blood testing cartridge can include at least one electrochemical sensor. The component can comprise a sensor or the like. For example, the sensor can comprise one of an electrochemical sensor, an optical sensor, a luminescence sensor, a fluorescence sensor, an amperometric sensor, a potentiometric sensor, a conductimetric sensor, a wave guide, an evanescence sensor, a biosensor, a surface plasmon resonance sensor, an acoustic wave sensor, and a reflectance sensor. The component can be stored in a refrigerated enclosure below a predetermined temperature. The component can be removed from the refrigerated enclosure prior to use with the test system. The component can be allowed to attain ambient temperature prior to being used with the test system. The test system can be configured to perform a test to determine an analyte. For example, the analyte can comprise one of sodium, potassium, chloride, calcium, glucose, lactate, creatinine, urea, hematocrit, prothrombin time, activated clotting time, activated partial thromboplastin time, troponin I, troponin T, creatine kinase MB, brain natriuretic peptide, NTproBNP, C-reactive protein, pO2, PCO2, and pH.

According to the first aspect, the component can be associated with a batch of substantially similar components. The quality assurance failure alert module can be configured to generate alert information indicating that the batch has failed quality assurance when the thermal and temporal stress of the component exceeds the predetermined thermal-temporal stress threshold. The test system can be configured to perform at least one failsafe check prior to use of the component. For example, the failsafe check can comprise at least one of verification that an ambient temperature is within a predetermined range, verification that the component is not faulty, and verification that the test system is not faulty. The verification that the test system is not faulty can comprise at least one of testing electrical integrity of an electrical connector associated with the test system, and testing operational integrity of operational amplifiers associated with the test system.

According to the first aspect, the test system can comprise an electronic simulator. The electronic simulator can be configured to simulate signals produced by the component. The electronic simulator can be configured to generate simulation signals for testing at least one of electrical integrity of an electrical connector associated with the test system and operational integrity of operational amplifiers associated with the test system. The test system can comprise a display module. The display module can be configured to display alerts in accordance with the alert information. The test system can be configured to suppress display of test results when the component has failed quality assurance. The system can comprise a log module in communication with the quality assurance failure alert module. The log module can be configured to maintain a log of the thermal and temporal stress of a plurality of components. The predetermined thermal-temporal stress threshold can be generated in accordance with a total allowable error of the test system. The predetermined thermal-temporal stress threshold can comprise a plurality of combinations of thermal stress and temporal stress. The predetermined thermal-temporal stress threshold can comprise a predetermined temperature-time profile.

According to a second aspect of the present invention, a system for evaluating thermal and temporal stress quality assurance of a quantitative electrochemical physiological sample test system includes a first electrochemical sensor and a second electrochemical sensor. The first and second electrochemical sensors are contacted with a calibrant fluid. The first electrochemical sensor is configured to determine a first calibration voltage associated with the concentration of a first analyte in the calibrant fluid in accordance with a first check threshold. The second electrochemical sensor is configured to determine a second calibration voltage associated with the concentration of a second analyte in the calibrant fluid in accordance with a second check threshold. The test system is disqualified from performing a physiological sample test when both the first and second check thresholds are exceeded. According to the second aspect, the first electrochemical sensor can comprise a sodium ion-selective electrode. The second electrochemical sensor can comprise a calcium ion-selective electrode.

According to a third aspect of the present invention, a system for thermal and temporal stress quality assurance of a quantitative electrochemical physiological sample test system includes a plurality of electrochemical sensors. The plurality of electrochemical sensors are contacted with a calibrant fluid. The system includes a calibration circuit in communication with the plurality of electrochemical sensors. The calibration circuit is configured to determine a calibration parameter associated with a concentration of an analyte in the calibrant fluid for each electrochemical sensor of a subset of the plurality of electrochemical sensors in accordance with a predetermined check threshold. The calibration circuit is configured to disqualify the test system from performing a physiological sample test when the predetermined check threshold is exceeded for each electrochemical sensor of the subset.

According to the third aspect, the subset of electrochemical sensors can comprise a calcium ion-selective electrode and a BUN electrode. Alternatively, the subset of electrochemical sensors can comprise a sodium ion-selective electrode, a calcium ion-selective electrode, and a BUN electrode. The calibration parameter can comprise a calibration voltage. In the alternative, the calibration parameter can comprise a calibration voltage drift rate. Alternatively, the calibration parameter can comprise a combination of a calibration voltage and a calibration voltage drift rate. Each of the plurality of electrochemical sensors can comprise one of a sodium sensor, a potassium sensor, a chloride sensor, a pH sensor, a pO2 sensor, a pCO2 sensor, a lactate sensor, a glucose sensor, a creatinine sensor, a BUN electrode, a calcium sensor, a magnesium sensor, and a hematocrit sensor.

According to a fourth aspect of the present invention, a method of quality assurance of a quantitative physiological sample test system performed without running a quality control sample, comprising the steps of: monitoring thermal and temporal stress of a component used with the test system; and generating alert information indicating that the component has failed quality assurance when the thermal and temporal stress exceeds a predetermined thermal-temporal stress threshold.

According to the fourth aspect, he predetermined thermal-temporal stress threshold can be generated in accordance with a total allowable error of the test system. The predetermined thermal-temporal stress threshold can comprise a plurality of combinations of temperature and time. The component can be used with the test system when the thermal and temporal stress do not exceed the predetermined thermal-temporal stress threshold. The monitoring step can be performed using at least one of an electrically conductive wax, a temperature-dependent liquid crystal, a shift in baseline calibration potential of a potentiometric sensor, a liposomal release of an enzyme inhibitor, a liposomal release of an electrically conductive liquid, a liposomal release of an elevated ion concentration, a liposomal release of a molecule or ion capable of electrochemical detection, a thermistor, a thermocouple, a thermal ink, a temperature-dependent chemical reaction, a temperature-dependent color changing patch, and a temperature-dependent phase change of a material. The monitoring and generating steps can be performed at one of a hospital central laboratory, a satellite laboratory, a point-of-care location, a patient bedside, a moving vehicle, and a laboratory services vendor. The test system can comprise a blood analysis system or the like. The blood analysis system can comprise a portable component reader or the like. The component can comprise a blood testing cartridge, such as a single-use blood testing cartridge. The blood testing cartridge can comprise at least one electrochemical sensor. The physiological sample can comprise one of blood, plasma, serum, saliva, urine, cerebrospinal fluid, and amended forms thereof.

According to the fourth aspect, the method can one or more of the following steps: storing the component in a refrigerated enclosure below a predetermined temperature; storing the component in a refrigerator below a predetermined temperature; removing the component from the refrigerator prior to use with the test system; and allowing the component to attain room temperature prior to being used to perform a test. The quality control sample can comprise a liquid control or the like. The component can comprise a sensor or the like. For example, the sensor can comprise one of an electrochemical sensor, an optical sensor, a luminescence sensor, a fluorescence sensor, an amperometric sensor, a potentiometric sensor, a conductimetric sensor, a wave guide, an evanescence sensor, a biosensor, a surface plasmon resonance sensor, an acoustic wave sensor, and a reflectance sensor. The test system can perform a test to determine an analyte. For example, the analyte can comprise one of sodium, potassium, chloride, calcium, glucose, lactate, creatinine, urea, hematocrit, prothrombin time, activated clotting time, activated partial thromboplastin time, troponin I, troponin T, creatine kinase MB, brain natriuretic peptide, NTproBNP, C-reactive protein, pO2, PCO2, and pH.

According to the fourth aspect, the component can be associated with a batch of substantially similar components. The method can include the step of generating alert information indicating that the batch has failed quality assurance when the thermal and temporal stress of the component exceeds the predetermined thermal-temporal stress threshold. The test system can perform at least one failsafe check prior to use of the component. For example, for the failsafe check the test system can perform at least one of the steps of i.) verifying that an ambient temperature is within a predetermined range, ii.) verifying that the component is not faulty, and iii.) verifying that the test system is not faulty. For step (iii) the test system can perform at least one of the steps of 1.) testing electrical integrity of an electrical connector associated with the test system, and 2.) testing operational integrity of operational amplifiers associated with the test system. The method can include the step of simulating signals produced by the component. The simulating step can include one or more of the steps of: generating simulation signals for testing electrical integrity of an electrical connector associated with the test system; and generating simulation signals for testing operational integrity of operational amplifiers associated with the test system. The method can include one or more of the following steps: displaying alerts in accordance with the alert information; suppressing display of test results when the component has failed quality assurance; and maintaining a log of the thermal and temporal stress of a plurality of components.

According to a fifth aspect of the present invention, a method of quality assurance of a quantitative blood sample testing system not requiring running one or more liquid quality control samples, in which the testing system comprises a point-of-care test reader and a plurality of single-use test devices for performing one or more tests, and wherein each of the tests is performed to a precision of better than about 10%, comprises the steps of: monitoring at least one of the plurality of single-use test devices in accordance with thermal and temporal stress and a predetermined thermal-temporal stress threshold; and selecting the single-use test devices for testing a blood sample with the point-of-care test reader for which the associated thermal and temporal stress has not exceeded the predetermined thermal-temporal stress threshold.

According to a sixth aspect of the present invention, a method of quality assurance of a quantitative blood sample testing system not requiring running a liquid quality control sample or a set of quality control samples, in which the testing system comprises a re-usable portable reader and a plurality of single-use test devices for performing a selected menu of one or more tests, and wherein each of the tests is performed to a precision of better than about 10%, comprises the steps of: determining exposure of each of the single-use test devices to temporal and thermal stress in accordance with a predetermined time-temperature stress threshold by interrogating a time-temperature indicator associated with each single-use test device; and reporting blood test results for single-use test devices that have not exceeded the time-temperature stress threshold.

According to a seventh aspect of the present invention, a method of quality assurance of a quantitative blood sample testing system used for point-of-care testing, in which the testing system comprises a re-usable portable reader and a single-use test device for performing one or more tests for analytes in the blood sample, and wherein each analyte test is performed to a precision of better than about 10%, comprises the steps of: determining exposure of a batch of the single-use test devices to thermal and temporal stress by testing a single test device from the batch with a single control fluid containing a predetermined concentration of at least one analyte in the sample, wherein the analyte is selected to provide a test result indicative of thermal and temporal stress greater than a predetermined threshold of a total allowable error for the test; and indicating that the batch of test devices is unsuitable for use in blood sample testing when the test result is greater than the predetermined threshold.

According to an eighth aspect of the present invention, a method of thermal stress quality assurance of a quantitative electrochemical physiological sample test system comprises the steps of: contacting first and second electrochemical sensors with a calibrant fluid; determining a first calibration voltage associated with a concentration of a first analyte in the calibrant fluid in accordance with a first thermal check threshold; determining a second calibration voltage associated with the concentration of a second analyte in the calibrant fluid in accordance with a second thermal check threshold; and disqualifying the test system from performing a physiological sample test when both the first and second thermal check thresholds are exceeded. For example, the first electrochemical sensor can comprise a sodium ion-selective electrode, and the second electrochemical sensor can comprise a calcium ion-selective electrode.

According to a ninth aspect of the present invention, a method of thermal stress quality assurance of a quantitative electrochemical physiological sample test system, comprising the steps of: contacting a plurality of electrochemical sensors with a calibrant fluid; determining a calibration parameter associated with a concentration of an analyte in the calibrant fluid for each electrochemical sensor of a subset of the plurality of electrochemical sensors in accordance with a predetermined thermal check threshold; and disqualifying the test system from performing a physiological sample test when the predetermined thermal check threshold is exceeded for each electrochemical sensor of the subset.

According to the ninth aspect, the subset of electrochemical sensors can comprise a calcium ion-selective electrode and a BUN electrode. Alternatively, the subset of electrochemical sensors can comprise a sodium ion-selective electrode, a calcium ion-selective electrode, and a BUN electrode. The calibration parameter can comprise a calibration voltage. In the alternative, the calibration parameter can comprise a calibration voltage drift rate. Alternatively, the calibration parameter can comprise a combination of a calibration voltage and a calibration voltage drift rate. Each of the plurality of electrochemical sensors can comprise one of a sodium sensor, a potassium sensor, a chloride sensor, a pH sensor, a pO2 sensor, a pCO2 sensor, a lactate sensor, a glucose sensor, a creatinine sensor, a BUN electrode, a calcium sensor, a magnesium sensor, and a hematocrit sensor.

According to a tenth aspect of the present invention, a method of quality assurance of a quantitative physiological sample test system performed without running a quality control sample, comprising the steps of: monitoring thermal and temporal stress of a component of the test system; and determining suitability of using the component with the test system to perform the physiological sample test in accordance with the thermal and temporal stress of the component and a predetermined thermal-temporal stress threshold.

According to an eleventh aspect of the present invention, a system for performing quality assurance of a quantitative physiological sample test system without using a quality control sample includes a thermal and temporal stress monitor module. The thermal and temporal stress monitor module is configured to monitor thermal and temporal stress of a component used with the test system. The component is associated with a batch of substantially similar components. The system includes a quality assurance failure alert module in communication with the thermal and temporal stress monitor module. The quality assurance failure alert module is configured to generate alert information indicating that the batch has failed quality assurance when the thermal and temporal stress of the component exceeds a predetermined thermal-temporal stress threshold.

According to a twelfth aspect of the present invention, a method of quality assurance of a quantitative physiological sample test system performed without running a quality control sample includes the steps of: monitoring thermal and temporal stress of a component used with the test system, wherein the component is associated with a batch of substantially similar components; and generating alert information indicating that the batch has failed quality assurance when the thermal and temporal stress of the component exceeds a predetermined thermal-temporal stress threshold.

According to a thirteenth aspect of the present invention, a system for performing quality assurance of a quantitative physiological sample test system without using a quality control sample includes a thermal stress monitor module. The thermal stress monitor module is configured to monitor thermal stress of a component used with the test system. The system includes a temporal stress monitor module in communication with the thermal stress monitor module. The temporal stress monitor module is configured to monitor temporal stress of the component used with the test system. The system includes a quality assurance failure alert module in communication with the thermal stress monitor module and the temporal stress monitor module. The quality assurance failure alert module is configured to generate alert information that the component has failed quality assurance when the thermal and temporal stress exceed a predetermined thermal-temporal stress threshold.

According to a fourteenth aspect of the present invention, a system for performing quality assurance of a quantitative physiological sample test system without using a quality control sample including means for monitoring thermal and temporal stress. The thermal and temporal stress monitoring means is configured to monitor thermal and temporal stress of a component used with the test system. The system includes means for alerting quality assurance failures in communication with the thermal and temporal stress monitoring means. The quality assurance failure alerting means is configured to generate alert information indicating that the component has failed quality assurance when the thermal and temporal stress exceeds a predetermined thermal-temporal stress threshold.

According to the fourteenth aspect, the physiological sample can comprise one of blood, plasma, serum, saliva, urine, cerebrospinal fluid, and amended forms thereof. The quality control sample can comprise a liquid control or the like. The component can be used with the test system when the thermal and temporal stress does not exceed the predetermined thermal-temporal stress threshold. The thermal and temporal stress monitoring means can be separate from the test system and in a substantially same thermal environment as the test system. Alternatively, the thermal and temporal stress monitoring means is integrated with the test system.

The thermal and temporal stress monitoring means can be configured to monitor a temperature-time indicator associated with the component. For example, the thermal and temporal stress monitoring means can comprise at least one of an electrically conductive wax, a temperature-dependent liquid crystal, a shift in baseline calibration potential of a potentiometric sensor, a liposomal release of an enzyme inhibitor, a liposomal release of an electrically conductive liquid, a liposomal release of an elevated ion concentration, a liposomal release of a molecule or ion capable of electrochemical detection, a thermistor, a thermocouple, a thermal ink, a temperature-dependent chemical reaction, a temperature-dependent color changing patch, and a temperature-dependent phase change of a material.

According to the fourteenth aspect, the component can comprise a sample testing cartridge or the like. The test system can comprise a blood analysis system or the like. The blood analysis system can comprise a portable component reader or the like. The component can comprise a blood testing cartridge or the like, such as, for example, a single-use blood testing cartridge. The blood testing cartridge can include at least one electrochemical sensor. The component can comprise a sensor or the like. For example, the sensor can comprise one of an electrochemical sensor, an optical sensor, a luminescence sensor, a fluorescence sensor, an amperometric sensor, a potentiometric sensor, a conductimetric sensor, a wave guide, an evanescence sensor, a biosensor, a surface plasmon resonance sensor, an acoustic wave sensor, and a reflectance sensor. The component can be stored in a refrigerated enclosure below a predetermined temperature. The component can be removed from the refrigerated enclosure prior to use with the test system. The component can be allowed to attain ambient temperature prior to being used with the test system. The test system can be configured to perform a test to determine an analyte. For example, the analyte can comprise one of sodium, potassium, chloride, calcium, glucose, lactate, creatinine, urea, hematocrit, prothrombin time, activated clotting time, activated partial thromboplastin time, troponin I, troponin T, creatine kinase MB, brain natriuretic peptide, NTproBNP, C-reactive protein, pO2, PCO2, and pH.

According to the fourteenth aspect, the component can be associated with a batch of substantially similar components. The quality assurance failure alerting means can be configured to generate alert information indicating that the batch has failed quality assurance when the thermal and temporal stress of the component exceeds the predetermined thermal-temporal stress threshold. The test system can be configured to perform at least one failsafe check prior to use of the component. For example, the failsafe check can comprise at least one of verification that an ambient temperature is within a predetermined range, verification that the component is not faulty, and verification that the test system is not faulty. The verification that the test system is not faulty can comprise at least one of testing electrical integrity of an electrical connector associated with the test system, and testing operational integrity of operational amplifiers associated with the test system.

According to the fourteenth aspect, the test system can include means for electronically simulating. The means for electronically simulating can be configured to simulate signals produced by the component. The means for electronically simulating can be configured to generate simulation signals for testing at least one of electrical integrity of an electrical connector associated with the test system and operational integrity of operational amplifiers associated with the test system. The test system can include means for displaying. The displaying means can be configured to display alerts in accordance with the alert information. The test system can be configured to suppress display of test results when the component has failed quality assurance. The system can include means for logging in communication with the quality assurance failure alerting means. The logging means can be configured to maintain a log of the thermal and temporal stress of a plurality of components. The predetermined thermal-temporal stress threshold can be generated in accordance with a total allowable error of the test system. The predetermined thermal-temporal stress threshold can comprise a plurality of combinations of thermal stress and temporal stress. The predetermined thermal-temporal stress threshold can comprise a predetermined temperature-time profile.

According to a fifteenth aspect of the present invention, a system for evaluating thermal and temporal stress quality assurance of a quantitative electrochemical physiological sample test system includes a first means for electrochemical sensing and a second means for electrochemical sensing. The first and second electrochemical sensing means are contacted with a calibrant fluid. The first electrochemical sensing means is configured to determine a first calibration voltage associated with the concentration of a first analyte in the calibrant fluid in accordance with a first check threshold. The second electrochemical sensing means is configured to determine a second calibration voltage associated with the concentration of a second analyte in the calibrant fluid in accordance with a second check threshold. The test system is disqualified from performing a physiological sample test when both the first and second check thresholds are exceeded. For example, the first electrochemical sensing means can comprise a sodium ion-selective electrode, and the second electrochemical sensing means can comprise a calcium ion-selective electrode.

According to a sixteenth aspect of the present invention, a system for thermal and temporal stress quality assurance of a quantitative electrochemical physiological sample test system includes a plurality of means for electrochemical sensing. The plurality of electrochemical sensing means are contacted with a calibrant fluid. The system includes means for calibrating in communication with the plurality of electrochemical sensing means. The calibrating means is configured to determine a calibration parameter associated with a concentration of an analyte in the calibrant fluid for each electrochemical sensing means of a subset of the plurality of electrochemical sensing means in accordance with a predetermined check threshold. The calibrating means is configured to disqualify the test system from performing a physiological sample test when the predetermined check threshold is exceeded for each electrochemical sensing means of the subset.

According to the sixteenth aspect, the subset of electrochemical sensing means can comprise a calcium ion-selective electrode and a BUN electrode. Alternatively, the subset of electrochemical sensing means can comprise a sodium ion-selective electrode, a calcium ion-selective electrode, and a BUN electrode. The calibration parameter can comprise a calibration voltage. In the alternative, the calibration parameter can comprise a calibration voltage drift rate. Alternatively, the calibration parameter can comprise a combination of a calibration voltage and a calibration voltage drift rate. Each of the plurality of electrochemical sensing means can comprise, for example, one of a sodium sensor, a potassium sensor, a chloride sensor, a pH sensor, a pO2 sensor, a pCO2 sensor, a lactate sensor, a glucose sensor, a creatinine sensor, a BUN electrode, a calcium sensor, a magnesium sensor, and a hematocrit sensor.

According to a seventeenth aspect of the present invention, a system for performing quality assurance of a quantitative physiological sample test system without using a quality control sample comprises means for monitoring thermal stress. The thermal stress monitoring means is configured to monitor thermal stress of a component used with the test system. The system includes means for monitoring temporal stress in communication with the thermal stress monitoring means. The temporal stress monitoring means is configured to monitor temporal stress of the component used with the test system. The system includes a means for alerting quality assurance failures in communication with the thermal stress monitoring means and the temporal stress monitoring means. The quality assurance failure alerting means is configured to generate alert information that the component has failed quality assurance when the thermal and temporal stress exceed a predetermined thermal-temporal stress threshold.

BRIEF DESCRIPTION OF THE DRAWINGS

Other objects and advantages of the present invention will become apparent to those skilled in the art upon reading the following detailed description of preferred embodiments, in conjunction with the accompanying drawings, wherein like reference numerals have been used to designate like elements, and wherein.

FIG. 8 illustrates (A) a table for ATE acceptance criteria, (B) an LER (limits for erroneous results) acceptance criteria table for electrolytes, glucose and hematocrit tests, and (C) LER acceptance criteria table for blood urea nitrogen and creatinine tests, in accordance with an exemplary embodiment of the present invention.

FIG. 9 illustrates the expected mean values and ranges for sodium, potassium, calcium, total CO2, glucose, creatinine, chloride and urea controls ((A) Level 1 and (B) Level 3) used with an i-STAT CHEM8+ cartridge that performs these blood tests, in accordance with an exemplary embodiment of the present invention.

FIG. 10 illustrates the expected mean values and ranges for hematocrit controls ((A) Level 1 (B) Level 3) used with an i-STAT CHEM8+ cartridge that tests for hematocrit among a number of other blood tests, in accordance with an exemplary embodiment of the present invention.

Figure 11:
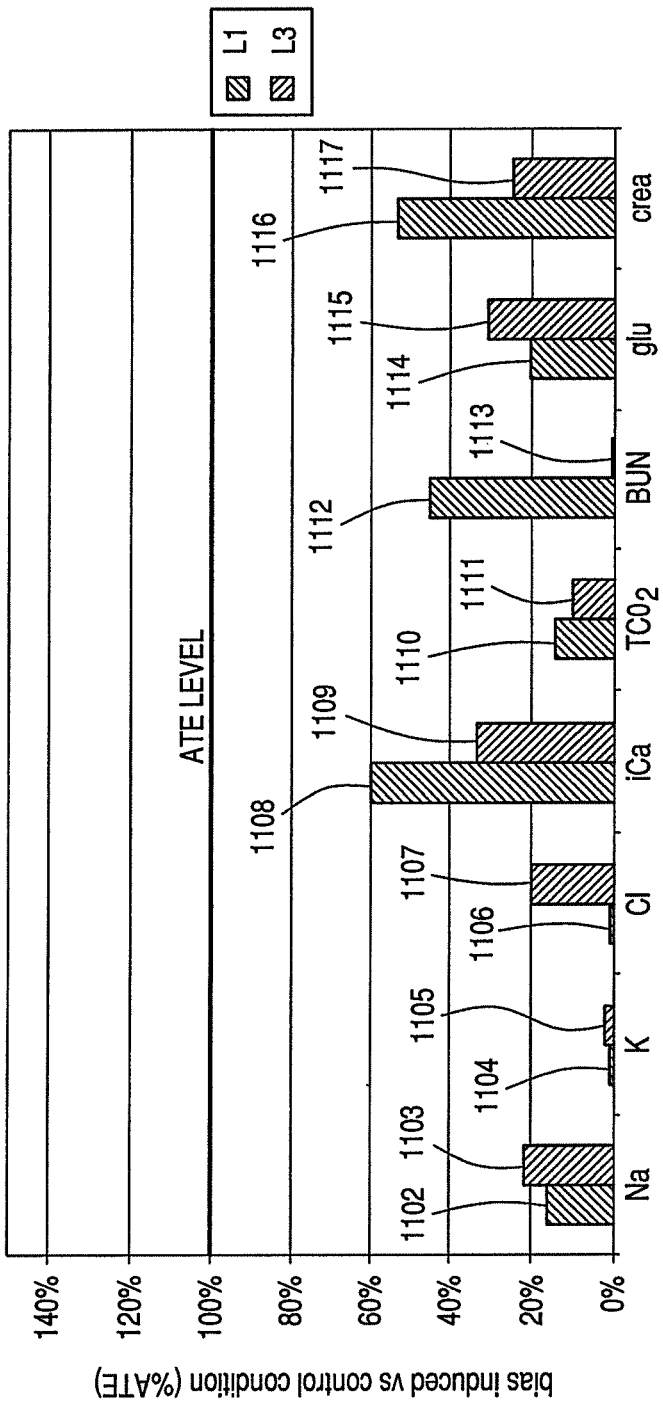

FIG. 11 illustrates the stability beyond labeled conditions, two weeks beyond the printed expiration date at 35° C., for an i-STAT CHEM8+ cartridge containing sensors for sodium, potassium, chloride, calcium, glucose, total carbon dioxide, blood urea nitrogen, creatinine and hematocrit, in accordance with an exemplary embodiment of the present invention. The change in induced bias versus the control condition ATE is plotted for each test.

Figure 12:
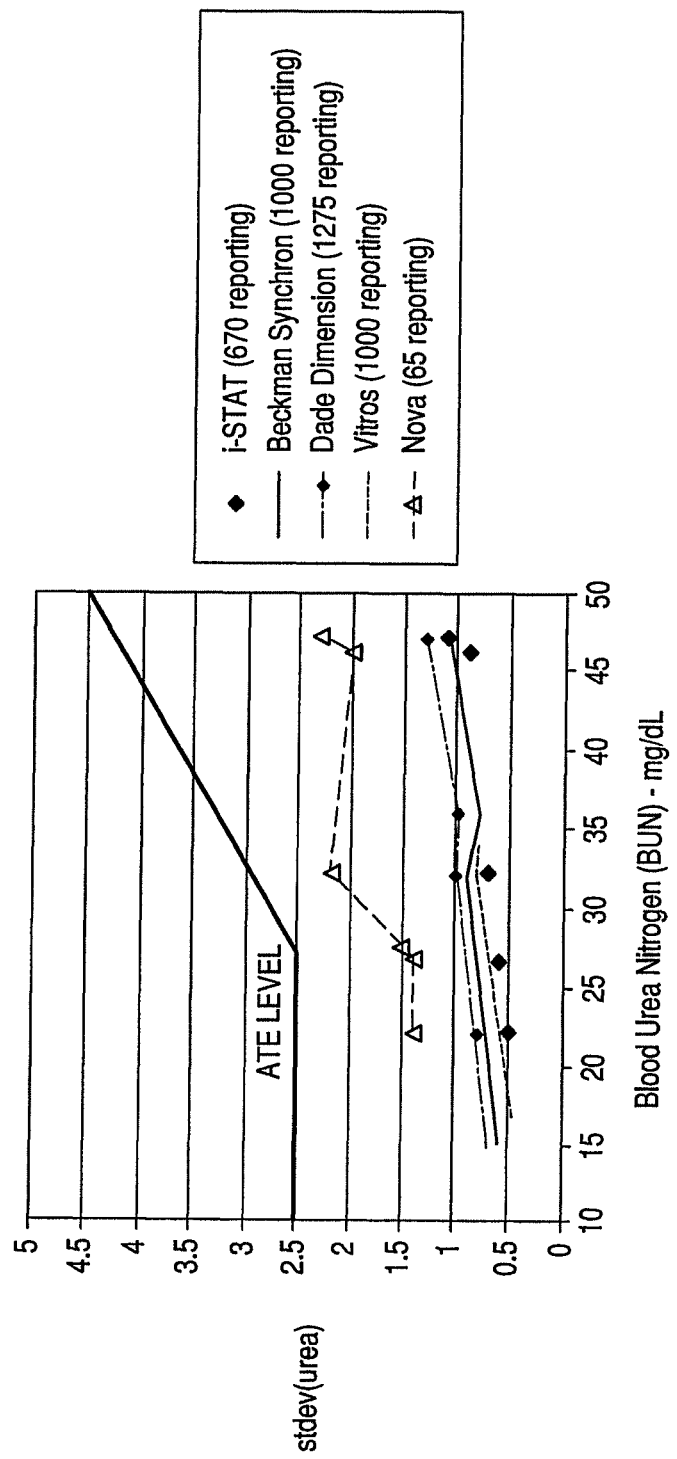

FIG. 12 is a graphical representation illustrating a College of American Pathologists survey for various instrument manufacturers and i-STAT for the standard deviation of a blood urea nitrogen test over the clinical range against ATE, in accordance with an exemplary embodiment of the present invention.

Figure 13:
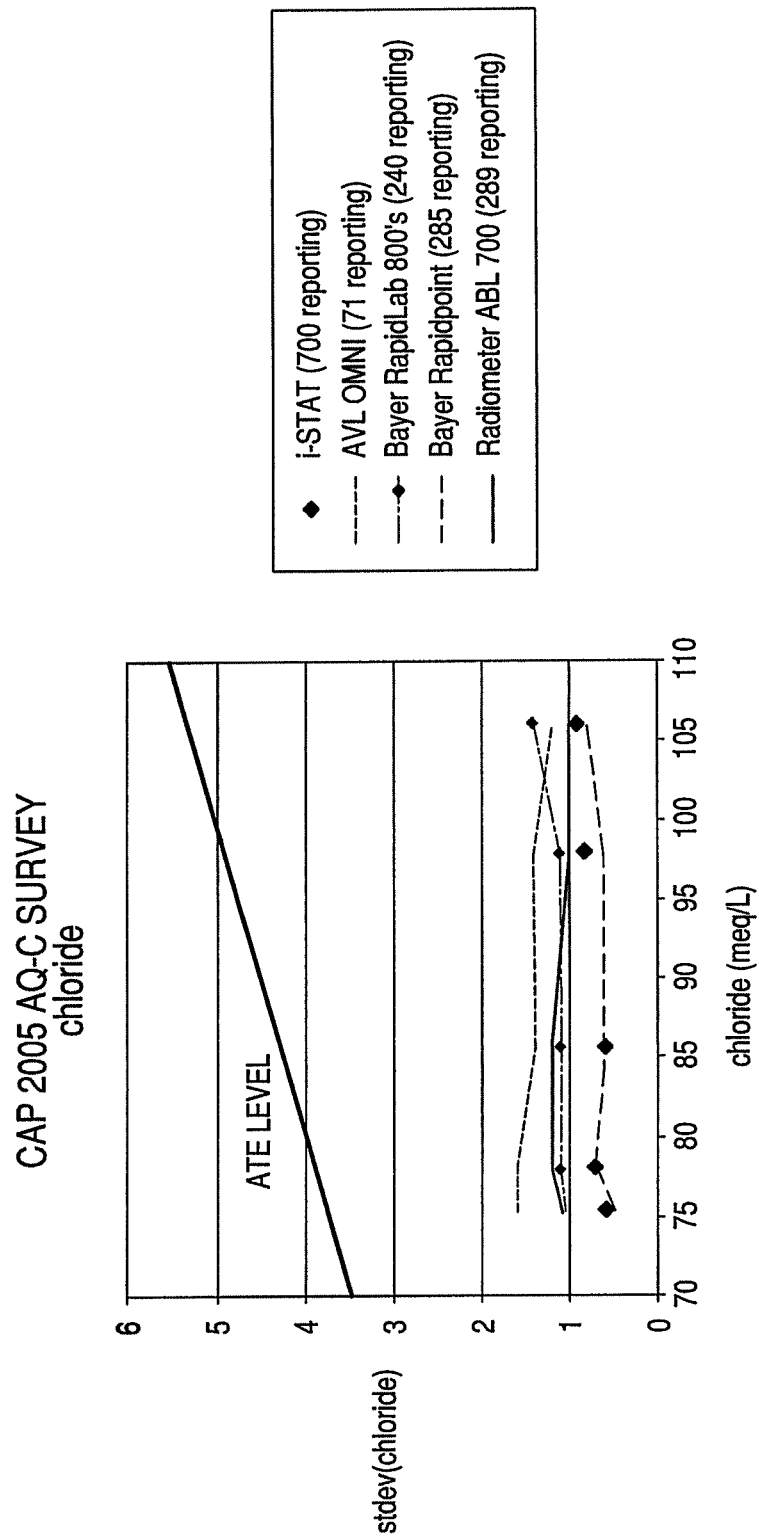

FIG. 13 is a graphical representation illustrating a College of American Pathologists survey for various instrument manufacturers and i-STAT for the standard deviation of a chloride test over the clinical range against ATE, in accordance with an exemplary embodiment of the present invention.

Figure 14:
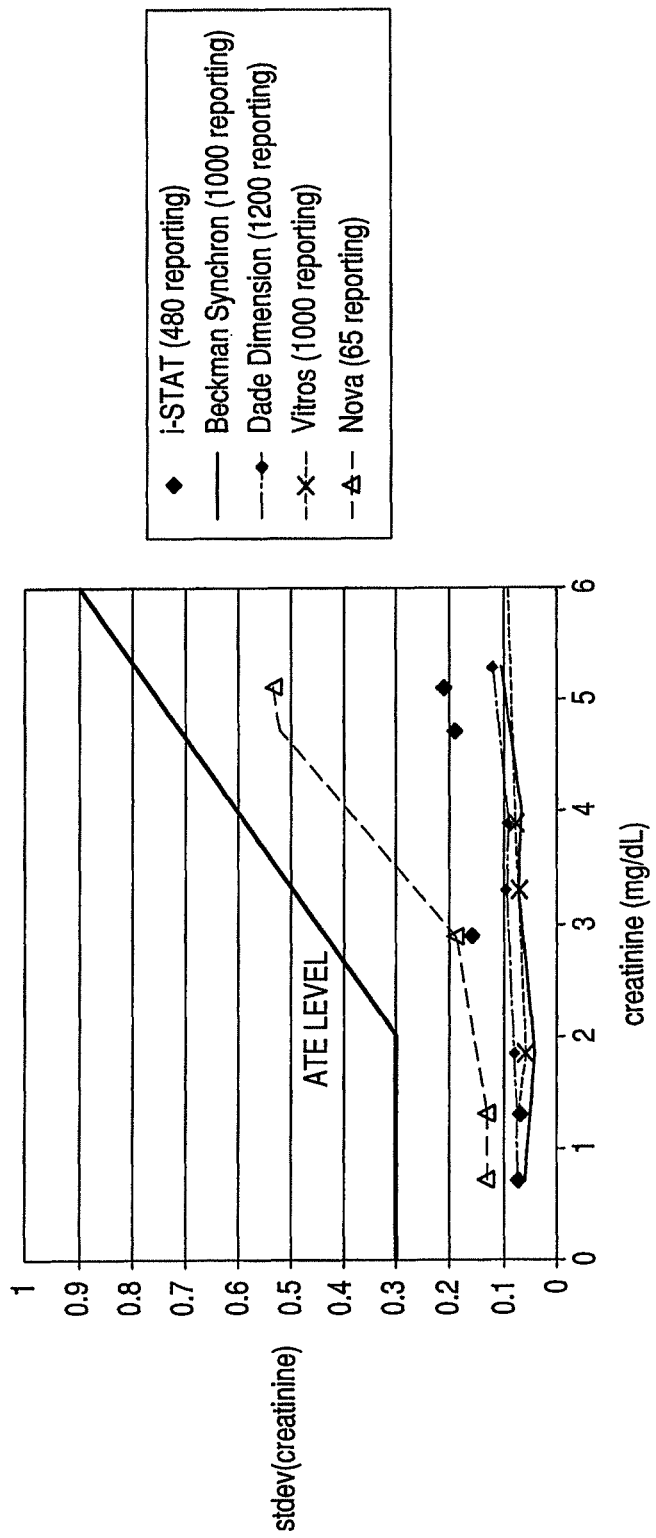

FIG. 14 is a graphical representation illustrating a College of American Pathologists survey for various instrument manufacturers and i-STAT for the standard deviation of a creatinine test over the clinical range against ATE, in accordance with an exemplary embodiment of the present invention.

Figure 15:
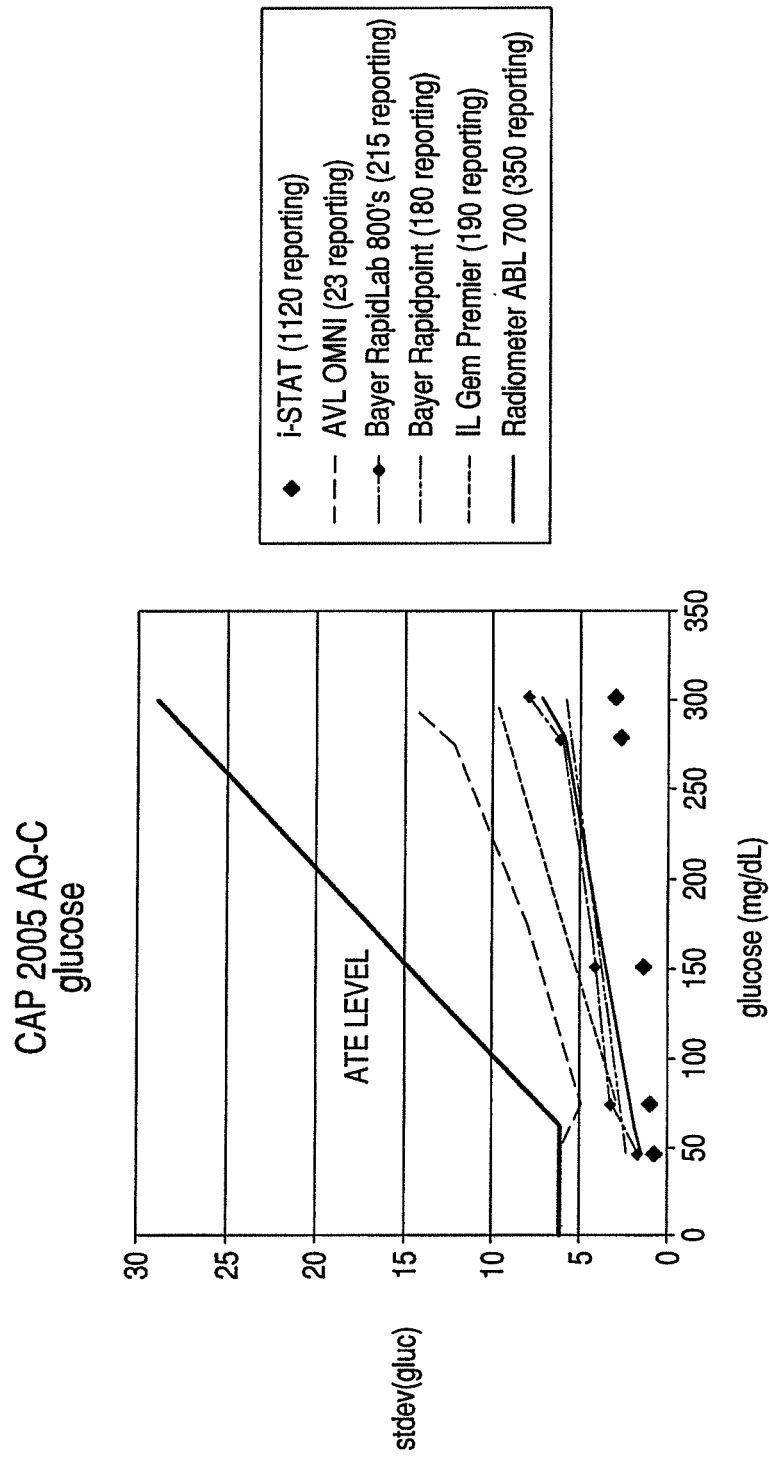

FIG. 15 is a graphical representation illustrating a College of American Pathologists survey for various instrument manufacturers and i-STAT for the standard deviation of a glucose test over the clinical range against ATE, in accordance with an exemplary embodiment of the present invention.

Figure 16:
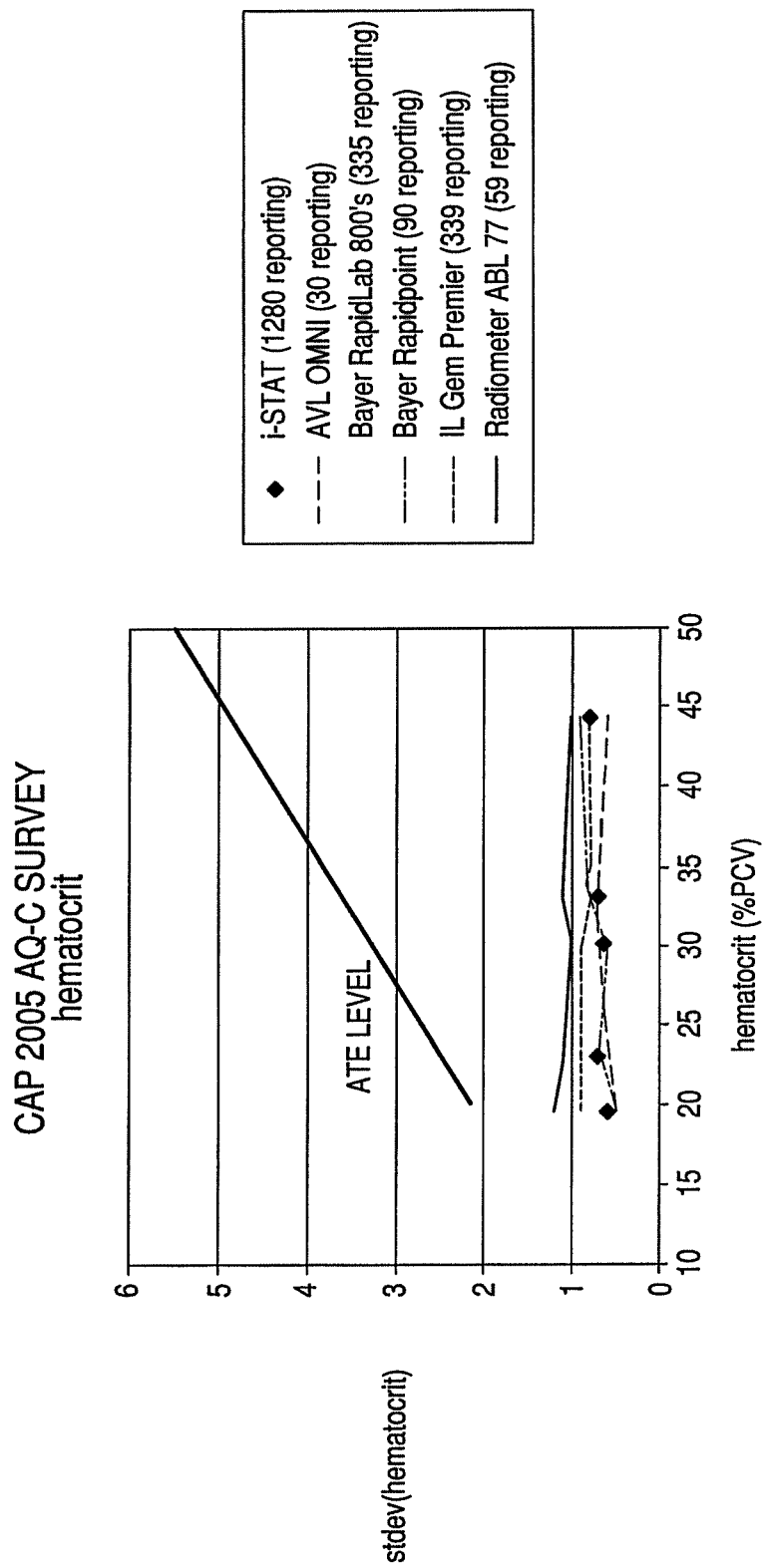

FIG. 16 is a graphical representation illustrating a College of American Pathologists survey for various instrument manufacturers and i-STAT for the standard deviation of a hematocrit test over the clinical range against ATE, in accordance with an exemplary embodiment of the present invention.

Figure 17:
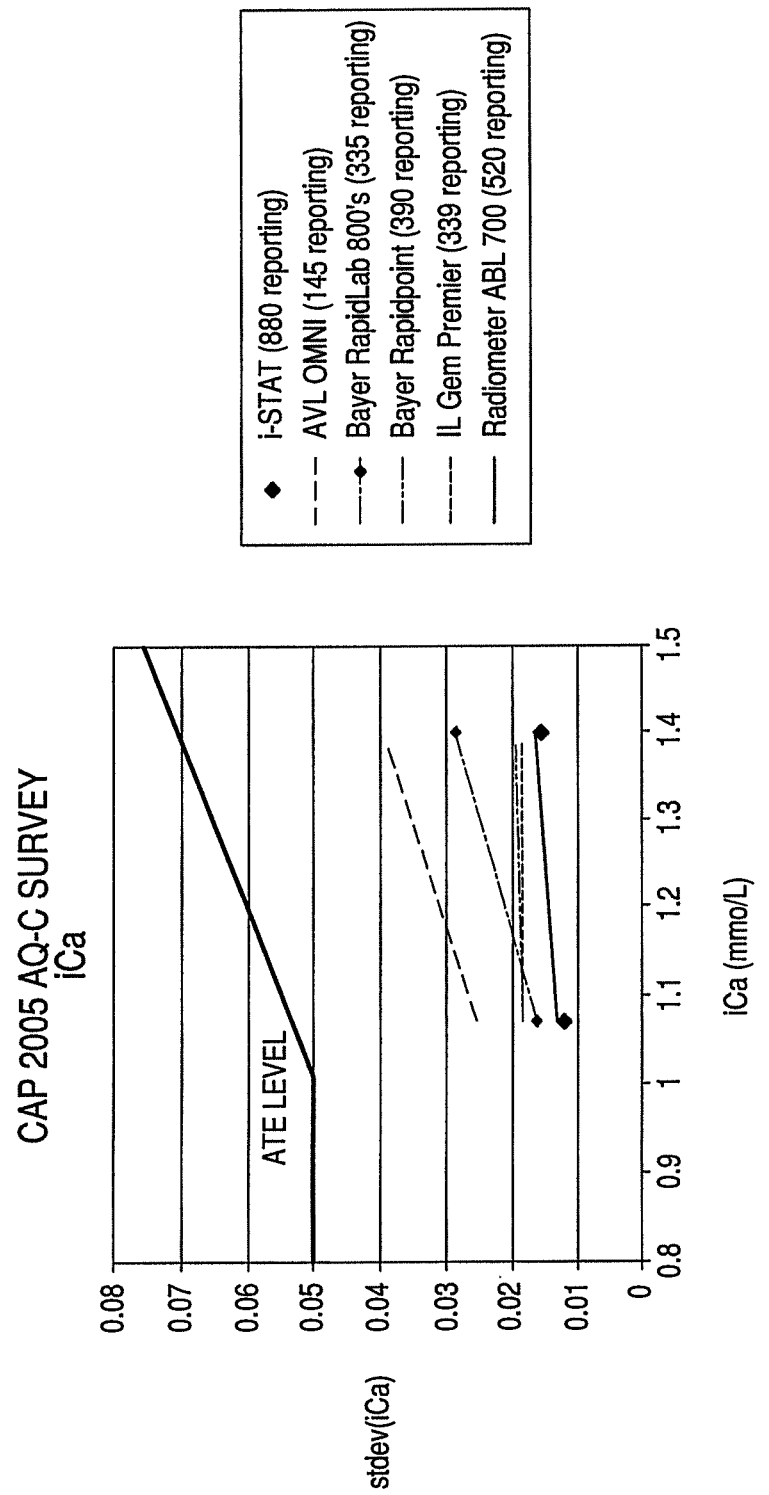

FIG. 17 is a graphical representation illustrating a College of American Pathologists survey for various instrument manufacturers and i-STAT for the standard deviation of an ionized calcium test over the clinical range against ATE, in accordance with an exemplary embodiment of the present invention.

Figure 18:
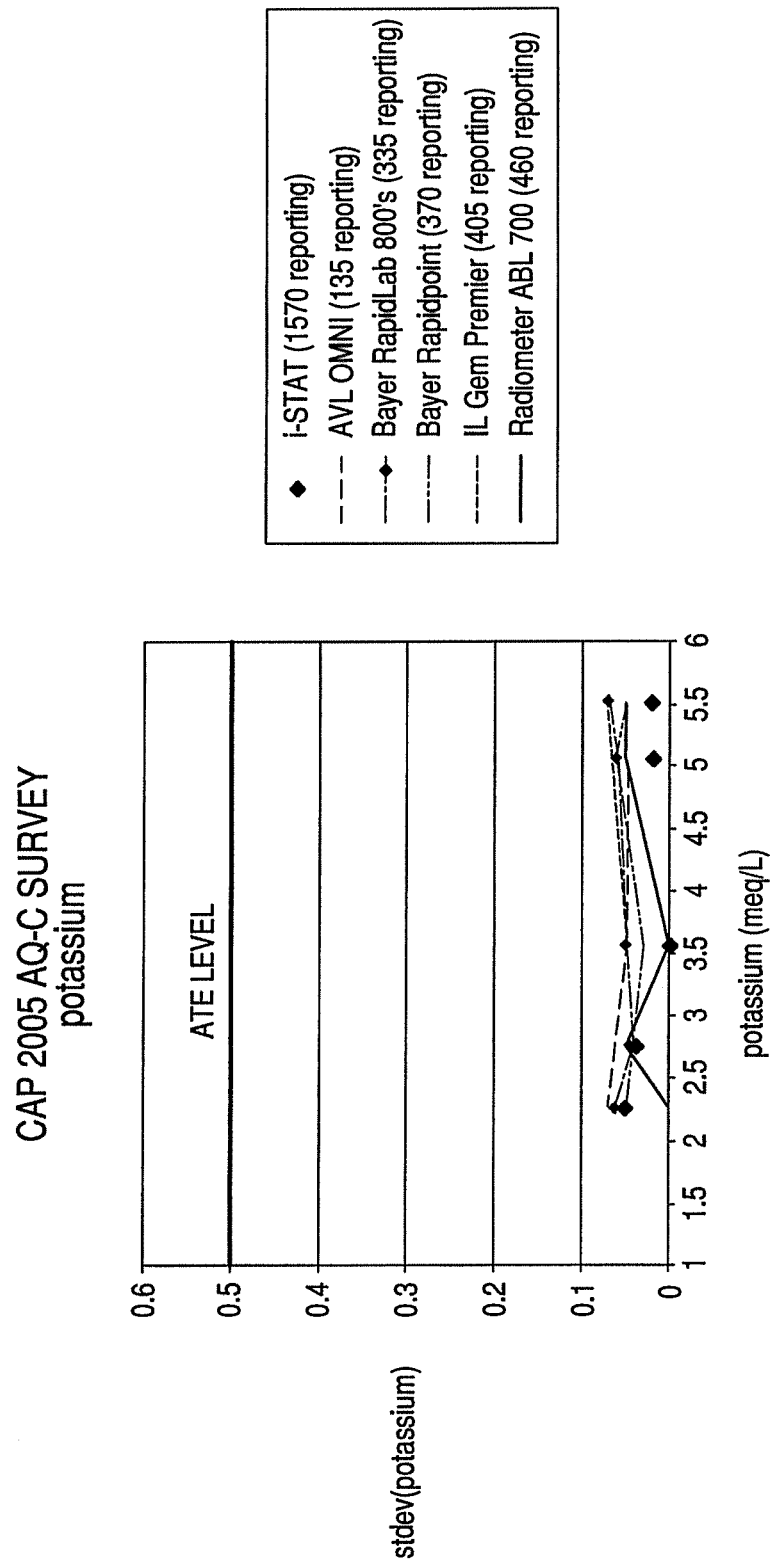

FIG. 18 is a graphical representation illustrating a College of American Pathologists survey for various instrument manufacturers and i-STAT for the standard deviation of a potassium test over the clinical range against ATE, in accordance with an exemplary embodiment of the present invention.

Figure 19:
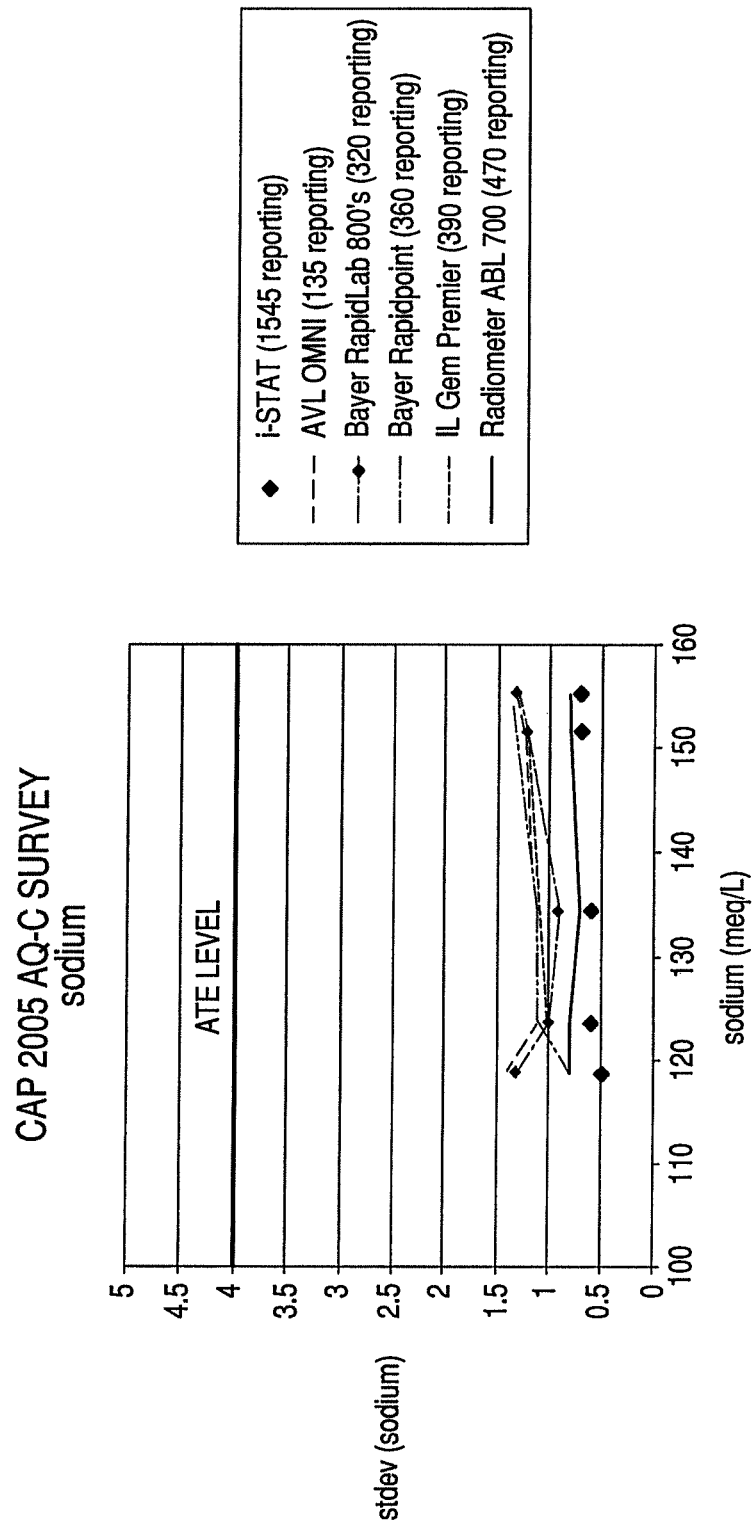

FIG. 19 is a graphical representation illustrating a College of American Pathologists survey for various instrument manufacturers and i-STAT for the standard deviation of a sodium test over the clinical range against ATE, in accordance with an exemplary embodiment of the present invention.

Figure 20:
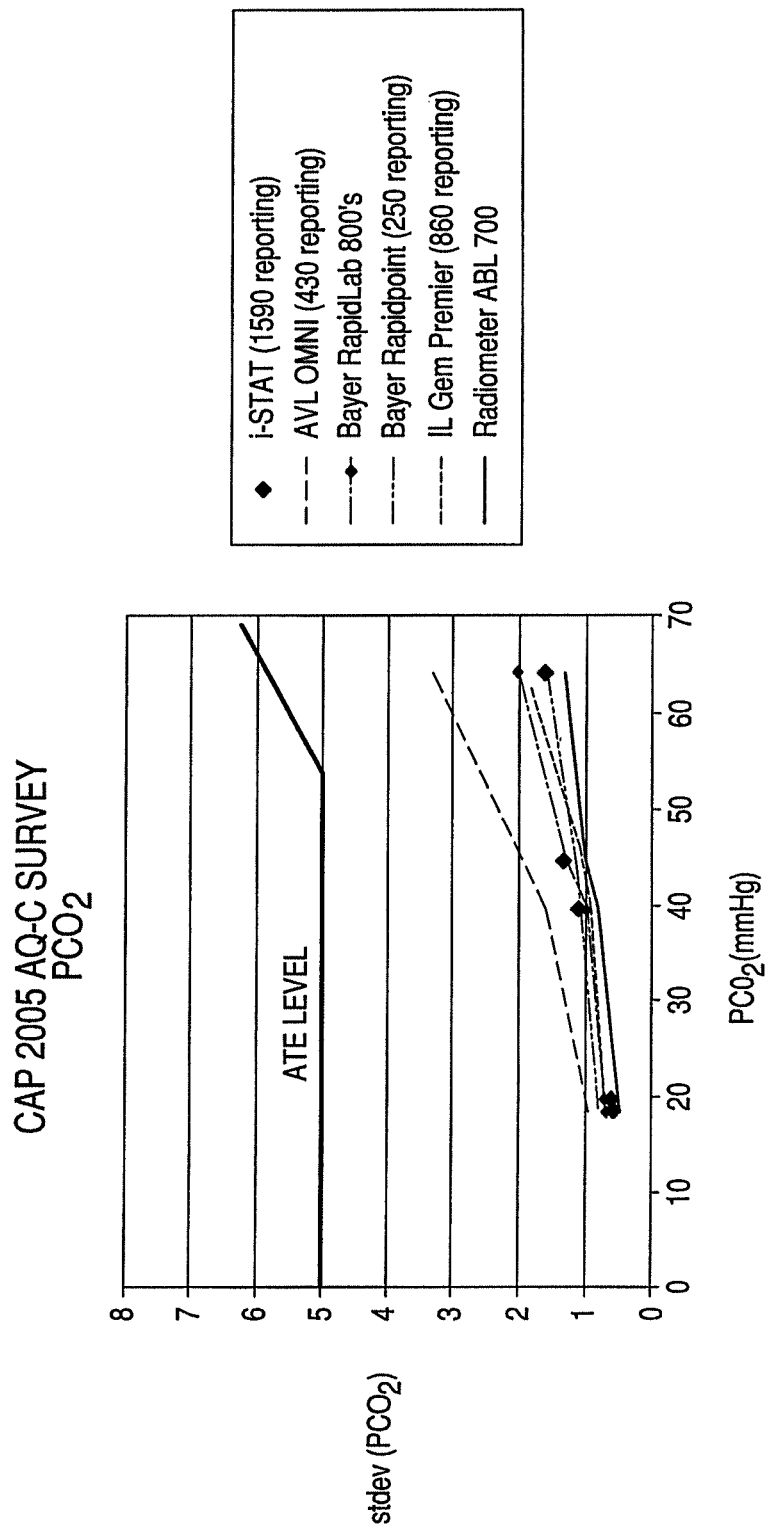

FIG. 20 is a graphical representation illustrating a College of American Pathologists survey for various instrument manufacturers and i-STAT for the standard deviation of a partial pressure of carbon dioxide (pCO2) test over the clinical range against ATE, in accordance with an exemplary embodiment of the present invention.

Figure 21:
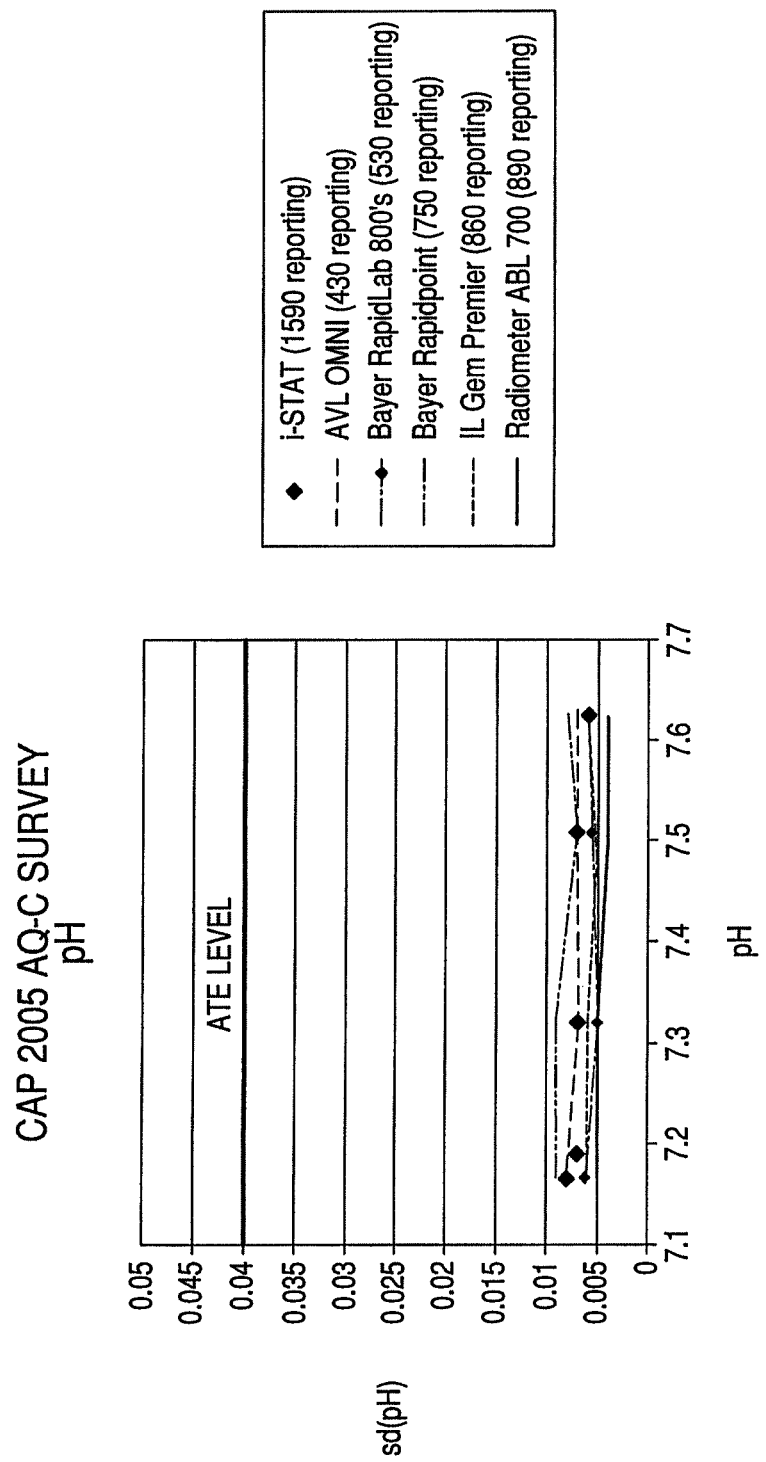

FIG. 21 is a graphical representation illustrating a College of American Pathologists survey for various instrument manufacturers and i-STAT for the standard deviation of a pH test over the clinical range against ATE, in accordance with an exemplary embodiment of the present invention.

Figure 22:
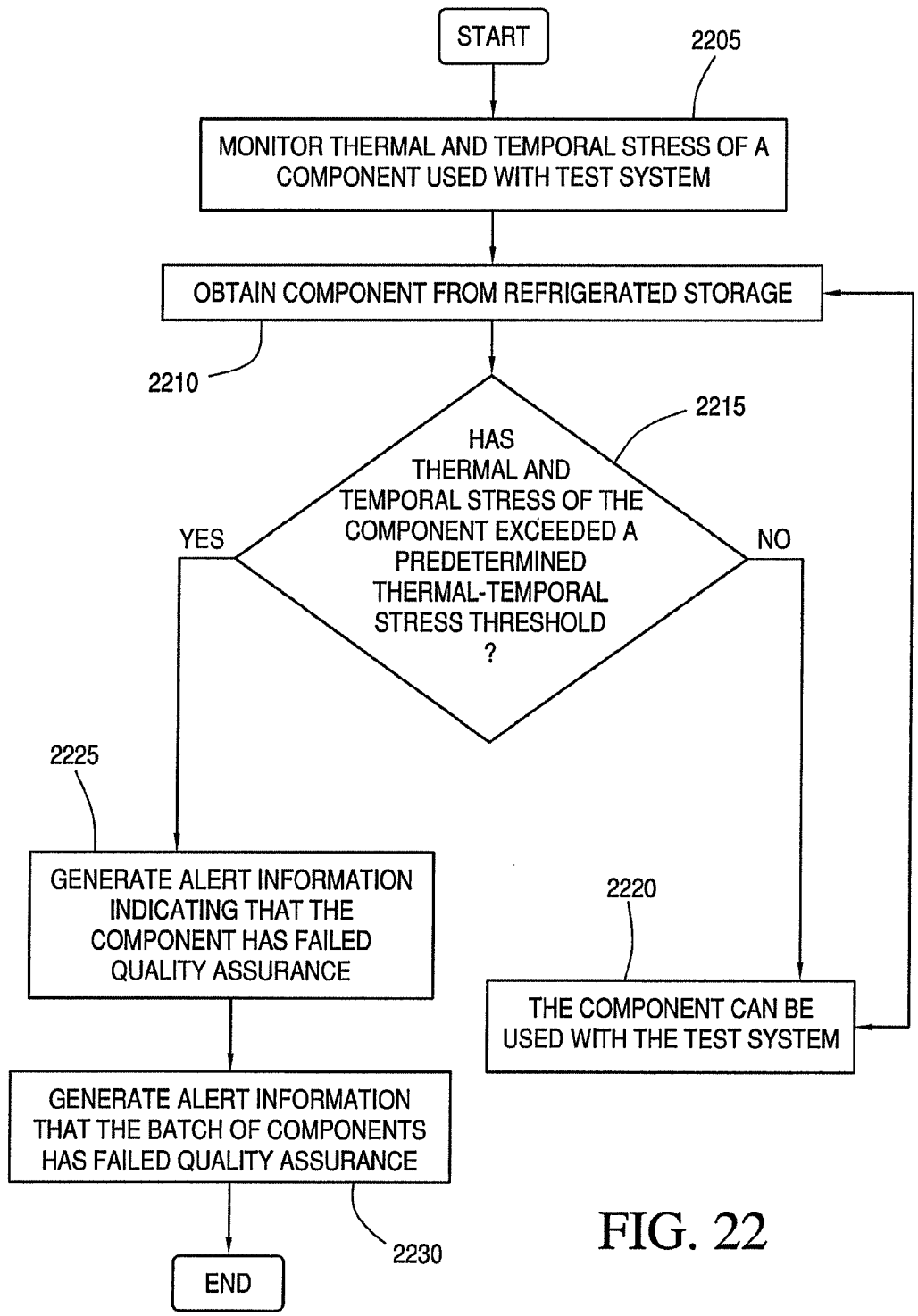

FIG. 22 is a flowchart illustrating steps for quality assurance of a quantitative physiological sample test system performed without running a quality control sample, in accordance with an exemplary embodiment of the present invention.

Figure 23:
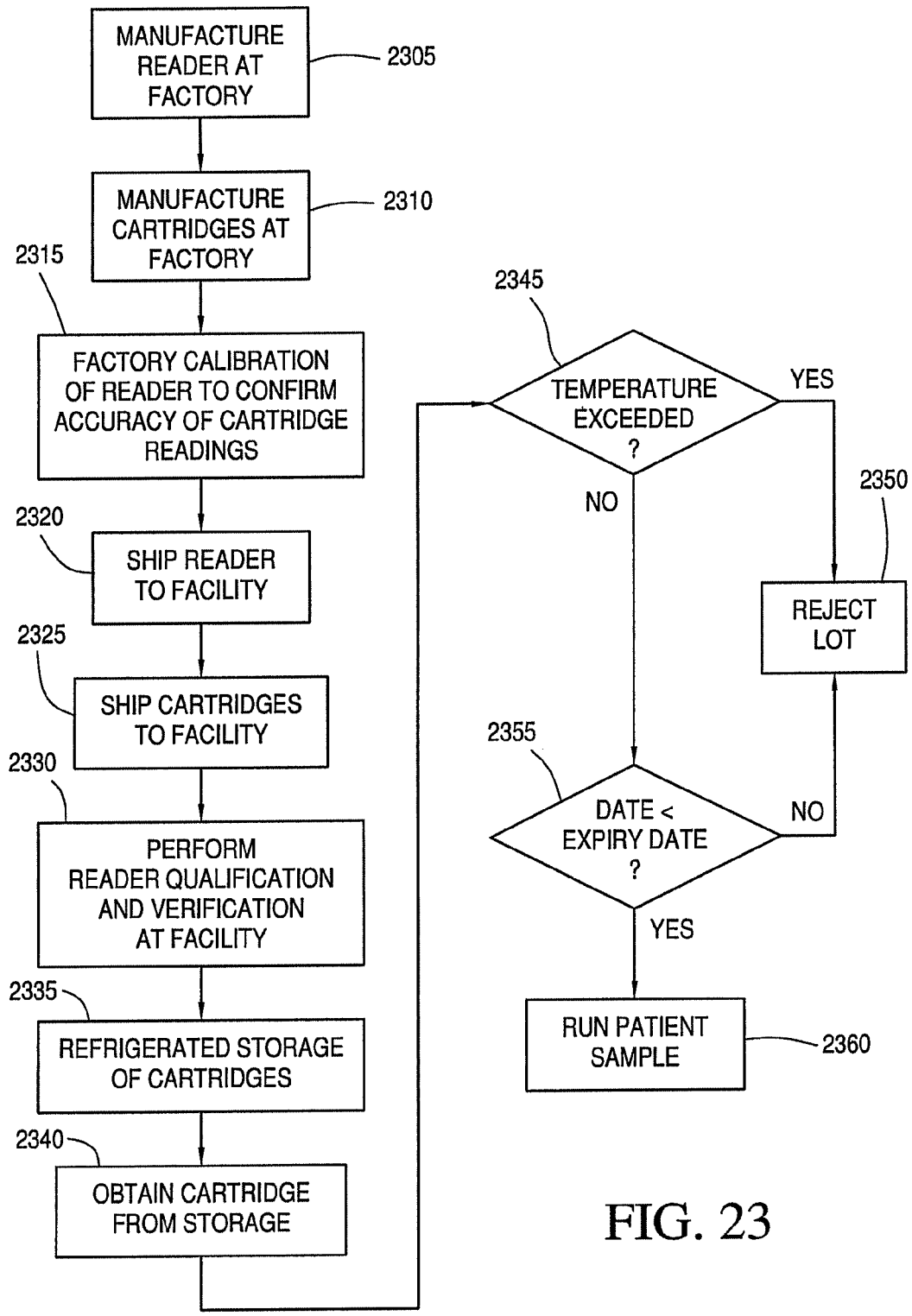

FIG. 23 is a flowchart illustrating a method of quality control based on automatic thermal and temporal monitoring without the use of control fluids, in accordance with an exemplary embodiment of the present invention.

Figure 24:
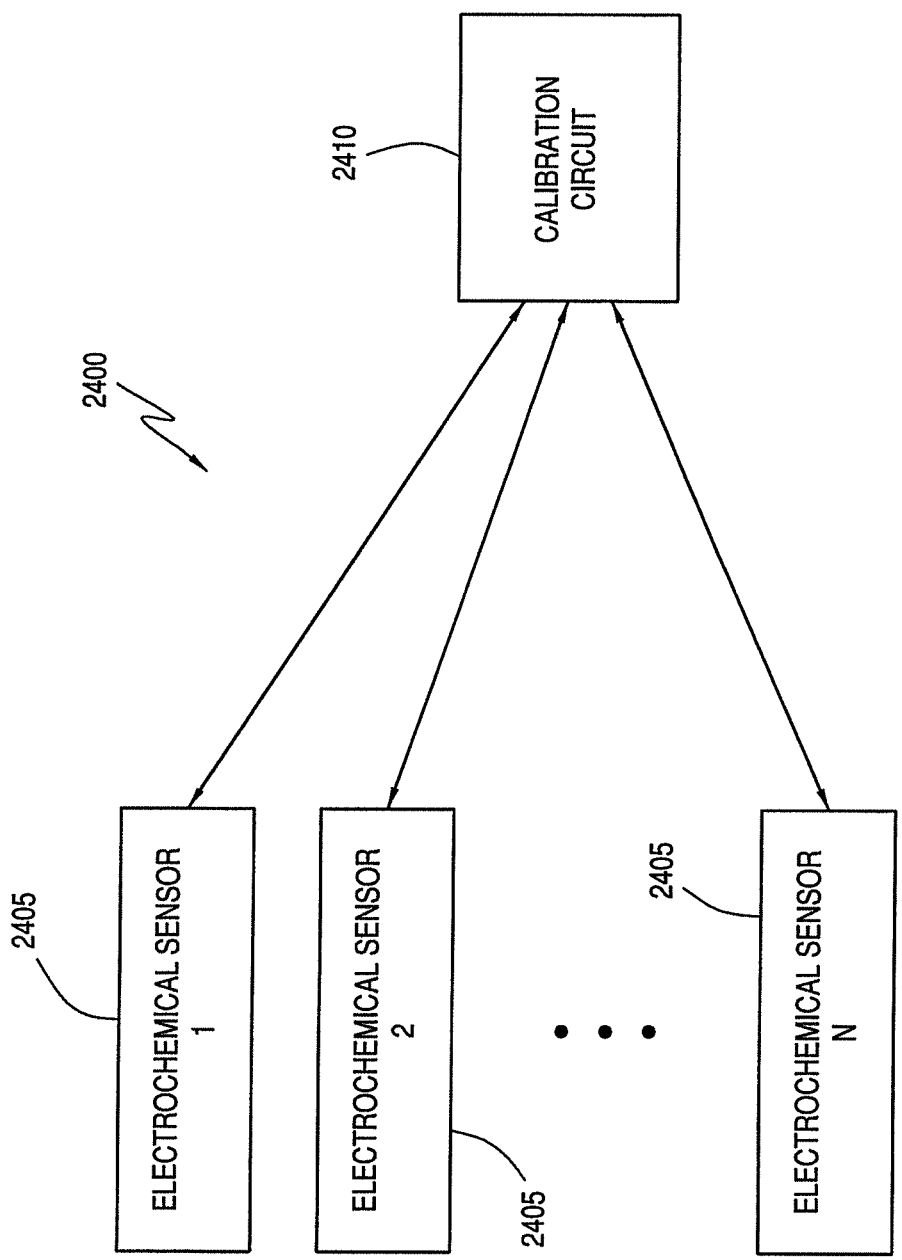

FIG. 24 is a block diagram illustrating a system for thermal and temporal stress quality assurance of a quantitative electrochemical physiological sample test system, in accordance with an alternative exemplary embodiment of the present invention.

Figure 25A:
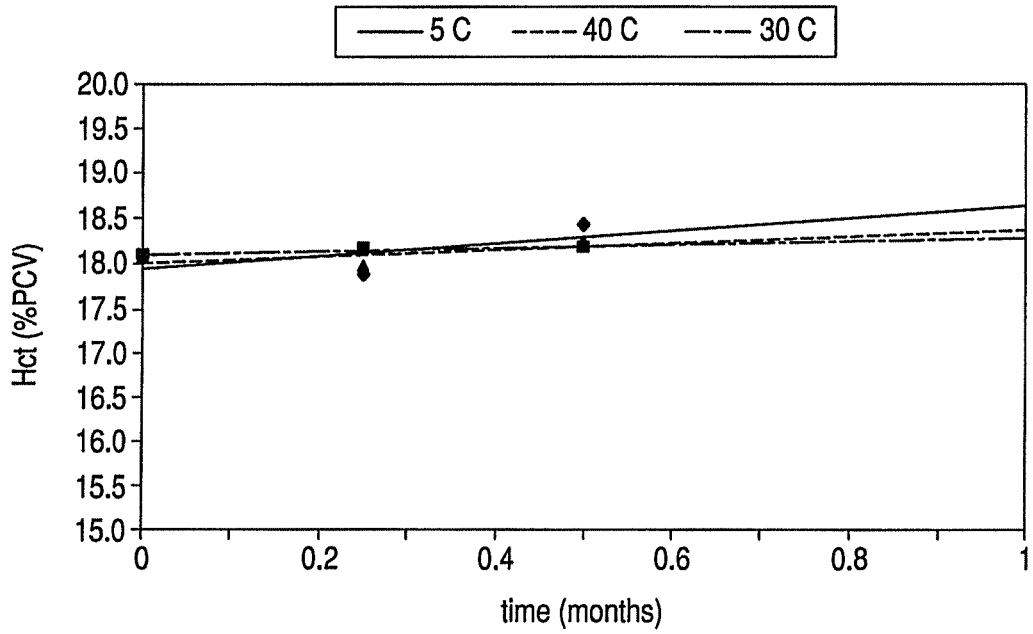
Figure 25B:
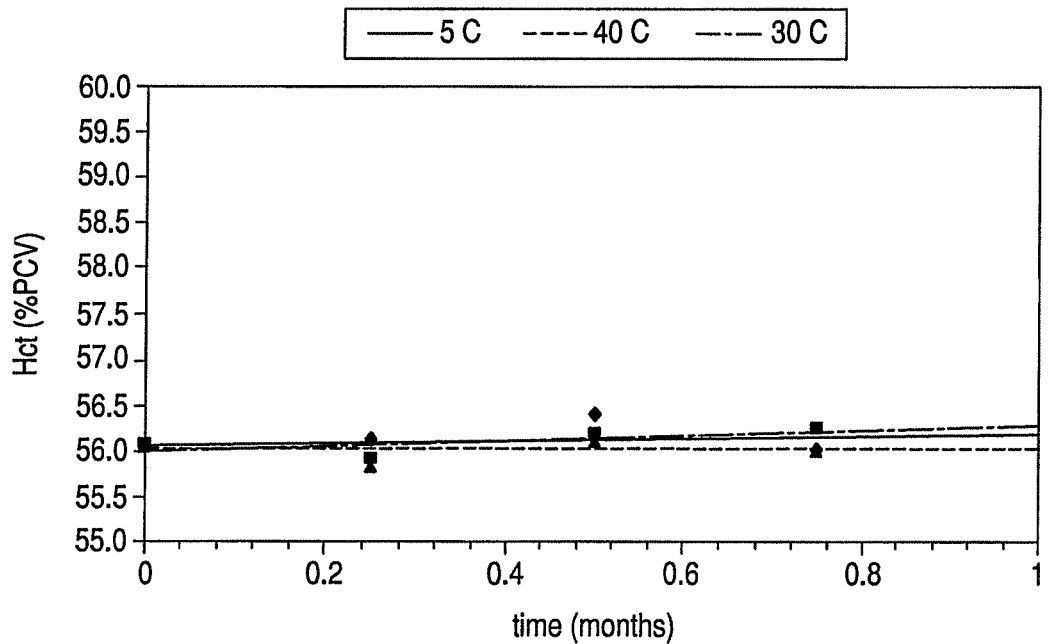

FIGS. 25(A) and 25(B) are graphical representations illustrating the behavior of the CHEM8+ hematocrit sensor under thermal stress (T=30° C. and 40° C. for 3 weeks), and compare the performance of cartridges stored at T=5° C. for the same duration, in accordance with an exemplary embodiment of the present invention. In FIGS. 25(A) and 25(B), the test fluids used are the RNA Medical hematocrit Levels L1 and L3, respectively.

Figure 26:
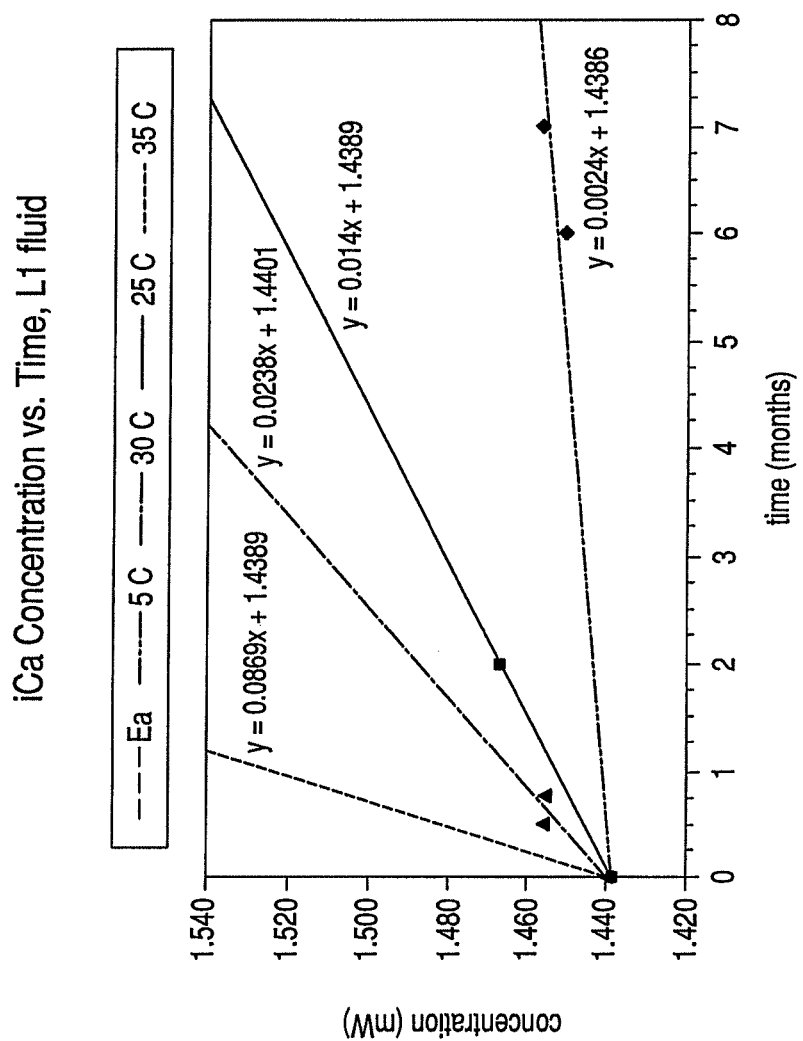

FIG. 26 is a graphical representation illustrating a plot of ionized calcium sensors in an i-STAT CHEM8+ cartridge tested with Level 1 chemistry control fluid after various storage times at 5° C., 25° C., 30° C., and 35° C., in accordance with an exemplary embodiment of the present invention.

Figure 27:
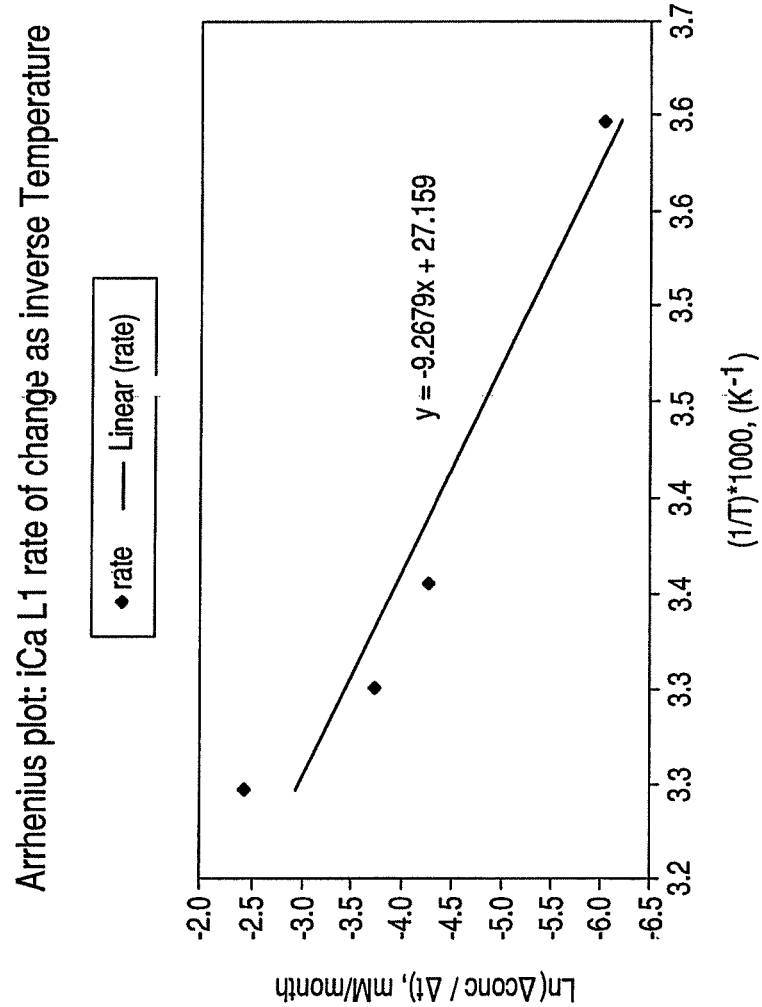

FIG. 27 is a graphical representation illustrating the data from FIG. 26 as an Arrhenius plot for ionized calcium, in accordance with an exemplary embodiment of the present invention.

Figure 28:
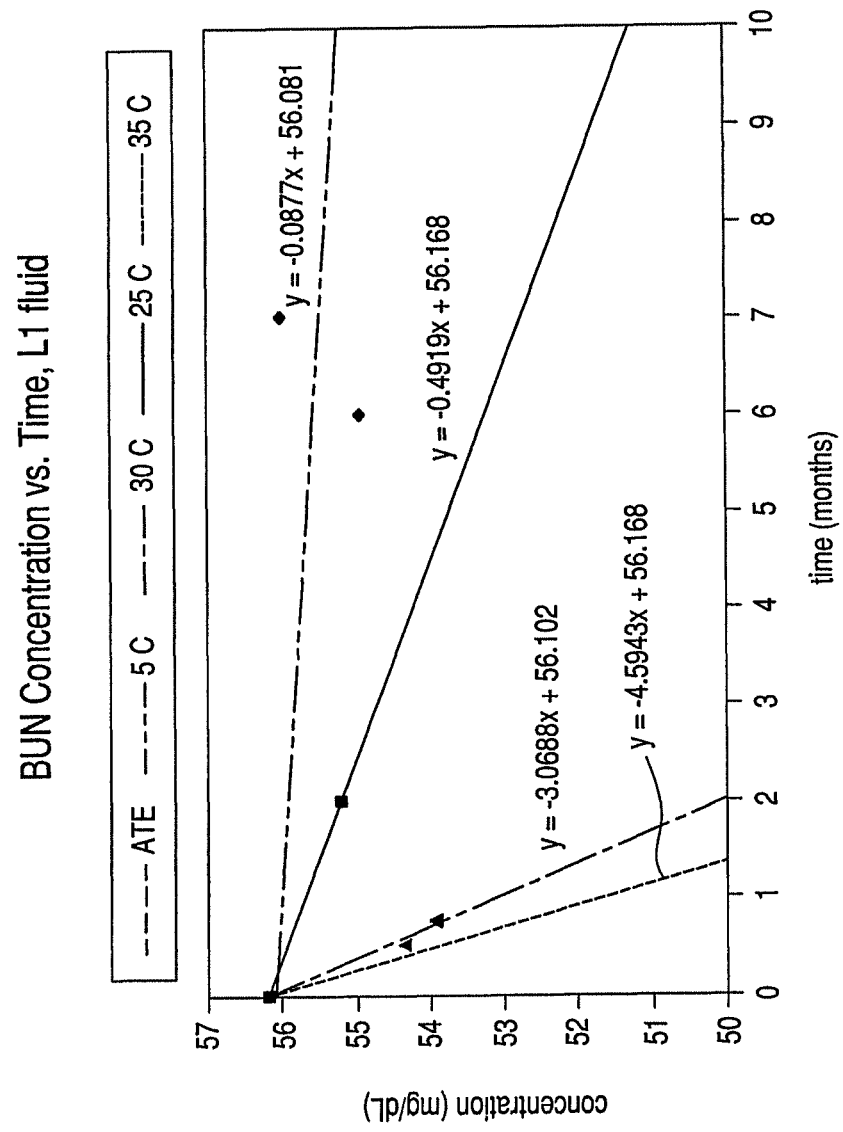

FIG. 28 is a graphical representation of a plot of blood urea nitrogen (BUN) sensors in an i-STAT CHEM8+ cartridge tested with Level 1 chemistry control fluid after various storage times at 5° C., 25° C., 30° C., and 35° C., in accordance with an exemplary embodiment of the present invention.

Figure 29:
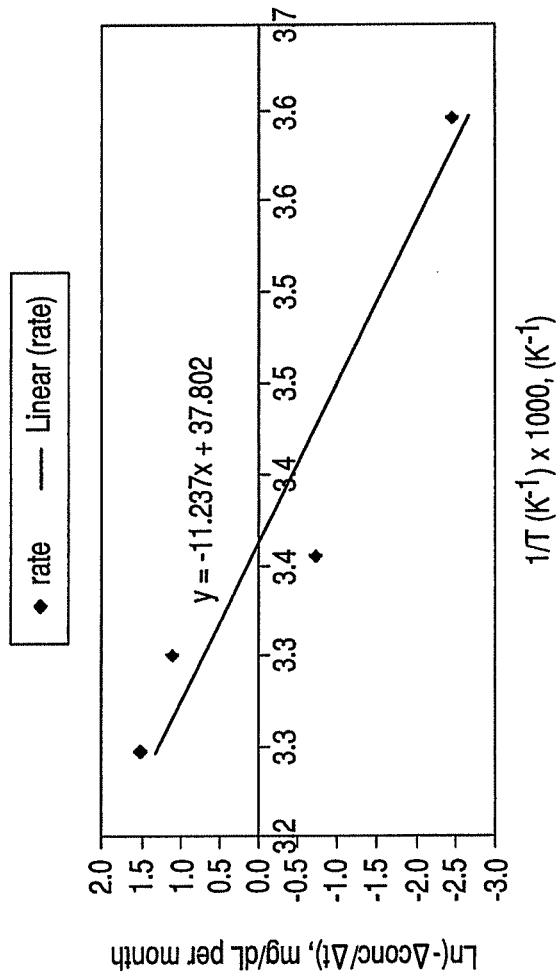

FIG. 29 is a graphical representation illustrating the data from FIG. 28 as an Arrhenius plot for BUN, in accordance with an exemplary embodiment of the present invention.

Figure 30:
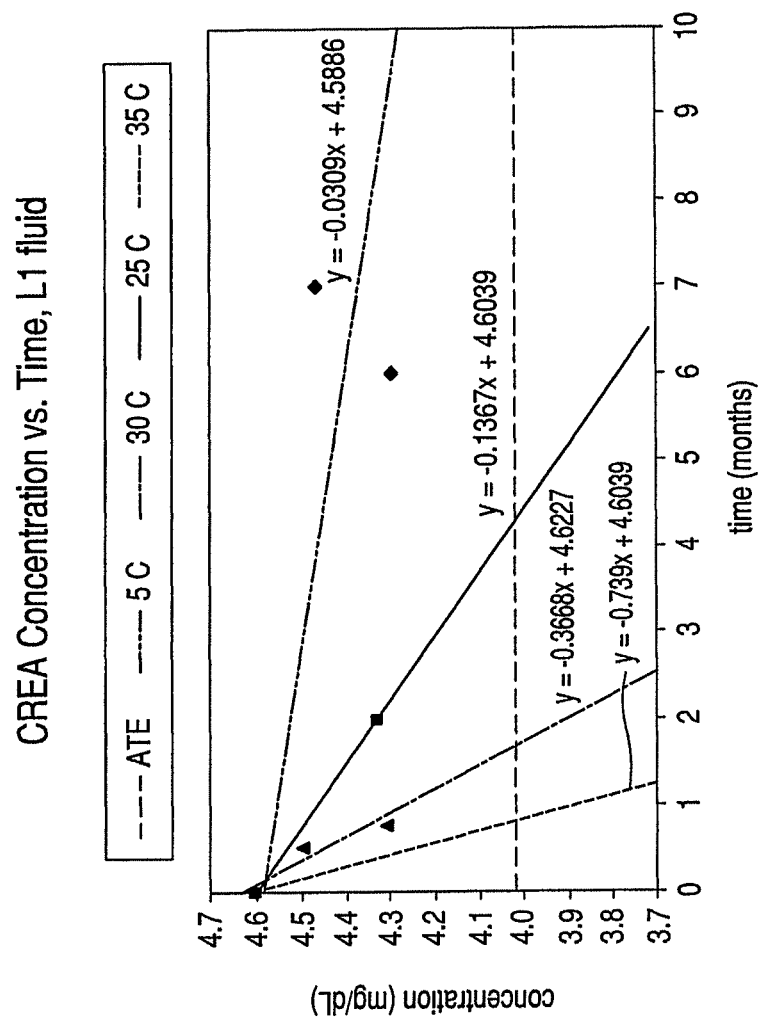

FIG. 30 is a graphical representation illustrating a plot of creatinine sensors in an i-STAT CHEM8+ cartridge tested with Level 1 chemistry control fluid after various storage times at 5° C., 25° C., 30° C., and 35° C., in accordance with an exemplary embodiment of the present invention.

Figure 31:
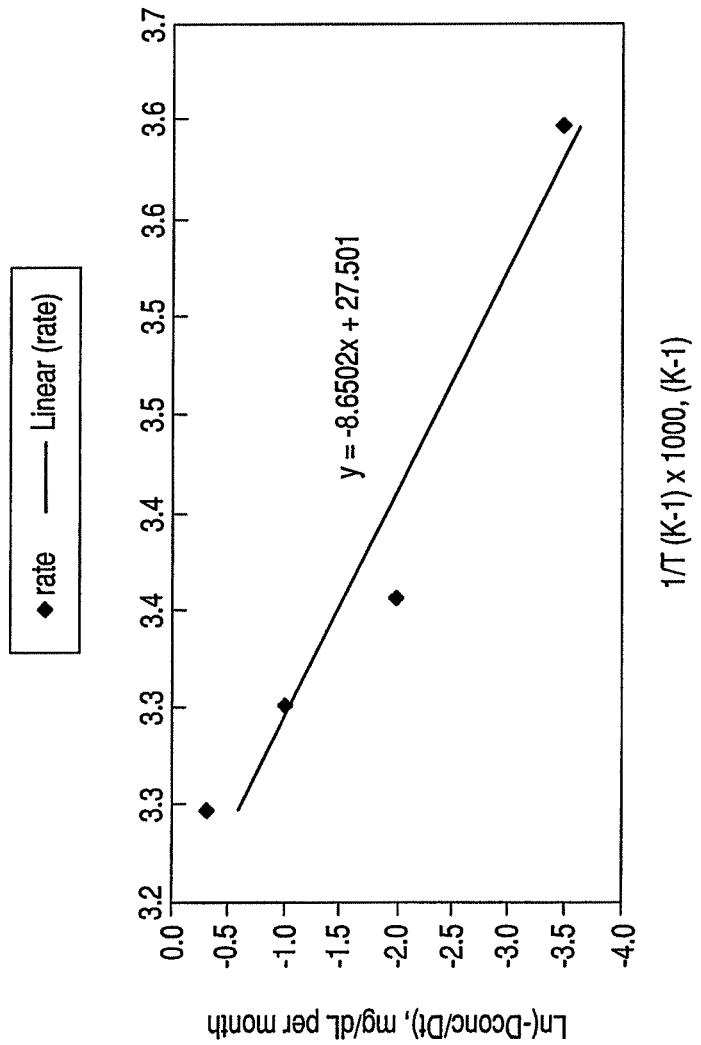

FIG. 31 is a graphical representation illustrating the data from FIG. 30 as an Arrhenius plot for creatinine, in accordance with an exemplary embodiment of the present invention.

FIG. 32 is a graphical representation illustrating summary data of ATE for control fluids Levels 1 and 3, in accordance with an exemplary embodiment of the present invention.

FIG. 33 illustrates a package insert layout for presenting all of the analyte targets available from the L1 fluid for Na, K, Cl, iCa, glucose, creatinine, BUN and TCO2, in accordance with an exemplary embodiment of the present invention.

Figure 34:
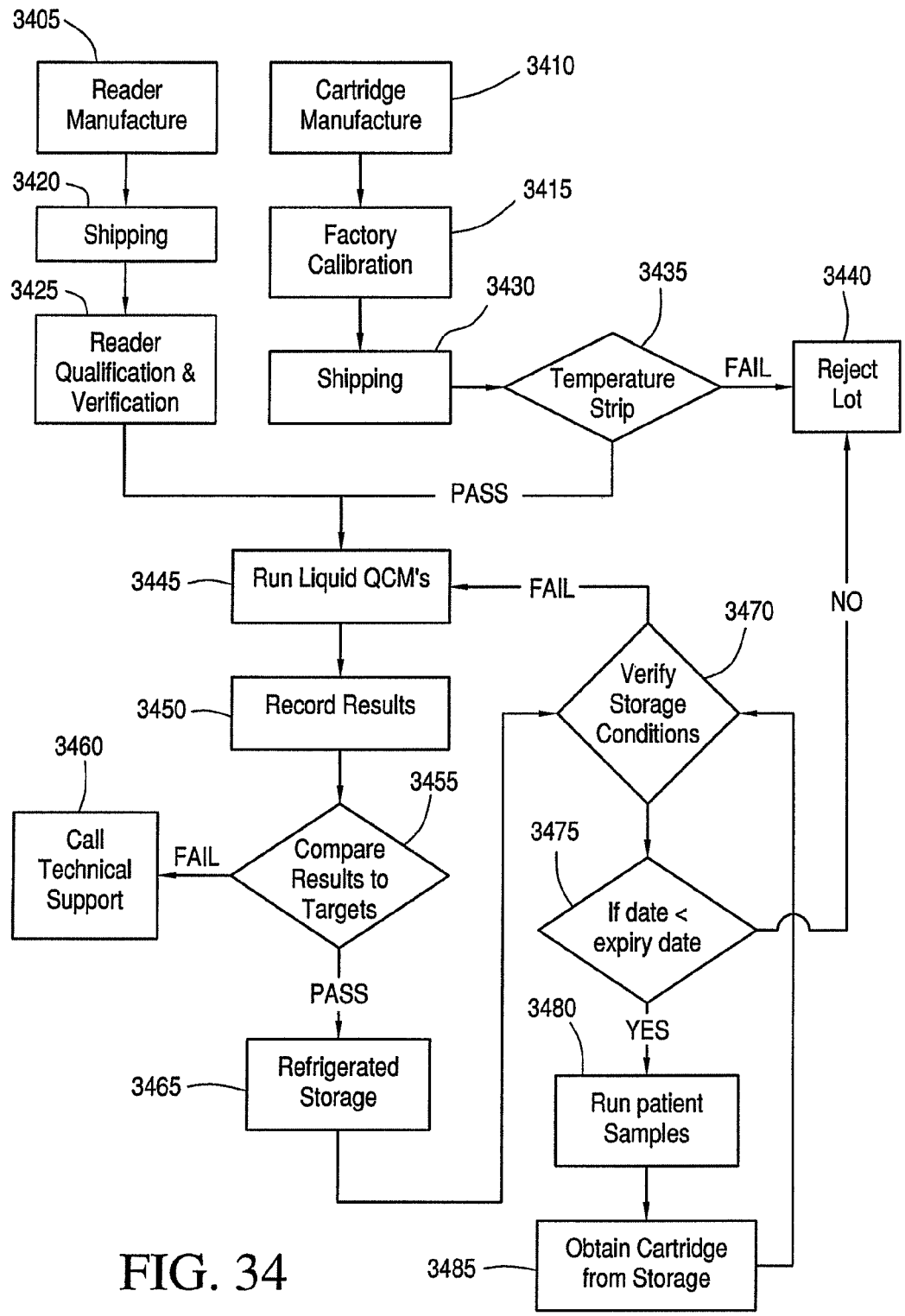

FIG. 34 illustrates an operational flow diagram for a method of quality control based on thermal and temporal monitoring using a single control fluid or a limited combination thereof, in accordance with an exemplary embodiment of the present invention.

DETAILED DESCRIPTION OF THE PREFERRED EMBODIMENTS

Exemplary embodiments of the present invention are directed to an improved quality assurance system and method for point-of-care testing. According to an exemplary embodiment, the present invention can provide quality assurance for laboratory quality tests performed by a blood analysis system or the like at the point of patient care without the need for running liquid-based quality control materials on the analysis system. In particular, quality assurance of a quantitative physiological sample test system can be performed without using a quality control sample by monitoring the thermal and temporal stress of a component used with the test system. Alert information can be generated that indicates that the component has failed quality assurance when the thermal and temporal stress exceeds a predetermined thermal-temporal stress threshold. According to an alternative exemplary embodiment, the present invention can provide quality assurance for laboratory quality tests performed by a blood analysis system or the like at the point of patient care by minimizing the need for running liquid-based quality control materials on the analysis system.

Merely for purposes of illustration and not limitation, the present description is provided in the context of an i-STAT system, such as, for example, the i-STAT 1 handheld system available from i-STAT Corporation (East Windsor, N.J.), that is based on a handheld reader and single-use cartridges, to which exemplary embodiments are applicable. However, those skilled in the art will recognize the broader applicability of the present invention to other systems directed to point-of-care testing, bedside testing, and the like that offer similar capabilities with disposable elements. In particular, exemplary embodiments of the present invention are also applicable to other analytical systems known in the art, where a single-use testing device or cartridge includes a sensing means. Such other analytical systems include, for example, those based on electrochemical principles, e.g., potentiometry, amperometry and conductimetry, and testing systems typically referred to as electrodes, modified electrodes, ion-selective electrodes, enzyme electrodes, immuno-electrodes, strip electrodes, biosensors, immunosensors, and the like. These alternative systems and devices also include ones that are based on optical methods, for example, detecting turbidity, or absorbance at one or more selected wavelength, evanescence, fluorescence, luminescence, wave guides, reflectance and the like. These devices can use similar fluidics to the i-STAT system, at least to the extent that a test sample is delivered to a testing region in each device, and that the devices are operated with a re-usable reading apparatus. Thus, exemplary embodiments of the present invention are also applicable to other such systems that can be used at the point of patient care, e.g., the operating room, the emergency room, a physician's office, or other like location.

In a preferred embodiment, the reader can be a hand-held device that is portable or has a small bench-top footprint. Such a reader can be preferably free-standing (e.g., battery operated), so that it can be easily moved to a bedside location if desired. However, such a device can be attached to main power or intermittently to a battery re-charger attached to main power. More particularly, exemplary point-of-care blood analysis systems can be based on a re-usable reading apparatus that performs blood tests using a disposable cartridge that contains (i) analytical elements, e.g., electrodes for sensing analytes, such as, for example, pH, oxygen and glucose; (ii) fluidic elements, e.g., conduits for receiving and delivering the blood sample to the electrodes; and (iii) calibration elements, e.g., aqueous fluids for standardizing the electrodes with a known concentration of each analyte. The reading apparatus can contain the electronics and algorithms for operating the electrodes, e.g., making the measurements and doing computations. The reader also has the ability to display results and communicate those results to the laboratory and hospital information systems (LIS and HIS, respectively), optionally via a computer workstation. Communication between the reader and a workstation can be performed using various suitable communication means, such as, for example, an infrared (IR) or radio frequency (RF) link or the like. Communication between the workstation and a laboratory information system can be performed using any suitable form of wired or wireless connection. Several technologies within the general areas of sensing electrodes, measurement methods, single-use cartridges and readers (also referred to as analyzers and instruments) are disclosed in, for example, the following commonly-assigned patents: U.S. Pat. Nos. 5,096,669, 5,112,455, 5,200,051, 5,212,050, and 5,447,440.

In addition, while the present invention is primarily described for systems where the physiological sample is blood, plasma or serum, exemplary embodiments are also applicable to the analysis of other biological materials, such as, for example, saliva, urine, cerebrospinal fluid, and the like.

Figure 1:
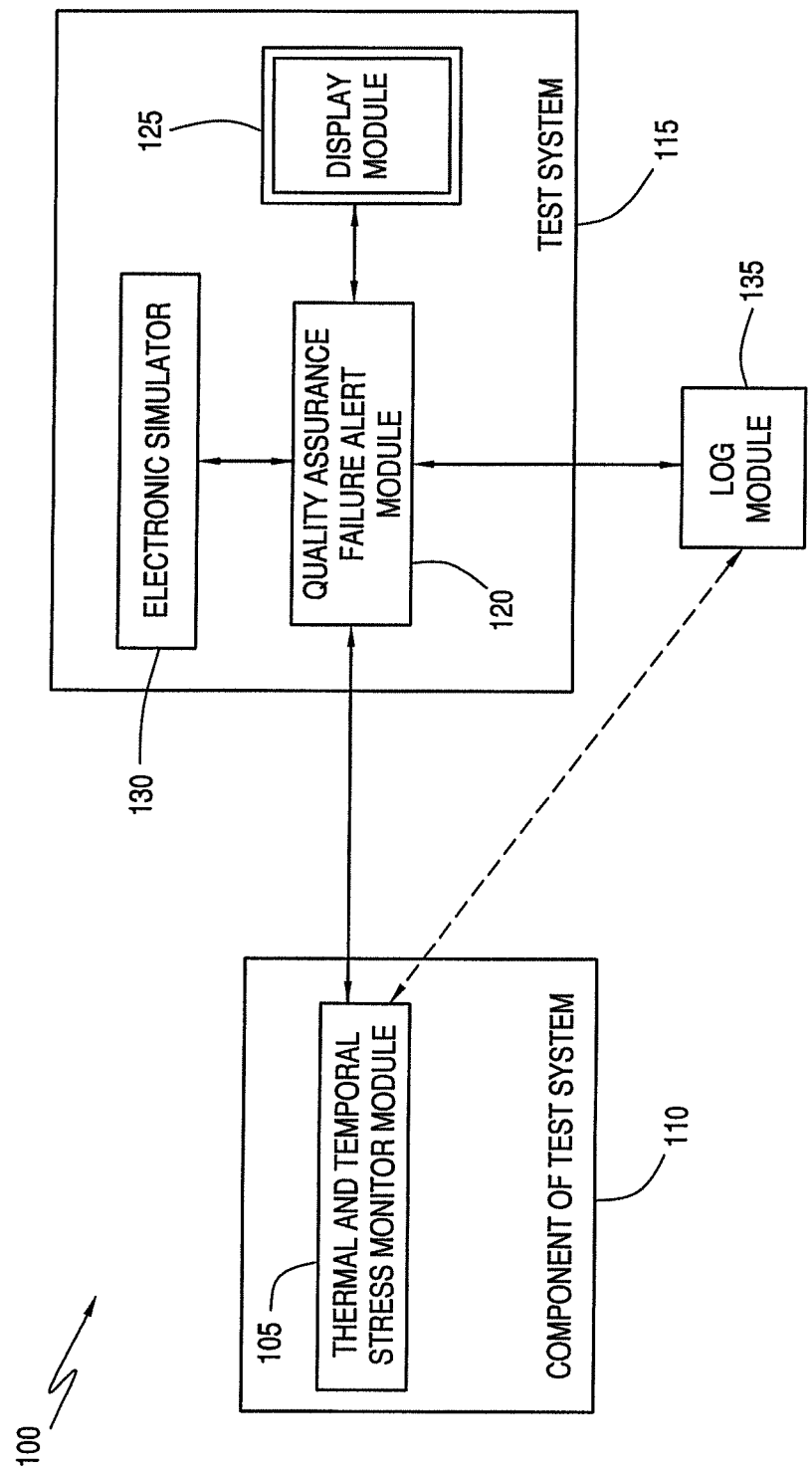
FIG. 1 is a block diagram illustrating a system 100 for performing quality assurance of a quantitative physiological sample test system without using a quality control sample, in accordance with an exemplary embodiment of the present invention.

These and other aspects and embodiments of the present invention will now be described in greater detail. FIG. 1 is a block diagram illustrating a system 100 for performing quality assurance of a quantitative physiological sample test system without using a quality control sample, in accordance with an exemplary embodiment of the present invention. The physiological sample can comprise, for example, blood, plasma, serum, saliva, urine, cerebrospinal fluid, and amended forms thereof. However, skilled artisans will recognize that any suitable physiological sample can be used according to exemplary embodiments. Merely for purposes of illustration, the quality control sample can comprise, for example, a liquid control or the like. However, the quality assurance can be performed by the system 100 without the use of any such quality control sample.

The system 100 includes a thermal and temporal stress monitor module 105. The thermal and temporal stress monitor module 105 is configured or otherwise adapted to monitor the thermal and temporal stress of a component 110 used with the test system 115. According to the exemplary embodiment illustrated in FIG. 1, the thermal and temporal stress monitor module 110 can be separate from the test system 115, but in the same or substantially same thermal environment as the test system 115. However, according to an alternative exemplary embodiment, the thermal and temporal stress monitor module 110 can be integrated with the test system 115. The thermal and temporal stress monitor module 110 can be a part of or otherwise associated with each or any of the components 110 to allow monitoring of the components 110. For example, the thermal and temporal stress monitor module 105 can be configured to monitor a temperature-time indicator or the like associated with the component 110.

Although a single component 110 is illustrated in FIG. 1 merely for simplicity of discussion, any suitable number of components 110 can be used with the system 100. For purposes of illustration and not limitation, the component 110 can comprise a sample testing cartridge or the like. For example, the test system 115 can comprise a blood analysis system or the like. Accordingly, the component 110 can comprise a blood testing cartridge, such as, for example, a single-use blood testing cartridge or other suitable type of disposable component. Such a blood testing cartridge can include, for example, at least one electrochemical sensor. For example, the blood testing system can comprise a portable component reader, such as the reader discussed above, or other like device. According to an alternative exemplary embodiment; the component 110 can comprise a sensor. For example, the sensor can comprises one of the following: an electrochemical sensor; an optical sensor; a luminescence sensor; a fluorescence sensor; an amperometric sensor; a potentiometric sensor; a conductimetric sensor; a wave guide; an evanescence sensor; a biosensor; a surface plasmon resonance sensor; an acoustic wave sensor; and a reflectance sensor. The test system 115 can be configured to perform a test to determine an analyte. For example, the analyte can comprise sodium, potassium, chloride, calcium, glucose, lactate, creatinine, urea, hematocrit, prothrombin time, activated clotting time, activated partial thromboplastin time, troponin I, troponin T, creatine kinase MB, brain natriuretic peptide, NTproBNP, C-reactive protein, $pO_2$, $PCO_2$, or pH.

The system 100 also includes a quality assurance failure alert module 120 in communication with the thermal and temporal stress monitor module 105. The quality assurance failure alert module 120 is configured or otherwise adapted to generate alert information indicating that the component 110 has failed quality assurance when the thermal and temporal stress exceeds a predetermined thermal-temporal stress threshold. For example, assuming that the component 110 comprises a (disposable or single-use) cartridge, the thermal and temporal stress information associated with the component 110 can be communicated from the thermal and temporal stress monitor module 105 to the quality assurance failure alert module 120 upon insertion or other suitable engagement of the component 110 with the test system 115. For example, the quality assurance failure alert module 120 can perform a comparison of the thermal and temporal stress information and the predetermined thermal-temporal stress threshold. The component 110 can be used with the test system 115 when the thermal and temporal stress does not exceed the predetermined thermal-temporal stress threshold.

The test system 115 can include a display module 125. The display module 125 can provide the graphical and/or textual interface through which the users can view information from and interact with the test system 115. For example, the display module 125 can comprise a suitable computer monitor or screen or other appropriate display device that is capable of displaying graphical and/or textual information. The display module 125 can be configured to display alerts in accordance with the alert information from the quality assurance failure alert module 120. In other words, if the thermal and temporal stress of the component 110 exceeds the predetermined thermal-stress threshold, appropriate alerts can be displayed via the display module 125. For example, such alerts can notify the user of the quality assurance failure of the component 110, instruct the user to discard the component 110 and/or ignore the test results from the component 110, or provide other suitable instructions, notifications, and alerts. Additionally or alternatively, the quality assurance failure alert module 120 can be configured to suppress the display of test results from the component 110 when the component 110 has failed quality assurance.

According to exemplary embodiments, the predetermined thermal-temporal stress threshold can be generated using any suitable means, and the actual threshold will depend on various factors, including the nature and type of components 110 and test system 115 used, the environment in which the components 110 and test system 115 are being used, and other like factors. For example, the predetermined thermal-temporal stress threshold can be generated in accordance with the total allowable error of the test system 115. Alternatively, the predetermined thermal-temporal stress threshold can comprise a plurality of combinations of thermal stress and temporal stress. According to an alternative exemplary embodiment, the predetermined thermal-temporal stress threshold can comprise a predetermined temperature-time profile providing a range of temperature and time conditions within which the quality assurance of the component 110 can be maintained.

Each of the thermal and temporal stress monitor module 105 and quality assurance failure alert module 120 can be comprised of any suitable type of electrical or electronic component or device that is capable of performing the functions associated with the respective element. According to such an exemplary embodiment, each component or device can be in communication with another component or device using any appropriate type of electrical connection that is capable of carrying (e.g., electrical) information. Alternatively, each of these modules can be comprised of any combination of hardware, firmware and software that is capable of performing the functions associated with the respective module.

Alternatively, the system 100 can be comprised of one or more microprocessors and associated memory(ies) that store the steps of a computer program to perform the functions of any or all of the modules of the system 100. The microprocessor can be any suitable type of processor, such as, for example, any type of general purpose microprocessor or microcontroller, a digital signal processing (DSP) processor, an application-specific integrated circuit (ASIC), a programmable read-only memory (PROM), an erasable programmable read-only memory (EPROM), an electrically-erasable programmable read-only memory (EEPROM), a computer-readable medium, or the like. The memory can be any suitable type of computer memory or any other type of electronic storage medium, such as, for example, read-only memory (ROM), random access memory (RAM), cache memory, compact disc read-only memory (CDROM), electro-optical memory, magneto-optical memory, or the like. As will be appreciated based on the present description, the memory can be programmed using conventional techniques known to those having ordinary skill in the art of computer programming to perform the functions of any or all of the modules of the system 100. For example, the actual source code or object code of the computer program can be stored in the memory.

According to an alternative exemplary embodiment, the thermal and temporal stress monitor module 105 can comprise or be configured to monitor one or more of the following: an electrically conductive wax; a temperature-dependent liquid crystal; a shift in baseline calibration potential of a potentiometric sensor; a liposomal release of an enzyme inhibitor; a liposomal release of an electrically conductive liquid; a liposomal release of an elevated ion concentration; a liposomal release of a molecule or ion capable of electrochemical detection; a thermistor; a thermocouple; a thermal ink; a temperature-dependent chemical reaction; a temperature-dependent color changing patch; and a temperature-dependent phase change of a material.

According to exemplary embodiments, the quality control system and method for protecting against systematic analytical error can include three parts that are in essentially two different operational areas. First, a facility, such as a hospital or the like, is responsible for monitoring and managing any thermal stress associated with the components 110 (e.g., test devices or cartridges). Such monitoring can be performed by the thermal and temporal stress monitor module 105. Second, the test system 115 can include a set of in-built monitoring and management features. Such features can include, for example, failsafe mechanisms, also termed "quality checks for customers," that are automatically engaged during each component 110 test cycle. Furthermore, the test system 115 can include an electronic simulator 130 that is configured to simulate signals produced by the component 110. The electronic simulator 130 can be in communication with, for example, the quality assurance failure alert module 120. The electronic simulator 120 can also provide additional testing of the test system 115. Each of the aforementioned parts are described in greater detail below.

For a facility or user to manage thermal stress of components 110, the manufacturer can provide quality control operating rules that require the facility to ensure that the components 110 are not exposed to thermal stress beyond predetermined limits. Merely for purposes of illustration and not limitation, the following set of rules can be provided: (i) shipping temperature must be verified upon receipt by inspecting the temperature strip included with each shipment; (ii) cartridges must remain refrigerated under 8° C. for long-term storage; (iii) cartridges must not be at room temperature for more than 14 days prior to use; and (iv) cartridges must not be exposed to temperatures greater than 30° C. Such rules can be programmed or otherwise stored in the thermal and temporal stress monitor module 105 (e.g., in a suitable look-up table stored in an appropriate computer storage medium). If the thermal and temporal stress specified by these rules is exceeded for a component 110, the thermal and temporal stress monitor module 105 can provide a signal or other suitable indication or information to the quality assurance failure alert module 120 so that the user can be appropriately alerted that the component 110 has failed quality assurance.

Any additional or alternative rules can be used to ensure that the components 110 are not exposed to thermal and temporal stress beyond the predetermined limits. For example, it will be apparent to those skilled in the art that changes in designated temperature values and time duration can be adapted to different types of components 110. Instructions can be provided to a facility by means of, for example, a product manual, a product quick reference guide, an e-mail, a website link and data page, or the like, to discard or return components 110 that are exposed to thermal and temporal stress beyond preset limits. For example, such information can be used to update the quality control rules and instructions maintained by the thermal and temporal stress monitor module 105.

According to an exemplary embodiment, the quality control operating rules can also require that the facility monitor both refrigerator and room temperatures, and maintain associated records that can be verified during an audit. Such monitoring can be performed using monitoring systems already well established for the storage of other medical supplies, such as vaccines and pharmaceuticals, as described in, for example, Guidelines for Maintaining and Managing the Vaccine Cold Chain, MMWR, October 2003. For example, the system 100 can include a log module 135 in communication with the quality assurance failure alert module 120. The log module 135 can be configured to maintain a log of the thermal and temporal stress of a plurality of components 110. The log module 135 can comprise a database or other computer storage medium separate from and in communication with the test system 115. However, according to an alternative exemplary embodiment, the log module 135 can be integrated with the test system 115. The thermal and temporal stress information can be passed or otherwise communicated to the log module 135 from the thermal and temporal stress monitor module 105, quality assurance failure alert module 120, and/or any other monitoring systems being used in conjunction with the system 100.

For the purpose of the user, a set of recommendations for protecting against excessive temperature stress of components 110 can also be provided. For purposes of illustration and not limitation, for protection against excessive temperature stress of components 110 during shipment, the following sequence of user rules can be applied: (1) examine a temperature indicator strip included with each component 110 shipment; (2) if the strip shows the shipment was not exposed to excessive temperature, then retain a photocopy as a quality control record; (3) if the strip shows the shipment was exposed to excessive temperature, then test the Level 1 quality control solution on a component 110 from the shipment and retain the results as a quality control record; (4) if the test shows unacceptable results, then discard the shipment; otherwise (5) if the test shows acceptable results then accept the components 110.

For protection against excessive temperature stress of components 110 resulting from improper storage of those components 110 on site, the facility can use one of several approaches. Two approaches are provided here by way of example. In the first approach, the facility can have an automated temperature log (24 hours a day, 7 days a week) for the refrigerator and for the room where the system is used: (1) retain the temperature logs as a quality control record; (2) if the refrigerator temperature log indicates that the refrigerator has exceeded 8° C., then test the Level 1 quality control solution on a component 110 from the refrigerator and retain the results as a quality control record; (3) if the test shows unacceptable results, then discard the components 110; (4) if the room temperature log indicates that the room has exceeded 30° C., then test the Level 1 quality control solution on any component 110 that was sitting at room temperature and retain the results as a quality control record; and (5) if the test shows unacceptable results, then discard the components 110. The functionality of the automated temperature log can be performed by, for example, the log module 135. Alternatively, information from a separate automated temperature log can be communicated to the log module 135 for recordation, storage, and later retrieval. In the second approach, the facility does not have an automated temperature log. Therefore, (1) on a monthly basis, test the Level 1 liquid quality control on a component 110 from the lot currently in use and retain the results as a quality control record; and (2) if the test shows unacceptable results, then discard the components 110.

According to an exemplary embodiment, the test system 115 is configured to perform at least one failsafe check prior to use of the component 110. More particularly, failsafe mechanisms or other suitable quality checks for customers can be automatically engaged during each component 110 test. For example, an appropriate software algorithm in the test system 115 (e.g., a handheld point-of-care testing instrument) can be configured to automatically cause the suppression of test results if a failsafe check is triggered. The test system 115 can display the source of the error and the appropriate action to the user via the display module 125. Merely for purposes of illustration and not limitation, examples of the displayed failsafe and required subsequent action can include, but are not limited to, the following: SAMPLE POSITIONED SHORT OF FILL MARK—RUN ANOTHER CARTRIDGE; CARTRIDGE ERROR—RUN ANOTHER CARTRIDGE; DEAD BATTERIES—REPLACE BATTERIES; and ANALYZER ERROR—SEE MANUAL/USE ELECTRONIC SIMULATOR. Other similar displayed messages will be apparent to those skilled in the art of clinical sample analysis. Thus, the failsafe checks can comprise, for example, the verification that an ambient temperature is within a predetermined range, verification that the component 110 is not faulty, and/or verification that the test system 115 is not faulty. For example, the verification that the test system 115 is not faulty can comprise testing electrical integrity of an electrical connector associated with the test system 115, and/or testing operational integrity of operational amplifiers associated with the test system 115. Assuming that each component 110 comprises a (single-use or disposable) cartridge, a non-exhaustive list of the test parameters addressed by automated failsafe quality checks is illustrated in Table 2.

TABLE 2

Automatic Quality Check Failsafe Mechanisms

| | When Verified |
|---|---|
| Unit-Use Cartridge | |
| Microfabricated Electrochemical Sensor Elements: | |
| verify sensors are present | every cartridge use |
| verify sensor characteristics are consistent with expectations of a properly manufactured and maintained device (by testing internal calibration fluid) | every cartridge use |
| Internal Calibration Fluid: | |
| verify fluid is present | every cartridge use |
| verify fluid is delivered free of bubbles | every cartridge use |
| verify fluid has proper concentration | every cartridge use |
| Fluidic System: | |
| verify sample holding chamber is sealed | every cartridge use |
| verify fluid flowpaths are intact (no part of the Handheld comes into direct contact with fluid) | every cartridge use |
| verify waste chamber is not occluded | every cartridge use |
| Elements that Interact with the Handheld Reader: | |
| verify electrical contact pads (that allow access to sensor signals) are not occluded | every cartridge use |
| verify internal element of cartridge that allows the Handheld Reader to control the release of calibration fluid over the sensors is functioning properly | every cartridge use |
| verify internal element of cartridge that allows the Handheld to control the replacement of calibration fluid with sample is functioning properly | every cartridge use |
| Handheld Reader | |
| Motorized Mechanical System: | |
| verify electrical contact is made with sensors on cartridge | every cartridge use |
| verify ability to properly move calibration fluid | every cartridge use |
| verify ability to properly move sample | every cartridge use |
| Electrical Measurement System: | |
| verify voltage measuring system for potentiometric sensors | Electronic Simulator |
| verify current measuring system for amperometric sensors | Electronic Simulator |
| verify resistance measuring system for conductimetric sensors | Electronic Simulator |
| Other: | |
| verify internal self-consistency of electronic systems | every cartridge use |
| verify fluid flow using the conductivity sensor | every cartridge use |
| verify function of transducers used for measuring barometric pressure | every cartridge use |
| verify function of the thermistors used to set control chip temperature | Electronic Simulator |

TABLE 2-continued

Automatic Quality Check Failsafe Mechanisms

| | When Verified |
|---|---|
| Operator Sample Handling/Cartridge Handling | |
| verify the cartridge inserted has not been previously used | every cartridge use |
| verify the calibration pack has not prematurely ruptured | every cartridge use |
| verify the electronic contact pads are dry and uncontaminated | every cartridge use |
| verify the proper amount of sample was placed into the sample chamber | every cartridge use |
| verify the sample was properly positioned within the sample chamber | every cartridge use |
| verify the sample is free of included bubbles | every cartridge use |
| verify the sample is not clotted | every cartridge use |
| verify the sample chamber is properly sealed with the snap closure | every cartridge use |
| Environmental Conditions | |
| verify the ambient temperature is within range | every cartridge use |
| verify the ambient pressure is within range | every cartridge use |

Further details of three additional failsafe tests that can be performed by the test system 115 are illustrated in the following examples. In following examples, it is again assumed that each component 110 comprises a (single-use or disposable) cartridge.

Example 1

Verify the presence of calibration fluid. Calibration fluid may not be present if cartridge handling has ruptured the calibration fluid package within the cartridge. The verification is achieved by a measurement of electrical resistance across the sensor area of the cartridge. Failure to achieve an expected resistance in such a failsafe test results in the suppression of the analytical result and display of an error message to the user (e.g., via the display module 125).

Example 2

Verify the sample was properly positioned within the sample chamber. If the sample volume inserted into the cartridge is either too great or too little, expected characteristics of the electrical signal between sensors will not be attained. Failure to achieve an expected result in such a failsafe test results in the suppression of the analytical result and display of an error message to the user (e.g., via the display module 125).

Example 3

Figure 2:
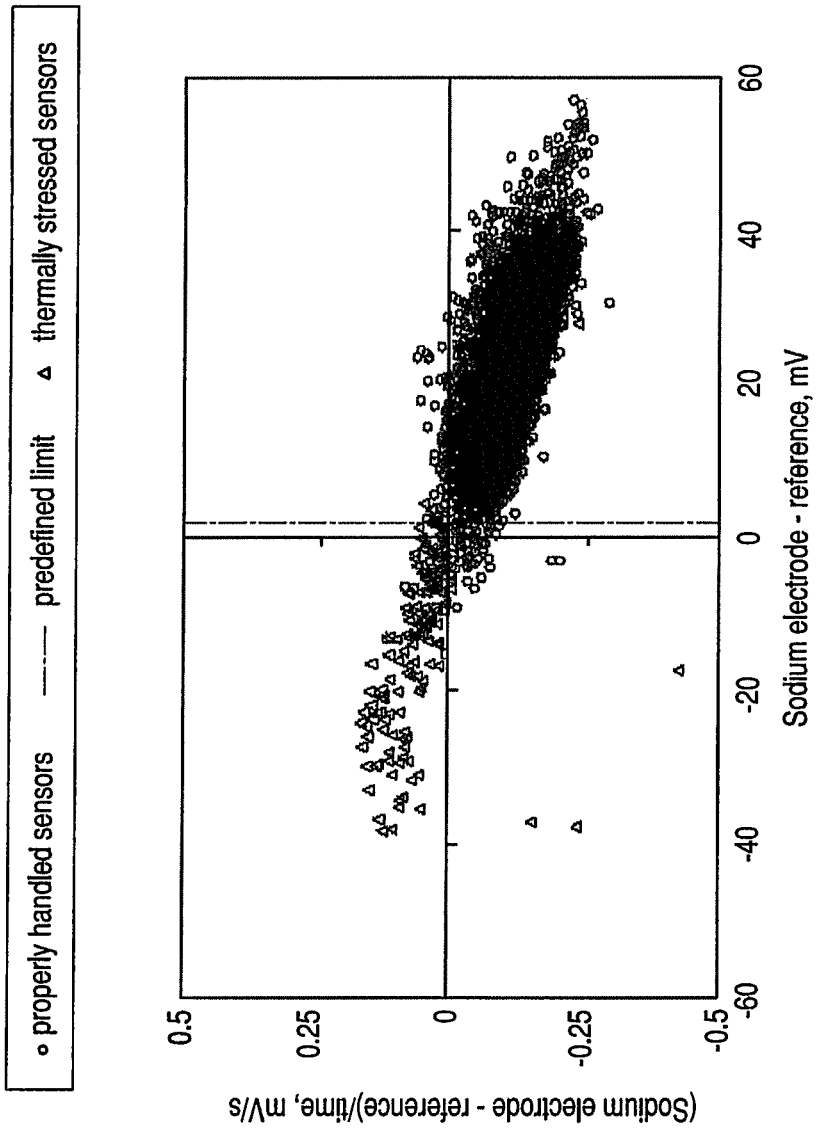
FIG. 2 illustrates a graphical representation of sodium cal-volt data (x-axis) versus cal-drift (y-axis) with system cal-volt and cal-drift threshold limits, in accordance with an exemplary embodiment of the present invention.
Figure 3:
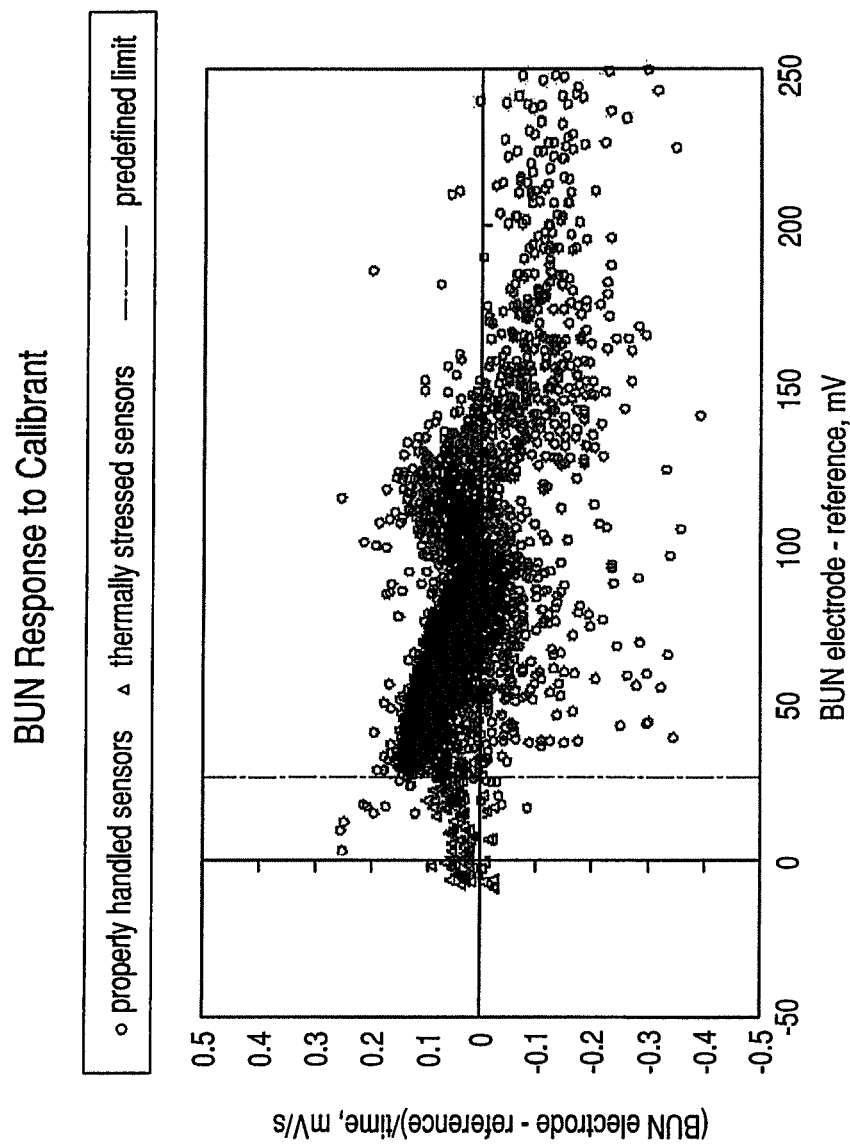
FIG. 3 illustrates a graphical representation of blood urea nitrogen cal-volt data (x-axis) versus cal-drift (y-axis) with system cal-volt and cal-drift threshold limits, in accordance with an exemplary embodiment of the present invention.
Figure 4:
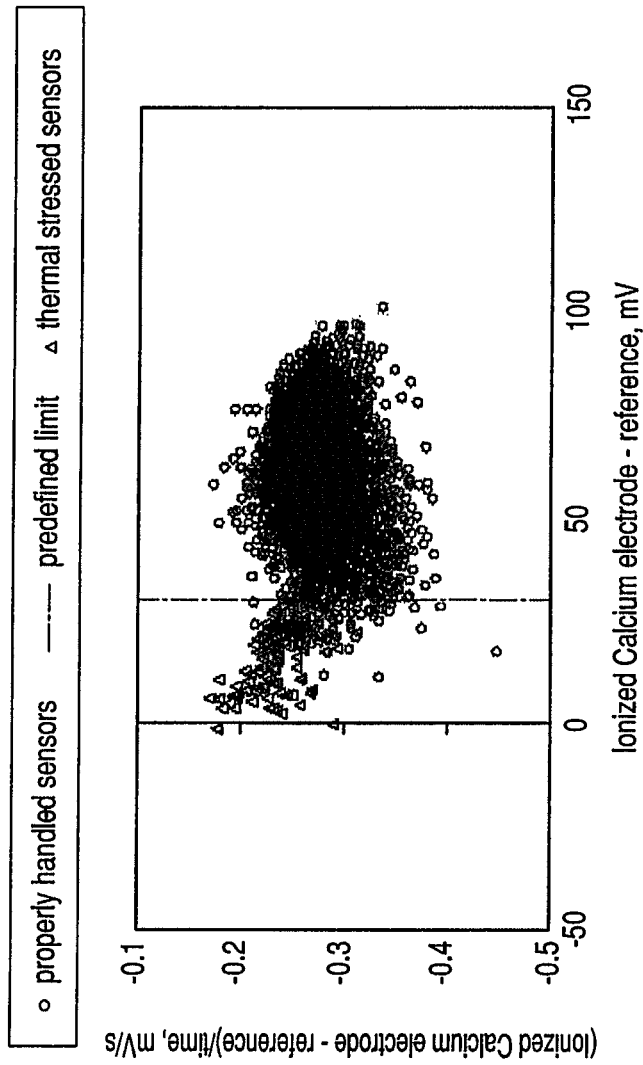
FIG. 4 illustrates a graphical representation of calcium cal-volt data (x-axis) versus cal-drift (y-axis) with system cal-volt and cal-drift threshold limits, in accordance with an exemplary embodiment of the present invention.

Verify the ambient temperature is within range. An electronic thermometer in the test system 115 records the ambient temperature. If the ambient temperature is outside the specifications, an error message is presented to the user (e.g., via the display module 125), and the test cycle is not initiated. Experimental support for the applicability of such a failsafe test was obtained by intentionally exposing cartridges to thermal stress. Graphical representations of such a phenomenon are illustrated in FIGS. 2, 3, and 4 for sodium, blood urea nitrogen, and calcium, respectively, which are x-y plots of cal-volt data (x-axis) versus cal-drift (y-axis). These plots include the current system cal-volt and cal-drift threshold limits.

According to an exemplary embodiment, if the failsafe was triggered by an operator error or component 110 fault, the user is informed and instructed via display module 125 to run another component 110. Such a failsafe protects against systematic error introduced by user technique or damage to a batch, group or set of components 110. Furthermore, if the failsafe was triggered by a fault in the test system 115, the user is instructed on the display module 125 to correct the causative condition, e.g. low battery, temperature out of range, expired software, or the like. Where the causative condition is not correctable by the user, the display module 125 can display instructions for the user to engage the manufacture's technical services department, for example, to obtain a replacement test system 115. Additionally, such information can be provided to the user in an appropriate user manual from the manufacturer that describes the features and operation of the test system 115.

As discussed previously, the test system 115 can include the automated operation of an internal electronic simulator 130. For example, the electronic simulator 130 can be a separate circuit or device within the test system 115 that is configured to simulate signals produced by the component 110. These simulated signals can be routed to the measurement circuits of the test system 115 to provide an independent confirmation of calibration, such as described in, for example, commonly-assigned U.S. Pat. No. 5,124,661, entitled "Reusable Test Unit for Simulating Electrochemical Sensor Signals for Quality Assurance of Portable Blood Analyzer Instruments." In a preferred embodiment, the check performed by the electronic simulator 130 can be automatically run every 24 hours, although any suitable time period can be used. The electronic simulator 130 can be used to check that the internal connector that contacts each component 110 is free from material that could cause stray conductive paths, i.e., compromise the integrity of the connector, and that the operational amplifiers that amplify the electrochemical signals from the sensors are within specifications. In other words, the electronic simulator 130 can be configured to generate simulation signals for testing electrical integrity of an electrical connector associated with the test system 115 and/or operational integrity of operational amplifiers associated with the test system 115. If the electronic simulator 130 check fails, the test system 115 will subsequently not process a component 110 and alert the user to the reason of the failure through the display module 125. As the causative condition for the amplifier test is not correctable by the user, either the display module 125 or manual can instruct the user to engage the manufacture's technical services to obtain a replacement test system 115.

Where the causative condition is dirt on the connector, the user can be directed to a cleaning protocol to remove the dirt.

Thus, unlike conventional methods where external liquid control materials are used with the test system 115 (e.g., cartridge-reader combination) for purposes of quality control, exemplary embodiments of the present invention no longer require such external liquid control materials, as the combination of quality control measures described above and herein is sufficient for reliable use. However, it is noted that external liquid control materials can still be provided for use with the test system 115, as such materials can be useful as, for example, a blood substitute for training and general system troubleshooting.

In addition, unlike conventional in vitro diagnostic systems that provide test results with a precision of better than about 10%, exemplary embodiments of the present invention do not require such external controls to minimize the rate of erroneous results. The rationale is illustrated in a preferred embodiment, notably the i-STAT blood testing system comprising the i-STAT 1 handheld analyzer used in combination with the CHEM8+ cartridge, all available from i-STAT Corporation. The CHEM8+ cartridge performs blood tests with electrochemical sensors for sodium, potassium, chloride, calcium, glucose, total carbon dioxide, blood urea nitrogen, creatinine, and hematocrit, and provides calculated values for several other parameters. Other than thermal stress of the cartridges (e.g. CHEM8+), the design of the i-STAT system eliminates sources of systematic error (e.g., the operator-induced influences described above) that external liquid quality controls had previously been required for detecting. Such systematic errors include operator-induced influences described above that can be managed with failsafe mechanisms and the electronic simulator 130. Furthermore, exemplary embodiments of the present invention provide the inherent benefit of a unit-use analytical system compared to a multi-use one. More specifically, as the sensors and flow-paths in the CHEM8+ cartridge are stored dry, the sensors and flow-paths are not exposed to potential sources of systematic error from repeated exposure to fluids, such as, for example, leaching of sensor active material and protein contamination, as is well-known for multi-use testing systems.

Another beneficial feature of the present invention is a form of factory-established calibration in which the accuracy of the component 110 readings is confirmed in the factory prior to shipment to the user. As the calibration is factory set and the test system 115 is explicitly designed to lack means for the user to change or alter that calibration in any way, there is no mechanism for the user to misadjust calibration of the test system 115. As a result, systematic error from calibration can be substantially, if not completely, eliminated. A further beneficial feature of the present invention is environmental control. For the exemplary embodiment in which the components 110 comprise cartridges, each test cartridge can be individually packaged in a sealed pouch, such as, for example, foil or a foil-buttercup combination, to provide controlled humidity during storage.

Figure 5:
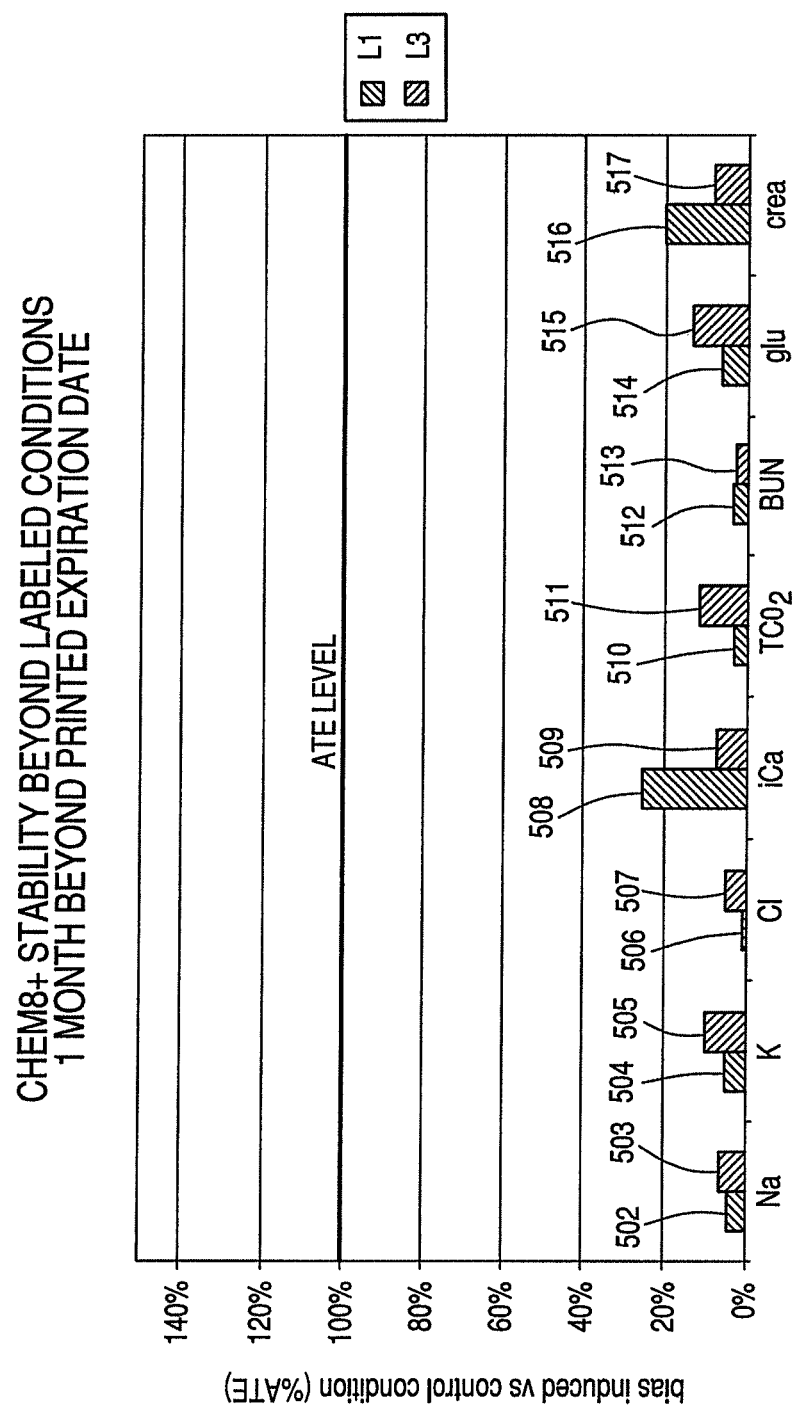
FIG. 5 is a graphical representation illustrating the stability beyond labeled conditions, one month beyond the printed expiration date, for an i-STAT CHEM8+ cartridge containing sensors for sodium, potassium, chloride, calcium, glucose, total carbon dioxide, blood urea nitrogen, creatinine and hematocrit, in accordance with an exemplary embodiment of the present invention. The change in induced bias versus the control condition allowable total error (ATE) is plotted for each test.
Figure 6:
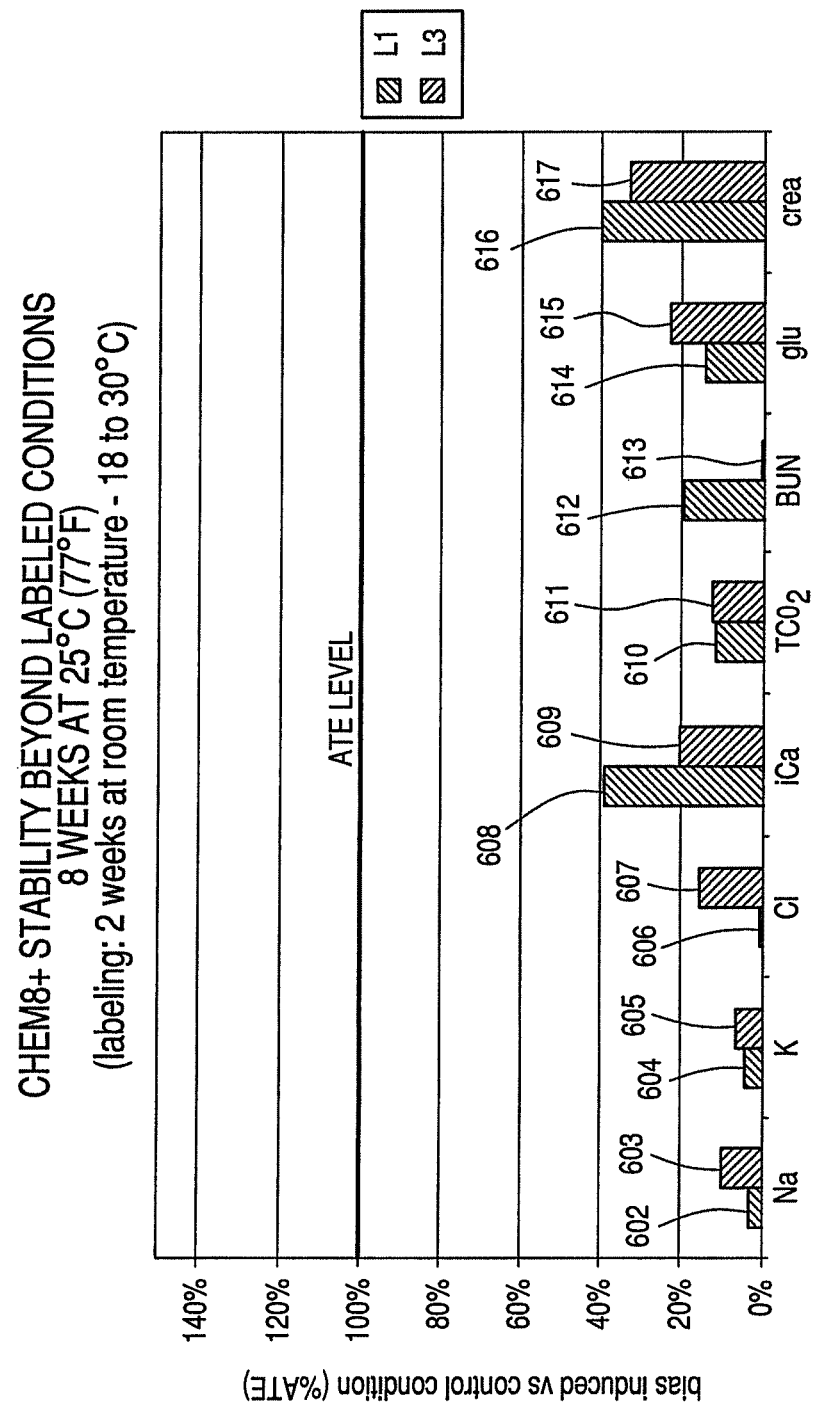
FIG. 6 is a graphical representation illustrating the stability beyond labeled conditions, eight weeks beyond the printed expiration date at 25° C., for an i-STAT CHEM8+ cartridge containing sensors for sodium, potassium, chloride, calcium, glucose, total carbon dioxide, blood urea nitrogen, creatinine and hematocrit, in accordance with an exemplary embodiment of the present invention. The change in induced bias versus the control condition ATE is plotted for each test.
Figure 7:
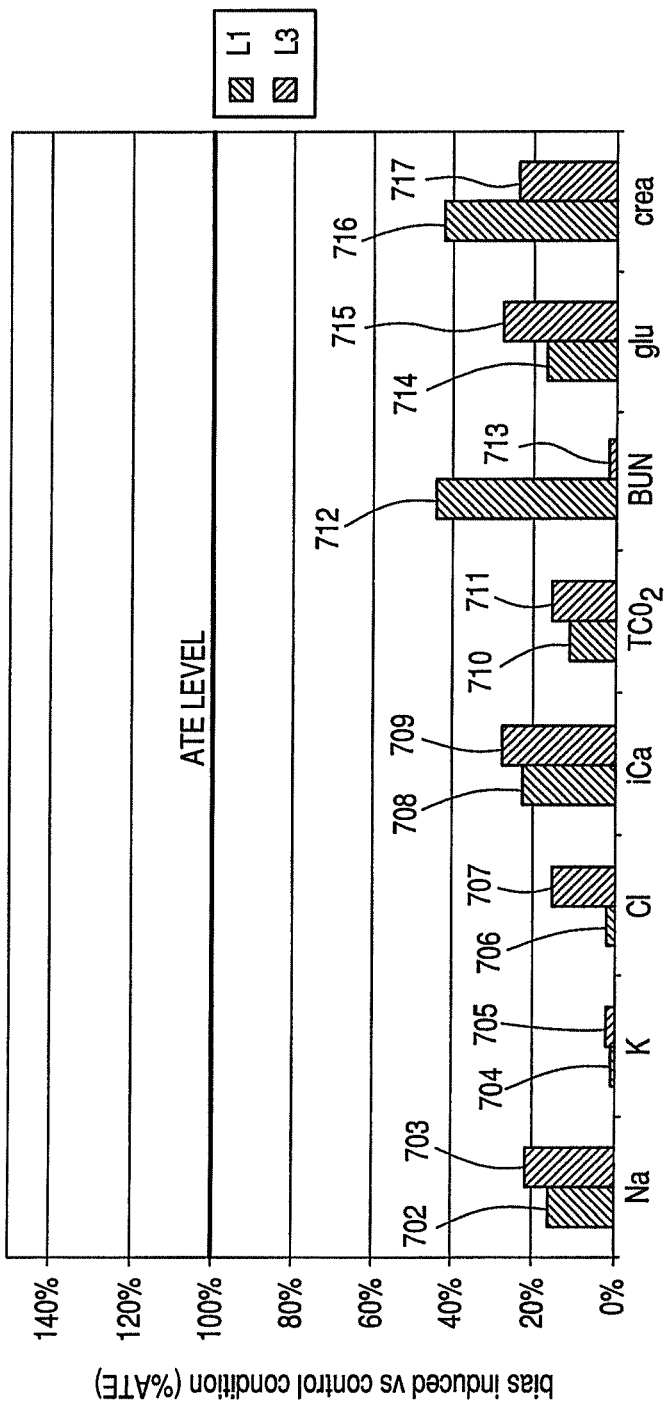
FIG. 7 is a graphical representation illustrating the stability beyond labeled conditions, three weeks beyond the printed expiration date at 30° C., for an i-STAT CHEM8+ cartridge containing sensors for sodium, potassium, chloride, calcium, glucose, total carbon dioxide, blood urea nitrogen, creatinine and hematocrit, in accordance with an exemplary embodiment of the present invention. The change in induced bias versus the control condition ATE is plotted for each test.

According to exemplary embodiments of the present invention, it has been found that the aforementioned quality control methodology provides excellent protection against systematic error, because the selected storage limitations are sufficiently conservative for application to point-of-care blood testing or other like testing. Such results are illustrated in FIGS. 5, 6 and 7, in which monitoring occurs with respect to a selected thermal stress threshold value that is a combination of time and temperature. Each figure illustrates the size of the systematic analytical bias induced by imposing a thermal stress beyond one of the stated limits. In particular, FIG. 5 is a graphical representation illustrating the stability beyond labeled conditions, one month beyond the printed expiration date, for an i-STAT CHEM8+ cartridge containing sensors for sodium, potassium, chloride, calcium, glucose, total carbon dioxide, blood urea nitrogen, creatinine and hematocrit. The change in induced bias versus the control condition allowable total error (ATE) is plotted for each test. FIG. 6 is a graphical representation illustrating the stability beyond labeled conditions, eight weeks beyond the printed expiration date at 25° C., for an i-STAT CHEM8+ cartridge containing sensors for sodium, potassium, chloride, calcium, glucose, total carbon dioxide, blood urea nitrogen, creatinine and hematocrit. The change in induced bias versus the control condition ATE is plotted for each test. In particular, FIG. 6 illustrates the analytic bias observed for cartridges that were left at room temperature for 8 weeks compared to cartridges stored in the refrigerator for the same 8 week period. It is noted that in the example illustrated in FIG. 6, the manufacturer's stated non-refrigerated shelf-life for these cartridges is 2 weeks. FIG. 7 is a graphical representation illustrating the stability beyond labeled conditions, three weeks beyond the printed expiration date at 30° C., for an i-STAT CHEM8+ cartridge containing sensors for sodium, potassium, chloride, calcium, glucose, total carbon dioxide, blood urea nitrogen, creatinine and hematocrit. The change in induced bias versus the control condition ATE is plotted for each test.

The height of each bar in FIGS. 5-7 represents the bias as a percentage of the ATE established for each specific analyte, as illustrated in FIG. 8(A). FIG. 8 illustrates (A) a table for ATE acceptance criteria, (B) an LER (limits for erroneous results) acceptance criteria table for electrolytes, glucose and hematocrit tests, and (C) LER acceptance criteria table for blood urea nitrogen and creatinine tests, in accordance with an exemplary embodiment of the present invention. Data in FIGS. 5-7 are provided using the LER for each test (see FIGS. 8(B) and 8(C)), as required by the FDA. The term ATE will be familiar to those skilled in the art of clinical chemistry. The ATE limits describe expectations for agreement between two analytical methods. The ATE limit is an indication of the accuracy of each test, as described in, for example, FDA Draft Guidance for Waiver (September 2005). The ATE values in the figures are derived directly from the United States FDA Clinical Laboratory Improvements Amendments (CLIA) proficiency testing limits, where such fixed limits are available. For the bars in each of FIGS. 5-7, the even-numbered bars represent measurements using Level 1 control fluid, and the odd-numbered bars represent measurements using Level 3 control fluid. Both control fluids were supplied by i-STAT Corporation, and have concentration value assignments for each analyte that is tested. FIGS. 9 and 10 illustrate anticipated mean reported test values and ranges for these control fluids when run with an i-STAT CHEM8+ cartridge. In particular, FIG. 9 illustrates the expected mean values and ranges for sodium, potassium, calcium, total CO2, glucose, creatinine, chloride and urea controls ((A) Level 1 and (B) Level 3) used with an i-STAT CHEM8+ cartridge that performs these blood tests. FIG. 10 illustrates the expected mean values and ranges for hematocrit controls ((A) Level 1 and (B) Level 3) used with an i-STAT CHEM8+ cartridge that tests for hematocrit among a number of other blood tests.

It is noted that even after 8 weeks, FIG. 5 illustrates that all the observed biases were significantly smaller than one-half of the associated ATE. It is further noted that these conservative ATE limits also provide a significant cushion to absorb occasional undetected errors or systematic "blind spots," where a facility is not using automated temperature monitoring. Such a blind spot could be caused by, for example, an unrecognized overnight power failure that allowed refrigerated cartridges to approach room temperature.

It will be understood by those skilled in the art that a combined thermal and temporal stress value can be based on the integral combination of the two effects in determining the system threshold value, i.e., the predetermined thermal-temporal stress threshold. For example, a threshold value can be exceeded by a significantly elevated temperature excursion for a shorter period, as illustrated in FIG. 11. More particularly, FIG. 11 illustrates the stability beyond labeled conditions, two weeks beyond the printed expiration date at 35° C., for an i-STAT CHEM8+ cartridge containing sensors for sodium, potassium, chloride, calcium, glucose, total carbon dioxide, blood urea nitrogen, creatinine and hematocrit. The change in induced bias versus the control condition ATE is plotted for each test. Again, the even-numbered bars represent measurements using Level 1 control fluid, and the odd-numbered bars represent measurements using Level 3 control fluid. Likewise, the threshold can also be exceeded by a smaller elevated temperature excursion for a longer period, as illustrated in FIG. 7. In another example, the temperature may not have exceeded the designated storage temperature, but the allowable time or shelf-life at that temperature may be exceeded, as illustrated in FIGS. 5 and 6. Thus, the thermal-temporal stress threshold value would be exceeded. The actual predetermined thermal-temporal stress threshold used by the test system 115 for the components 110 will depend on many factors. The guidelines of the general type described in the present disclosure will enable a manufacture to determine how to set a product-specific threshold value.

It has surprisingly been found that control of storage conditions to such conservative limits, along with the other design elements and failsafe mechanisms discussed above, ensure performance accuracy at a level beyond that which can be ascertained by running multiple cartridges with control solutions that is used in the conventional method of quality control for quantitative measurement using point-of-care blood testing systems. Specifically, users operating under the established conventional method will test cartridges with liquid quality control solutions at the time of supply from the manufacture. Furthermore, it is known that with the conventional method, some users must also re-test on a weekly or monthly basis thereafter to address specific regulatory or facility-specific requirements. Exemplary embodiments of the present invention provide users with a substantial improvement in convenience over the conventional method, and enable and provide for wider adoption of point-of-care testing systems that yield laboratory-grade results in terms of accuracy and precision.

The College of American Pathologists (CAP) proficiency survey data presented in FIGS. 12-21 illustrate the inherent robustness of exemplary embodiments of the present invention. Proficiency testing is a method by which clinical laboratories are able to demonstrate analytical performance of their instruments. An individual laboratory's analytical results are assessed relative to the analytical performance of the same samples determined on hundreds or thousands of peer laboratories. An expectation for agreement to the peer group is generally three standard deviations (3 sd). Data presented in FIGS. 12-21 reveal excellent precision compared to peer instrument results derived from more than a thousand users. These precision data include all sources of variations, including lot-to-lot variations over many hundreds of lots, and a variety of cartridge age and storage conditions. According to exemplary embodiments, as users of single-use disposable blood testing cartridges have no mechanism or means to adjust test calibration, the only action they could take in response to a performance problem indicated by external liquid quality control solutions would be to take the cartridges out of service.

Exemplary embodiments of the present invention can also provides a mechanism and methodology of characterizing a manufacturing lot of single-use test devices with respect to end-user quality assurance, where the devices are intended to perform one or more tests to a precision of better than about 10%. The methodology is based on determining the performance of a first portion of the manufacturing lot in the absence of thermal and temporal stress with respect to an allowable total error for each test, and then applying thermal and temporal stresses to one or more other portions of the lot and determining the performance of each portion with respect to the allowable total error for each test. The differences in performance of the first and other portions can then be determined. Such a series of steps provides a methodology for deriving a thermal-temporal stress threshold for use by a test system 115 that uses the lot of components 110. Subsequently, for example, a test system 115 at a point-of-care location can determine whether components 110 from that lot have or have not been exposed to sufficient thermal and temporal stress to be rejected or otherwise prohibited or prevented from use in testing.

Thus, according to an exemplary embodiment, the component 110 is associated with a batch of substantially similar components 110 in a manufacturing lot. The quality assurance failure alert module 120 can be configured to generate alert information indicating that the batch has failed quality assurance when the thermal and temporal stress of a component 110 of the lot exceeds the predetermined thermal-temporal stress threshold. In other words, the test system 115 can be used to test one or a few components 110 from a manufacturing lot of many components 110. If the quality assurance failure alert module 120 determines that the thermal and temporal stress of the one or few components 110 has exceeded the predetermined thermal-temporal stress threshold, the user can be warned or otherwise notified (e.g., via display module 125) that the entire manufacturing lot must be rejected and must not be used for performing tests. To ensure that users do not obtain test results from these rejected components 110, the test system 115 can suppress display of test results when any of the components 110 in the rejected batch are used with the test system 115.

As noted previously, each component 110 can comprise, for example, a sensor or the like. According to an alternative exemplary embodiment, an inherent property of a manufactured sensor that changes in response to elevated temperature for a period of time with or without deterioration in sensor performance can be used as a quality control indicator of thermal mismanagement of a cartridge. For example, in potentiometric measurements, such as, for example, pH, sodium and potassium, the Nernstian response of an electrode when contacting calibrant fluid and sample can be unaffected by a prior temperature excursion. However, the calibration potential may have shifted by several millivolts. Accordingly, the test system 115 can register such a change in baseline calibration potential from a value in an anticipated range to one outside that range. Such information can be stored, for example, using the log module 135 or in a memory or other computer storage medium associated with the test system 115 for later retrieval and use by the system.

For example, the values in the anticipated range can be stored in a look-up table or other appropriate format. A comparison of the measured calibration potential can be made to the values stored in such a look-up table to determine whether the measured calibration potential is outside the anticipated range. If so, the quality assurance failure alert module 120 can be configured to use the detection of such a change to signal (e.g., via the display module 125) that the component 110 should not be used for patient samples.

According to an additional exemplary embodiment of the present invention, an internal calibration fluid can be used to detect excessive combined thermal and temporal stress of a component 110. It will be understood by those skilled in the art that certain chemical sensors can be more sensitive to thermal stress (e.g., those containing biochemical entities such as enzymes) than others. As an example, it was found that sensors containing the enzyme urease are significantly more sensitive to thermal stress than hematocrit sensors that do not contain biological entities. In the present additional exemplary embodiment, a number of such sensitive sensors can be used to increase the specificity of combined thermal and temporal stress detection. Such a methodology can improve the effectiveness of the test to determine if the thermal-temporal threshold has been exceeded. For purposes of illustration and not limitation, it has been demonstrated that when predefined limits for signals obtained from urea and ionized calcium sensors are applied, greater than 90% of sensors exposed to thermal and temporal stress are suppressed, as illustrated in FIGS. 2-4.

In addition, the use of multiple sensors in combination can allow for improved selectivity for the detection of thermal and temporal stress. Such increased selectivity reduces the burden on the user of the component 110, e.g., a nurse, due to the loss of sensors not exposed to combined thermal and temporal stress. Such a method can ensure that components 110 that have been exposed to sufficient thermal and temporal stress, such that they should be rejected from use, are properly identified. However, such a methodology should not have a high false positive rate, i.e., erroneously reject acceptable components 110. In the aforementioned example involving urea and calcium sensors, it was beneficially found that less than 1% of properly handled sensor results were erroneously suppressed, as illustrated in Table 3.

TABLE 3

Calibrant signal analysis

| Analyte | Sensors exposed to temporal-thermal stress beyond labeled storage conditions | | Sensors not exposed to temporal-thermal stress % results reported with failsafe |
|---|---|---|---|
| | % erroneous results reported without failsafe | % erroneous results reported with failsafe | |
| Sodium | 24 | 3 | 99.6 |
| Potassium | 0 | 0 | 99.6 |
| Ionized Calcium | 54 | 6 | 99.5 |
| Chloride | 15 | 6 | 99.5 |
| BUN | 37 | 13 | 99.5 |
| GLU | 20 | 3 | 99.5 |
| CREA | 40 | 4 | 99.5 |
| TCO2 | 0 | 0 | 99.5 |

Application of exemplary embodiments of the present invention will now be described using the i-STAT system as the test system 115 and (single-use disposable) cartridges for components 110 as an example, where the sensors are stored in a dry state prior to use. These sensors must wet-up and equilibrate with a calibrant fluid immediately prior to performing a blood test. It has been found that the transient output signal of these sensors can be used as an indicator of thermal and temporal stress. The present methodology can be generalized as follows. Thermal stress quality assurance of a quantitative electrochemical physiological sample test system 115 is provided by first contacting a number of electrochemical sensors with a calibrant fluid. The calibrant fluid has known concentrations of various analytes to which each sensor is specific. Such contacting is followed by determining a calibration parameter associated with the concentration of an analyte in the calibrant fluid for each of a selected set of the sensors with respect to a thermal check threshold. It is noted that the calibration parameter can be a calibration voltage that is the potential difference in millivolts (mV) between the sensor and a reference electrode, and the thermal check threshold can be a pre-selected voltage level. Alternatively, the calibration parameter can be a calibration voltage drift rate (associated with the wet-up process) expressed in millivolts per second (mV/s). According to another alternative embodiment, the thermal check threshold can be a combination of the two, e.g., the rate of drift after a pre-selected calibration voltage level is attained. In the last step, the methodology disqualifies the test system 115 from performing a physiological sample test when each of the thermal check thresholds is exceeded for the selected set. For purposes of illustration and not limitation, the selected set of sensors can include a sodium ion-selective electrode and a calcium ion-selective electrode, and, optionally, can include a BUN electrode. Where, for example, a cartridge contains multiple sensors, the selected sensors alone can act as a mechanism for determining thermal and temporal stress for the entire device. It is noted that it will be apparent to those skilled in the software art that a computer algorithm can be written embodying the present methodology (e.g., as part of the quality assurance failure alert module 120) and embedded with other software used to automatically operate the test system 115.

The methodology described above relating to Table 3 was based on accelerated lifetime studies of cartridges containing sensors that are intentionally exposed temporally (for different periods of time) to thermal stress. Analysis of the calibration voltage drift rates and calibration voltages were shown to exhibit changes that can be used to develop an algorithm that identifies thermal and temporal stress. Graphical representations of this phenomenon are illustrated in FIGS. 2-4, which are x-y plots of cal-volt data (x-axis) versus cal-drift (y-axis) for sodium, blood urea nitrogen and calcium, respectively. According to an exemplary embodiment, a version of such an algorithm is as follows:

Step 1: Identify sodium cal-volt (Na VLT c) below thermal check (TC1) threshold.

Step 2: Identify calcium cal-volt (Ca VLT c) below thermal check (TC2) threshold.

Step 3: Suppress results where Na VLT c and Ca VLT c exceed thresholds TC1 and TC2.

For example, the lower limit for Na VLT c can be about 2 mV, and the lower limit for Ca VLT c can be about 30 mV versus an internal silver-silver chloride reference electrode. Various suitable reference electrodes are known in the electrochemical art, as described in, for example, commonly-assigned U.S. Pat. No. 4,933,048.

According to an exemplary embodiment, the selection of a sub-set of tests, e.g., sodium and calcium, can act as a disqualification criterion for a plurality or range of other tests. Thus, quality assurance of a quantitative electrochemical physiological sample test system 115 can be achieved by first contacting a plurality of electrochemical sensors with a calibrant fluid. Subsequently, a calibration parameter associated with the concentration of an analyte in the calibrant fluid can be determined for at least each of a selected sub-set of the plurality of the sensors with respect to a thermal check threshold. The test system 115 can be disqualified from performing a physiological sample test when each of the thermal check thresholds is exceeded for the sub-set. Where the thermal check thresholds are not exceeded, the test system 115 can report the test results in an established manner.

While the above description addressed the preferred embodiments of the present invention, other related methods for assuring quality are further described below. For example, in an alternative exemplary embodiment of the present invention, each component 110 can incorporate a time-temperature indicator or the like that is capable of showing that a predetermined time-temperature threshold has been exceeded. For example, the time-temperature indicator can be a chemical composition coated onto an adhesive patch that is attached to the component 110. A temperature-dependent chemical reaction or phase change causes a color change that is evident to the user, e.g., green to red. Indicator devices that rely on the chemical properties of pigments to change color over time in response to temperature fluctuations are commercially available, such as OnVu™ (offered by Ciba Specialty Chemicals and FreshPoint (both located in Switzerland)). For example, the quality assurance failure alert module 120 can include or be in communication with a suitable optical mechanism and/or image processing algorithm that is capable of discerning changes in color in the time-temperature indicator once the component 110 is inserted into or otherwise engaged with the test system 115. The user will then discard components 110, as appropriate, from use with patient samples that failed the test.

In a further exemplary embodiment of the present invention, each individual component 110 includes a mechanism for determining if that component 110 has experienced a temperature-time profile that exceeds the predetermined limit set by the manufacturer. In such an approach, the test system 115 is configured to automatically detect such an occurrence and suppress reporting of results for a patient sample applied to the cartridge. The test system 115 preferably displays the cause (e.g., via the display module 125), and indicate that the sample should be re-tested with another component 110. For example, the determination can be made automatically using the colored patch methodology described above. Accordingly, the test system 115 can include a photodetector or the like that is capable of interrogating the time-temperature patch on the component 110, before or while tests are being run. Where a color change has occurred and been detected, the test system 115 can suppress the patient test results and alert the user.

In a further exemplary embodiment of the present invention, a temperature-dependent liposomal indicator reagent release step can be used. The concept of using liposomes to discharge molecules from the interior of the liposome into the bulk fluid in a temperature dependent manner is known in the art, as described in, for example: R. L. Magin, "Temperature-Dependent Drug Release from Large Unilamellar Liposomes," Cancer Drug Deliv., 1, 109-17, 1984; S. B. Tiwari, "Temperature Sensitive Liposomes of Plumbagin," J. Drug Targeting 10, 585-91, 2002; P. Chandaroy, "Temperature Controlled Content Release from Liposomes Encapsulating Pluronic F127," J. Controlled Release, 76, 27-37, 2001; and H. Hayashi, "Temperature Sensitive Liposomes Using Copolymers of N-isopropylacrylamide," Bioconj. Chem. 10, 412-8, 1999.

In the present invention, a hermetically-sealed calibrant fluid pouch within each component 110 (e.g., as described in commonly-assigned U.S. Pat. No. 5,096,669) can be used to deliver a calibrant fluid to a test chamber of the test system 115 to calibrate the sensors. According to an exemplary embodiment, the fluid pouch can contain temperature-dependent liposomes in the fluid. In one exemplary embodiment, the liposomes can contain a high level of potassium ions, e.g., 50 mM (or any suitable amount), compared to the bulk of the fluid that has a concentration of, for example, 4 mM (or any suitable amount). Where the component 110 has not experienced elevated temperatures, the liposomes remain whole and the bulk concentration remains at 4 mM potassium. However, when an elevated temperature does occur, the liposomes release potassium and the bulk potassium concentration is substantially increased. As the potassium sensor in the test chamber is expecting to see only a 4 mM concentration, an elevated potassium reading in the calibrant fluid will be indicative of the elevated temperature excursion, and such an indication can be used to determine failure of the quality control test. If the potassium is at the anticipated level, the component 110 can be allowed to continue to perform tests and the results can be reported. It is noted that one skilled in the art of electrochemical measurements will recognize that software algorithms embedded in the test system 115 can be used to perform the analysis. For example, commonly-assigned U.S. Pat. Nos. 5,200,051 and 5,112,455 describe the manufacture and use of various sensors including potassium, glucose and blood urea nitrogen (BUN).

Other alternative exemplary embodiments for using liposomes in the present invention can include detection of the potassium ions released from liposomes by means of a conductivity sensor. It is noted that the hematocrit sensor in an i-STAT cartridge is a conductivity sensor. The increase in potassium ion concentration will be registered by the test system 115 as an unusual elevation in conductivity, associated with the increase in ionic strength of the calibrant fluid, and thus be indicative of a failed quality control test. Furthermore, the liposomes can contain a chemical inhibitor of an enzyme. Such inhibitors are well known in the enzymology art. Sensors in the i-STAT cartridge that measure glucose and BUN, which use the enzymes glucose oxidase and urease, respectively, give an anticipated signal output in the presence of the calibrant fluid that contains known concentrations of glucose and urea. However, where a liposome is incorporated into to the calibrant fluid pouch that contains liposomes with an appropriate enzyme inhibitor, temperature elevation will release the inhibitor and can be detected by the test system 115 due to a lack or reduced signal at the enzymatic sensor. Again, such a situation is indicative of a failed time-temperature quality check, i.e., the thermal and temporal stress exceeding a predetermined thermal-temporal stress threshold level. Known inhibitors of glucose oxidase include copper, silver, and mercury ions, and for urease include various heavy metal ions.

In an alternative exemplary embodiment, the component 110 can contain a pair of adjacent electrical contacts, where a conductive wax coats the gap between the two contacts. When the wax is exposed to an elevated temperature for a given period, it melts and is wicked into an adjacent chamber. Such a process partially or completely removes the wax from the contacts. When the component 110 is subsequently tested by the test system 115, the test system 115 is able to detect whether there is a conductive path between the two contacts. If there is not, the test system 115 can signal that the component 110 has failed the storage temperature quality assurance test. Electrically conductive waxes are well known in the art, as described in, for example, U.S. Pat. No. 4,098,652, where conduction is based on metal-coated particles mixed into the wax to give the desired electrical properties. Other materials that can act as temperature-time excursion indicators include, for example, liquid crystals. For example, HemoTemp II (available from Biosynergy, Elk Grove, Ill.) is an irreversible liquid crystal time-temperature integrator. In another alternative exemplary embodiment, monitoring can occur with respect to thermal stress by means of thermal detectors, such as, for example, a thermistor, a thermocouple, a thermal ink, a temperature-dependent chemical reaction, a temperature-dependent phase change of a material, and the like. Such devices and materials are well known in the art.

According to a further exemplary embodiment, the component 110 is stored in a refrigerator below a predetermined threshold temperature value, preferably below about 5° C., but acceptably within the range of about 2° C. to about 8° C. In other words, the component 110 can be stored in a refrigerated enclosure below a predetermined temperature. The refrigerator can be located, and the testing performed, at various suitable locations, including, but not limited to, a hospital central laboratory, a satellite laboratory, a point-of-care location, a patient bedside, a moving vehicle, a laboratory services vendor, and other like locations. Preferably, the component 110 is removed from the refrigerator prior to use with the test system 115, and permitted to attain an ambient temperature (e.g., room temperature range) prior to being used to perform a test. The components 110 can be contained in a box, e.g., a cardboard box containing about 25 cartridges or other suitable amount of cartridges, and the box can contain a single appended thermal stress detector, such as a color changing wax or like temperature-time indicator. According to such an exemplary embodiment, monitoring occurs with respect to a thermal stress threshold and is performed automatically. The thermal stress detector can be separate from an individual component 110, but in substantially the same thermal environment as the component 110 (e.g., being first in the refrigerator and then at ambient room temperature).

FIG. 22 is a flowchart illustrating steps for quality assurance of a quantitative physiological sample test system performed without running a quality control sample, in accordance with an exemplary embodiment of the present invention. In step 2205, the thermal and temporal stress of a component used with the test system is monitored. When it is desired to run a test using the component and the test system, a component can be obtained from, for example, refrigerated or other appropriate storage in step 2210. In step 2215, a determination is made as to whether the thermal and temporal stress of the component has exceeded a predetermined thermal-temporal stress threshold. If not, then the component can be used with the test system in step 2220. The method can return to step 2210 to obtain another component from storage to perform another test.

However, if it is determined in step 2215 that the predetermined thermal-temporal stress threshold has been exceeded, then in step 2225, alert information is generated indicating that the component has failed quality assurance, and, therefore, should be discarded. Additionally, the display of the test results can be suppressed when the component has failed quality assurance. If the component is associated with a batch or group of substantially similar components, then in step 2230 alert information can be generated indicating that the batch of substantially similar components has also failed quality assurance, and should be discarded.

A process flow diagram is provided in FIG. 23 that serves to provide additional delineation of exemplary embodiments of the present invention. FIG. 23 is a flowchart illustrating a method of quality control based on automatic thermal and temporal monitoring without the use of control fluids, in accordance with an exemplary embodiment of the present invention. For purposes of present illustration and not limitation, the test system 115 can comprise a suitable reader/analyzer, and the components 110 can comprises (single use, disposable) cartridges. In step 2305, the reader is manufactured at the factory. Additionally, cartridges can be manufactured at the factory in step 2310. In step 2315, factory calibration of the reader is performed to confirm the accuracy of the cartridge readings. As discussed previously, such factory-established calibration can confirm the accuracy of the cartridge readings in the factory prior to shipment to the user. As the calibration is factory-set and the reader is explicitly designed to lack functionality that would allow the user to change or alter that calibration in any way, there is no mechanism for the user to misadjust calibration of the reader. As a result, systematic error from calibration can be substantially, if not completely, eliminated.

In step 2320, the reader is shipped from the factory to an appropriate facility (e.g., hospital, physician's office, or the like). In step 2325, the cartridges are also shipped to the facility. In step 2330, qualification and verification of the reader by the user occurs after arrival at the facility to ensure that the reader is functioning properly. Additionally, upon arrival at the facility, the cartridges are stored in an appropriate refrigerated environment in step 2335 for later use. When the user desires to use a cartridge (e.g., for performing a suitable test), the user can obtain a cartridge from the refrigerated storage in step 2340. In step 2345, a determination is made as to whether the thermal stress of the cartridge has been exceeded. If so, then in step 2350 the cartridge and the lot of cartridges are rejected. However, if the thermal stress of the cartridge has not been exceeded, then in step 2355, a determination is made as to whether the temporal stress of the cartridge has been exceeded. If so, then the cartridge and the lot of cartridges are rejected (in step 2350). Otherwise, the quality of the cartridge (and the lot) has been assured, and the cartridge (and reader) can be used to run the patient sample to perform the desired test(s).

The system 100 can include suitable additional modules as necessary to assist or augment the functionality of any or all of the modules of the system 100. For example, the system 100 can include a database module (in addition to the log module 135) that can be in communication with, for example, the quality assurance failure alert module 120. Such a database module can be configured to store any suitable type of information generated or used by or with the system 100, including, for example, thermal/temporal stress recordings, and other like information. Such a database module can be comprised of any suitable type of computer-readable or other computer storage medium capable of storing information in electrical or electronic form.

Alternative architectures or structures can be used to implement the various functions of the system 100 as described herein. For example, functions from two or more modules can be implemented in a single module, or functions from one module can be distributed among several different modules.

In particular, FIG. 24 is a block diagram illustrating a system 2400 for thermal and temporal stress quality assurance of a quantitative electrochemical physiological sample test system, in accordance with an alternative exemplary embodiment of the present invention. The system 2400 includes a plurality of electrochemical sensors 2405 (electrochemical sensor 1, electrochemical sensor 2, . . . , electrochemical sensor N, where N is any suitable number). For example, the component 110 can include one or more of the electrochemical sensors 2405. Each of the plurality of electrochemical sensors can comprise any suitable type of sensor or electrode, such as, for example, a sodium sensor, a potassium sensor, a chloride sensor, a pH sensor, a pO2 sensor, a pCO2 sensor, a lactate sensor, a glucose sensor, a creatinine sensor, a BUN electrode, a calcium sensor, a magnesium sensor, a hematocrit sensor, or the like. According to the present exemplary embodiment, the plurality of electrochemical sensors are contacted with a suitable calibrant fluid.

The system 2400 includes a calibration circuit 2410 in communication with the plurality of electrochemical sensors 2405. For example, the test system 115 can include the calibration circuit 2410 (e.g., as part of or in communication with the quality assurance failure alert module 120). The calibration circuit 2410 is configured to determine a calibration parameter associated with the concentration of an analyte in the calibrant fluid for each electrochemical sensor 2405 of a subset of the plurality of electrochemical sensors 2405 in accordance with a predetermined check threshold. According to an exemplary embodiment, the subset of electrochemical sensors 2405 can comprise, for example, a calcium ion-selective electrode and a BUN electrode. According to an alternative exemplary embodiment, the subset of electrochemical sensors comprise a sodium ion-selective electrode, a calcium ion-selective electrode, and a BUN electrode. However, the subset can include any suitable number and type of electrochemical sensors 2405. The calibration parameter can comprise, for example, a calibration voltage or a calibration voltage drift rate. According to an alternative exemplary embodiment, the calibration parameter can comprise a suitable combination of the calibration voltage and the calibration voltage drift rate. However, any appropriate calibration parameter can be used for purposes of the thermal and temporal stress quality assurance. The calibration circuit 2410 is configured to disqualify the test system from performing a physiological sample test when the predetermined check threshold is exceeded for each electrochemical sensor 2405 of the subset.

Merely for purposes of illustration and not limitation, the system 2400 can include a first electrochemical sensor 2405 and a second electrochemical sensor 2405. The first and second electrochemical sensors 2405 are each contacted with a calibrant fluid. The calibration circuit 2410 can be configured to determine a first calibration voltage for the first electrochemical sensor 2405 associated with the concentration of a first analyte in the calibrant fluid in accordance with a first check threshold. The calibration circuit 2410 can also be configured to determine a second calibration voltage for the second electrochemical sensor 2405 associated with the concentration of a second analyte in the calibrant fluid in accordance with a second check threshold. The calibration circuit 2410 can be configured to disqualify the test system from performing a physiological sample test when both the first and second check thresholds are exceeded. Appropriate check thresholds can be determined and established in accordance with the methodology discussed herein.

In the previous discussion, the preferred exemplary embodiments focused on a methodology that entirely removed the need for the use of quality control fluids. In the subsequent description, alternative exemplary embodiments of the present invention focus on a methodology that substantially reduces the need for quality control fluids for quality assurance of point-of-care and bedside testing. Once again, the preferred embodiments will be illustrated with respect to the operation of the exemplary i-STAT system. However, those skilled in the art will recognize that the principles described also apply to other similar clinical sample testing systems.

It has been discovered that a blood testing cartridge (component 110) that contains various sensors is amenable to quality assurance testing for thermal and temporal stress based on a single control fluid. Here, the testing system 115 of which such a component 110 forms a part is still able to deliver performance precision of better than about 10% for each type of sensor-based test.

As described above, a user needs to have an accurate and precise analytical measurement. Such a need gives rise to a requirement for a quality check, or a failure alert mechanism, for components 110 that may have had performance compromised by component 110 storage outside the labeled storage recommendations for either or both time and temperature. For purposes of discussion, incorrect storage conditions can be designated as cartridge thermal mismanagement.

The present alternative exemplary embodiment is best described by contrasting a specific example with the conventional methodology. A given specific example is the i-STAT CHEM8+ cartridge described above that performs a set of chemistry tests and a hematocrit measurement on a single blood sample. The conventional quality assurance methodology for determining thermal stress is to run four separate cartridges, one each with the following quality control fluids: Chemistries Level 1, Chemistries Level 3, RNA Hematocrit Level 1 and RNA Hematocrit Level 3 (see FIGS. 9 and 10). As described above, running four separate cartridges can be burdensome for point-of-care users. However, such a conventional quality assurance methodology reflects the manufacturer's knowledge of product performance (e.g., accuracy, precision) as a function of temperature and time, and has been established such that the boundary conditions are far removed from those time and temperature conditions that give undesirable product performance.

It is reasonable to expect that the aggregate product performance arises from thermally-induced component 110 changes, as indicated by the accuracy and precision of each sensor. To provide a methodology that uses only a single fluid, it is necessary to evaluate the performance of each individual sensor in the CHEM8+ cartridge as a function of thermal and temporal stress to find the best single control fluid composition that facilitated acceptable quality assurance. Regarding the chemistry tests, FIGS. 5-7 and 11 illustrate that the BUN, creatinine and ionized calcium sensors are the most sensitive to temporal and thermal stress in Chemistries Level 1 and 3, and that these three sensors are more sensitive to Level 1 than Level 3. The experimental evidence indicates that each sensor does not respond equally to thermal and temporal stress, with some sensors being more sensitive than others to thermal and temporal stress. It is apparent from FIGS. 5-7 and 11 that those sensors with lesser sensitivity include sodium, potassium, chloride, total carbon dioxide (TCO2), and glucose.

It has been found that the hematocrit sensor is insensitive to thermal and temporal stress in RNA Medical Hct control fluids Levels L1 and L3, as illustrated in FIGS. 23(A) and 23(B), respectively. The graphs in FIGS. 25(A) and 25(B) illustrate the behavior of the CHEM8+ hematocrit sensor under thermal stress (T=35° C. for 4 weeks), and compare the performance of cartridges stored at T=5° C. for 1 month to those stored at T=5° C. for 7 months. In FIGS. 25(A) and 25(B), the test fluids used are the RNA Medical hematocrit Levels L1 and L3, respectively (available from RNA Medical, 7 Jackson Road, Devens, Mass. 01434).

Returning to the three more sensitive tests, BUN, creatinine and ionized calcium (iCa), the rate of change in L1 (Chemistry Level 1 control) concentrations are a function of temperature. Such a result is consistent with a thermally-activated mechanism that can be quantified in an Arrhenius plot. FIG. 26 illustrates a plot of ionized calcium sensors in an i-STAT CHEM8+ cartridge tested with Level 1 chemistry control fluid after various storage times at 5° C., 25° C., 30° C., and 35° C. FIG. 27 is a graphical representation illustrating the data from FIG. 26 as an Arrhenius plot. FIG. 28 illustrates a plot of blood urea nitrogen (BUN) sensors in an i-STAT CHEM8+ cartridge tested with Level 1 chemistry control fluid after various storage times at 5° C., 25° C., 30° C., and 35° C. FIG. 29 illustrates the data from FIG. 28 as an Arrhenius plot. FIG. 30 is a graphical representation of a plot of creatinine sensors in an i-STAT CHEM8+ cartridge tested with Level 1 chemistry control fluid after various storage times at 5° C., 25° C., 30° C., and 35° C. FIG. 31 illustrates the data from FIG. 30 as an Arrhenius plot. It is noted that an Arrhenius plot graphs $\ln(-\Delta conc/\Delta time)$ against the inverse of the temperature. Rates of change of concentration over time at all temperatures can be predicted from the Arrhenius equation, allowing for the correlation of short-duration, high-temperature experiments to long-duration, low-temperature experiments.

In accordance with the data from FIGS. 26-31 (and combined in summary form in FIG. 32), a CHEM8+ cartridge thermal mismanagement quality check can be established using the L1 control fluid. Using these data, the concentration readings of the iCa, creatinine and BUN sensors can be predicted at various storage temperatures over time. Inaccurate results are those that are defined as greater than ATE (e.g., for L1 fluid: iCa: 5%; creatinine: 15%; BUN: 9%). For a given temperature, a predicted time-to-failure can be made, based on the mean reading≥ (target+ATE). Given a normal distribution of concentration reading, the predicted months to failure describes that time at which 50% of results will be inaccurate, i.e., outside the target±ATE. Knowledge of the precision and standard deviation can then be used to adjust the control limits to define a smaller percentage of inaccurate results. For example, a 5% inaccurate result threshold may be desirable. It has been found that the predicted months to failure for the three analytes converge as storage temperature increases. Thus, any one of iCa, BUN or creatinine results in L1 fluid will satisfactorily indicate thermal mismanagement of CHEM8+ cartridges.

In accordance with such a methodology, the user can implement a thermal mismanagement quality control or failure alert mechanism by a testing protocol using a single cartridge and a single control fluid, per test event. Accordingly, the user can compare the results of the given single cartridge against an acceptable test range (provided by the cartridge manufacture) for iCa, BUN and creatinine analyte results in the L1 fluid. Failure to achieve a result within the specified range for each of the three tests will alert the user to a failure associated with thermal mismanagement. Specifically, the failure alert will be triggered (e.g., by the quality assurance failure alert module 120) if any one analyte is outside the specified target range.

As discussed previously, it will be understood by those skilled in the art that a combined thermal and temporal stress value can be based on the integral combination of the two effects in determining the system threshold value. For example, a threshold value could be exceeded by a significantly elevated temperature excursion for a short period; likewise, the same threshold could also be exceeded by a smaller elevated temperature excursion for a long period. In another example, the temperature may not have exceeded the designated storage temperature, but the allowable time or shelf-life at that temperature may be exceeded. Consequently, the predetermined thermal-temporal stress threshold value would be exceeded. Experimentation of the general type described in this disclosure will enable a manufacture to determine how to set a product-specific threshold value.

For ease of presentation, all of the analyte targets available from the L1 fluid can be presented for Na, K, Cl, iCa, glucose, creatinine, BUN and TCO2 in a package insert provided in each box of components 110. By way of example, FIG. 33 illustrates one such package insert layout. It is noted that in FIG. 33, target and range data are omitted for non-critical tests. The following quality control rules can accordingly apply:

If CHEM8+ cartridge expiry date is less than current date, then the cartridge is expired and cartridges from the lot should not be used.

If one of iCa, BUN or Creatinine fail to give a result in the desired range, then consider cartridge lot thermally mismanaged and do not use.

Those skilled in the art will recognize that while the control fluid composition of Chemistries Level 1 is best suited to determining thermal stress of a CHEM8+ cartridge, other cartridges and components 110 with different test combinations can use a single control fluid with a different combination of analyte concentrations and use one or more different tests to determine thermal mismanagement. Those skilled in the art will also recognize that by using the general principles of the experimental testing process described above for the CHEM8+ cartridge, the skilled artisan can arrive at a suitable composition for a different component 110 with different tests without undue experimentation.

A process flow diagram is provided in FIG. 34 that serves to provide additional delineation of the present alternative exemplary embodiment of the invention. FIG. 34 is a flowchart illustrating a method of quality control based on thermal and temporal monitoring using a single control fluid or a limited combination thereof, in accordance with an exemplary embodiment of the present invention.

Merely for purposes of present illustration and not limitation, the methodology illustrated in FIG. 34 will be described in accordance with a reader/analyzer and (single use, disposable) cartridges, although other suitable types of test systems and components can be used. In step 3405, the reader is manufactured. In step 3410, the cartridges are also manufactured. In step 3415, factory calibration of the reader is performed to confirm the accuracy of the cartridge readings. In step 3420, the reader is shipped from the factory to the facility. In step 3425, qualification and verification of the reader by the user occurs after arrival at the facility to ensure that the reader is functioning properly. In step 3420, the cartridges are shipped from the factory to the facility. Upon arrival, in step 3435, a temperature strip or other suitable temperature-time indicator associated with the cartridges is tested or otherwise interrogated to determine whether the thermal-temporal stress of the cartridges was exceeded while in transit. If so, then in step 3440 the entire batch or lot of cartridges is rejected and should not be used.

If both the qualification/verification of the reader and temperature-time interrogation of the cartridges pass, then in step 3445, liquid quality control measures can be run. In step 3450, the results of the liquid quality control test are recorded. In step 3455, these results are compared to (manufacturer determined) target results for the test system and cartridges. If the liquid quality control test results do not substantially compare with the target results, then in step 3460 the user is instructed to contact the manufacturer's technical support or other appropriate assistance to resolve the problem (e.g., replacement of the reader and/or cartridges). Otherwise, in step 3465, the cartridges are stored in an appropriate refrigerated environment.

When the user desires to perform a test using the reader and cartridges, in step 3470 the (refrigerated) storage conditions for the cartridges are verified. If the thermal stress of the cartridges has (potentially) been exceeded, then the methodology returns to step 3445 to re-run the liquid quality control measures to determine whether the cartridges can be used. Otherwise, in step 3475, a determination is made as to whether the temporal stress of the cartridges has been exceeded (e.g., whether the expiration date of the cartridges has expired). If so, then the lot of cartridges is rejected in step 3440. Otherwise, the patient samples can be run using the cartridge in step 3480. Once the test(s) have been run, another cartridge can be obtained from (refrigerated) storage. Accordingly, the methodology returns to step 3470 to ensure that the thermal and temporal stress of the cartridges has not been exceeded.

Each, all or any combination of the steps of a computer program as illustrated in FIGS. 22, 23, and 34, as well as those described herein, for quality assurance of a quantitative physiological sample test system can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. As used herein, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium can include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CDROM).

It will be appreciated by those of ordinary skill in the art that the present invention can be embodied in various specific forms without departing from the spirit or essential characteristics thereof. The presently disclosed embodiments are considered in all respects to be illustrative and not restrictive. The scope of the invention is indicated by the appended claims, rather than the foregoing description, and all changes that come within the meaning and range of equivalence thereof are intended to be embraced.

All United States patents and patent applications, foreign patents and patent applications, and publications discussed above are hereby incorporated by reference herein in their entireties to the same extent as if each individual patent, patent application, or publication was specifically and individually indicated to be incorporated by reference in its entirety.

What is claimed is:

1. A system for thermal and temporal stress quality assurance of a quantitative electrochemical physiological sample test system, comprising:
    a plurality of electrochemical sensors,
        wherein the plurality of electrochemical sensors comprises a subset of the plurality of electrochemical sensors contacted with a calibrant fluid having known concentrations of analytes, to which each sensor of the subset of electrochemical sensors is specific,
        and wherein the subset of electrochemical sensors generates transient electrical signals upon being contacted, wetting up and equilibrating with the calibrant fluid; and
    a calibration circuit in communication with the subset of electrochemical sensors,
        wherein the calibration circuit is configured, upon obtaining the transient electrical signals from the subset of electrochemical sensors, to determine a calibration parameter associated with a concentration of an analyte in the calibrant fluid for each electrochemical sensor of the subset of electrochemical sensors, to compare the calibration parameter to a predetermined check threshold stored in the system and to determine whether the calibration parameter exceeds the predetermined check threshold using a computer algorithm embedded within software used to operate the system, wherein a determination that the calibration parameter exceeds the predetermined check threshold is indicative that an electrochemical sensor was exposed temporally to thermal stress,
        wherein the calibration circuit is configured to generate alert information disqualifying the entire test system from performing a physiological sample test when the predetermined check threshold is exceeded for each electrochemical sensor of the subset of the electrochemical sensors, which is indicative of incorrect storage conditions of the quantitative electrochemical physiological sample test system;
    and wherein the calibration parameter comprises;
        a calibration voltage that is a difference between a voltage generated by each electrochemical sensor of the subset of electrochemical sensors and a corresponding reference electrode;
        a calibration voltage drift rate associated with the wetting-up of each electrochemical sensor of the subset of electrochemical sensors; or,
        a combination of said calibration voltage and said calibration voltage drift rate.

2. The system of claim 1, wherein the subset of electrochemical sensors comprises a calcium ion-selective electrode and a BUN electrode.

3. The system of claim 1, wherein the subset of electrochemical sensors comprises a sodium ion-selective electrode, a calcium ion-selective electrode, and a BUN electrode.

4. The system of claim 1, wherein the plurality of electrochemical sensors comprises one of a sodium sensor, a potassium sensor, a chloride sensor, a pH sensor, a $pO_2$-sensor, a $pCO_2$ sensor, a lactate sensor, a glucose sensor, a creatinine sensor, a BUN electrode, a calcium sensor, a magnesium sensor, and a hematocrit sensor.

5. The system of claim 1, wherein the subset of electrochemical sensors of the plurality of electrochemical sensors is configured to determine the thermal and temporal stress for all of the plurality of electrochemical sensors, and when the predetermined check threshold is exceeded for each electrochemical sensor of the subset of the electrochemical sensors, it is indicative that all of the plurality of the electrochemical sensors was exposed temporally to thermal stress.

6. The system of claim 1, wherein the system is configured to display an alert when the alert information is generated.

7. The system of claim 1, further comprising a display module in communication with the calibration circuit, the display module configured to display an alert when the alert information is generated.

8. The system of claim 1, wherein the system is configured to suppress display of test results, when the alert information is generated.

9. A system for evaluating thermal and temporal stress quality assurance of a quantitative electrochemical physiological sample test system, the system comprising:
  a plurality of electrochemical sensors configured to perform a plurality of quantitative electrochemical physiological sample tests, wherein the plurality of electrochemical sensors includes a subset of electrochemical sensors that are further configured to determine the thermal and temporal stress for all of the plurality of electrochemical sensors, the subset of electrochemical sensors including a first electrochemical sensor and a second electrochemical sensor, wherein the subset of electrochemical sensors generates transient electrical signals upon being contacted, wetting up and equilibrating with a calibrant fluid;
  a thermal and temporal stress monitor module configured to:
    (i) determine a first calibration voltage for the first electrochemical sensor upon obtaining a transient electrical signal from the first electrochemical sensor, wherein the first calibration voltage is a difference between a voltage generated by the first electrochemical sensor and a first reference electrode, is associated with a concentration of a first analyte in the calibrant fluid, and a rate of change in the concentration of the first analyte is a function of temperature, and
    (ii) determine a second calibration voltage for the second electrochemical sensor upon obtaining a transient electrical signal from the second electrochemical sensor, wherein the second calibration voltage is a difference between a voltage generated by the second electrochemical sensor and a second reference electrode, same or different as the first reference electrode, is associated with a concentration of a second analyte in the calibrant fluid, and a rate of change in the concentration of the second analyte is a function of temperature,
  a quality assurance failure alert module configured to
    (i) receive the first calibration voltage from the thermal and temporal stress monitor module and determine whether the first calibration voltage exceeds a first check threshold, using a computer algorithm embedded within software used to operate the system, wherein a determination that the first calibration voltage exceeds the first check threshold is indicative that the first electrochemical sensor was exposed temporally to thermal stress,
    (ii) receive the second calibration voltage from the thermal and temporal stress monitor module and determine whether the second calibration voltage exceeds a second check threshold, using the computer algorithm embedded within software used to operate the system, wherein a determination that the second calibration voltage exceeds the second check threshold is indicative that the second electrochemical sensor was exposed temporally to thermal stress, and
    (iii) generate alert information disqualifying all of the plurality of electrochemical sensors from performing the plurality of quantitative electrochemical physiological sample tests when the first calibration voltage exceeds the first check threshold and the second calibration voltage exceeds the second check threshold.

10. The system of claim 9, wherein the first electrochemical sensor comprises a sodium ion-selective electrode, and wherein the second electrochemical sensor comprises a calcium ion-selective electrode.

11. The system of claim 9, wherein the first sensor comprises a calcium ion-selective electrode and the second sensor comprise a BUN electrode.

12. The system of claim 9, wherein the subset of the electrochemical sensors comprises a combination of two of a sodium ion-selective electrode, a calcium ion-selective electrode, and a BUN electrode.

13. The system of claim 9, wherein the subset of the electrochemical sensors comprises a combination of two of a sodium sensor, a potassium sensor, a chloride sensor, a pH sensor, a $pO_2$-sensor, a $pCO_2$ sensor, a lactate sensor, a glucose sensor, a creatinine sensor, a BUN electrode, a calcium sensor, a magnesium sensor, and a hematocrit sensor.

14. The system of claim 9, wherein the system is configured to display an alert when the alert information is generated.

15. The system of claim 9, further comprising a display module in communication with the quality assurance failure alert module, the display module configured to display an alert when the alert information is generated.

16. The system of claim 9, wherein the system is configured to suppress display of test results, when the alert information is generated.

* * * * *